United States Patent
Endo et al.

(10) Patent No.: US 8,536,176 B2
(45) Date of Patent: Sep. 17, 2013

(54) GPR119 AGONIST

(75) Inventors: Tsuyoshi Endo, Misato (JP); Rie Takahashi, Misato (JP); Hiroto Tanaka, Misato (JP); Toshihiro Kunigami, Misato (JP); Takaichi Hamano, Misato (JP); Mai Okamura, Misato (JP); Kaoru Hara, Misato (JP)

(73) Assignee: Nippon Chemiphar Co., Ltd., Chiyoda-ku, Tokyo (JP)

( * ) Notice: Subject to any disclaimer, the term of this patent is extended or adjusted under 35 U.S.C. 154(b) by 0 days.

(21) Appl. No.: 13/056,673

(22) PCT Filed: Jul. 31, 2009

(86) PCT No.: PCT/JP2009/063982
§ 371 (c)(1),
(2), (4) Date: Jan. 31, 2011

(87) PCT Pub. No.: WO2010/013849
PCT Pub. Date: Feb. 4, 2010

(65) Prior Publication Data
US 2011/0137032 A1 Jun. 9, 2011

(30) Foreign Application Priority Data
Aug. 1, 2008 (JP) ................................ 2008-200229

(51) Int. Cl.
*A61K 31/50* (2006.01)
*A61K 31/501* (2006.01)
(52) U.S. Cl.
USPC ...... 514/252.03; 514/317; 514/332; 544/238; 546/193; 546/256
(58) Field of Classification Search
USPC .................. 546/194, 279.1, 268.1
See application file for complete search history.

(56) References Cited

U.S. PATENT DOCUMENTS

| 6,051,712 | A | * | 4/2000 | Binggeli et al. | 546/194 |
| 7,807,671 | B2 | * | 10/2010 | Wang et al. | 514/234.5 |
| 2007/0093528 | A1 | * | 4/2007 | Kuwabara et al. | 514/332 |
| 2008/0207641 | A1 | * | 8/2008 | Bohnert et al. | 514/255.05 |
| 2010/0267721 | A1 | * | 10/2010 | Hohlweg et al. | 514/235.5 |
| 2011/0294836 | A1 | * | 12/2011 | Song et al. | 514/269 |
| 2012/0289507 | A1 | * | 11/2012 | He et al. | 514/236.5 |

FOREIGN PATENT DOCUMENTS

| WO | WO 97/09311 A1 | 3/1997 |
| WO | WO 03/099266 A2 | 12/2003 |
| WO | WO 2008063504 A2 * | 5/2008 |
| WO | WO 2010/008739 A2 | 1/2010 |

\* cited by examiner

*Primary Examiner* — James O Wilson
*Assistant Examiner* — Alexander R Pagano
(74) *Attorney, Agent, or Firm* — Nixon Peabody LLP; Jeffrey L. Costellia

(57) ABSTRACT

A cyclic amine derivative represented by the formula (II) is a GPR119 agonist, and is used as an agent for treating diabetes.

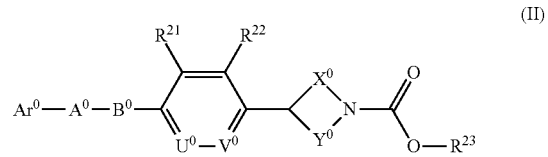

wherein $Ar^0$ is phenyl or phenyl having a substituent such as $C_{1-8}$ alkylsulfonyl or the like, pyridyl, or pyridyl having a substituent such as $C_{1-8}$ alkylsulfonyl;
$A^0$ is $(CH_2)_p$, O, or the like;
$B^0$ is $(CH_2)_q$, or the like, provided that $B^0$ is neither O nor $NR^{25}$ when $A^0$ is O or $NR^{24}$;
one of $U^0$ and $V^0$ is N, and the other is N or $CR^{26}$;
each of $X^0$ and $Y^0$ is $C_{1-3}$ alkylene or $C_{1-3}$ alkylene having a substituent;
$R^{23}$ is a $C_{1-8}$ alkyl group or the like;
each of $R^{21}$ and $R^{22}$ is hydrogen, a halogen atom, or the like.

5 Claims, No Drawings

GPR119 AGONIST

FIELD OF THE INVENTION

The present invention relates to a GPR119 agonist.

BACKGROUND OF THE INVENTION

Diabetes is a life-style related disease and the number of patients increases all over the world. The treatments for diabetes are classified into diet, exercise and drug therapy (injectable insulin and an oral anti-diabetic drug). Some oral anti-diabetic drugs, for example, α-glucosidase inhibitors (acarbose, voglibose), insulin-sensitizing agents (pioglitazone hydrochloride), biguanides (metformin hydrochloride), sulfonylureas (glibenclamide, glimepiride) and short-acting insulin secretagogues (mitiglinide calcium hydrate) are commercially available in Japan.

On the other hand, an incretin mimetics (excenatide) and a DPP IV inhibitor (sitagliptin), which accelerates secretion of insulin, are commercially available abroad. The incretin is a gastrointestinal hormone, which accelerates secretion of insulin. Further, SGLT inhibitors have been developed abroad.

GPR119 has been reported as a G protein-coupled-receptor (GPCR) whose endogenous ligand is N-oleoylethanolamide and which stimulate insulin secretion from pancreatic β-cells (Non-patent Document 1: Overton H A at al., Cell Metab., 2006, 3, 167-75). It has been reported that GPR119 agonist increases the plasma concentration of Glucagon like peptide-1 (GLP-1), one of incretins (Non-patent Document 2: Chu Z L at al., Endocrinology, 2008, 149, 2038-47), which may indirectly relate to stimulation of insulin secretion. It has been further reported that GPR119 agonist surpresses a weight increase in rats fed a high-fat diet (Non-patent Document 1), which may relate to energy metabolism. For the reasons mentioned above, the GPR119 agonist has been expected as a drug not only for diabetes but also for life-style related diseases such as obesity and metabolic syndrome.

Compounds such as (A) are described in WO 2004/076413 (Patent Document 1) as the GPR119 agonist.

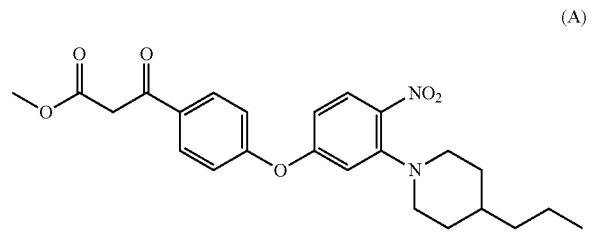 [SMILES: CCCC1CCN(c2cc(Oc3ccc(C(=O)CC(=O)OC)cc3)ccc2[N+](=O)[O-])CC1]
(A)

Compounds such as (B) are described in WO 2004/065380 (Patent Document 2) as the GPR119 agonist.

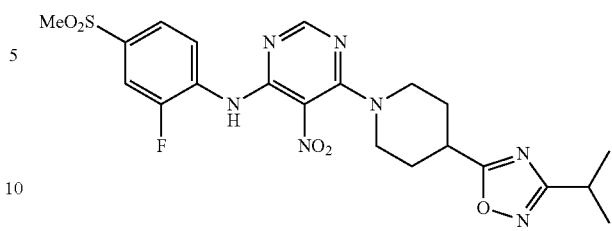
(B)

Compounds such as (C) are described in WO 2005/007647 (Patent Document 3) as the GPR119 agonist.

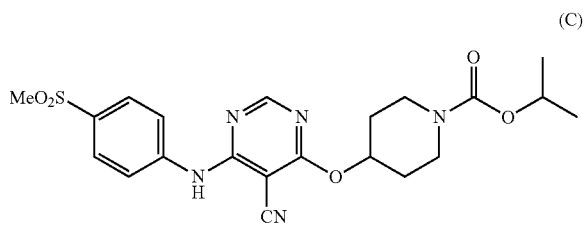 [SMILES: CC(C)OC(=O)N1CCC(Oc2ncnc(Nc3ccc(S(C)(=O)=O)cc3)c2C#N)CC1]
(C)

Compounds such as (D) are described in WO 2007/003960 (Patent Document 4) as the GPR119 agonist.

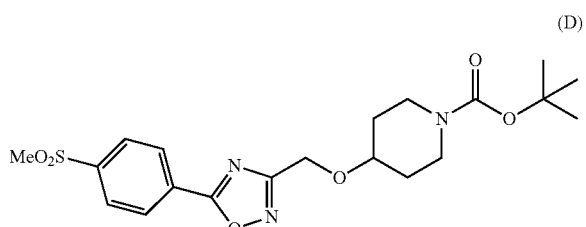
(D)

Compounds such as (E) are described in WO 2008/025798 (Patent Document 5) as the GPR119 agonist.

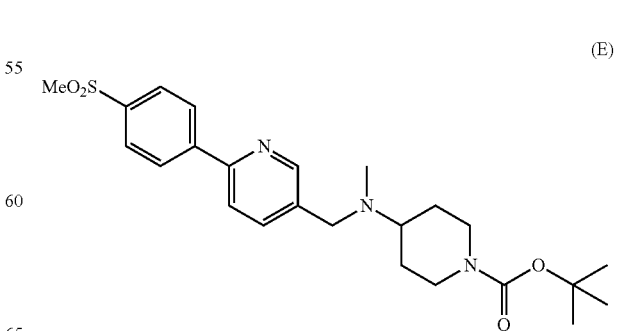
(E)

Compounds such as (F) are described in WO 2008/008887 (Patent Document 6) as the GPR119 agonist.

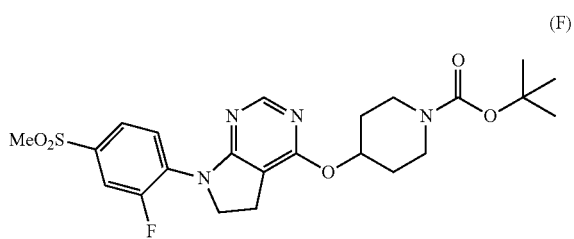 [SMILES: CC(C)(C)OC(=O)N1CCC(Oc2ncnc3c2CCN3c2ccc(S(C)(=O)=O)cc2F)CC1]

(F)

However, there in no description of the compound represented by the formula (I) in which the carbon atom contained in the pyridine or pyridazine ring is directly combined with the carbon atom contained in the cyclic amine.

Compounds such as (G) and (H) are described in WO 97/09311 (Patent Document 7), which have a pyridylpiperidine structure.

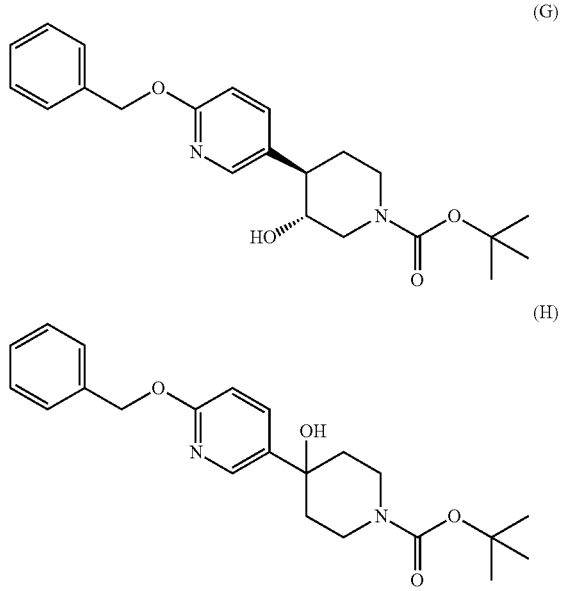

(G)

(H)

Compounds such as (J) are described in WO 2002/042305 (Patent Document 8).

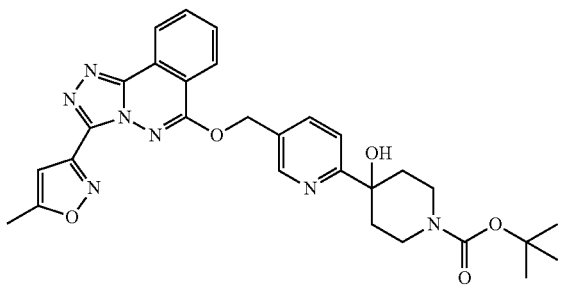

(J)

These compounds are intermediates of a drug for Alzheimer disease or $GABA_A$ agonist. There is no description in Patent Documents 7 and 8 that these compounds are used as GPR119 agonists.

DISCLOSURE OF THE INVENTION

The object of the invention is to provide a compound represented by the formula (I) described in (A) or (B), or a pharmaceutically acceptable salt thereof. The object also is to provide a cyclic amine derivative represented by the formula (II) described in (C) or (D), or a pharmaceutically acceptable salt thereof. The object further is to provide a GPR119 agonist or an agent for treating diabetes containing the compound or salt thereof as an active ingredient.

(A) The present invention relates to a compound having the following formula (I) or a pharmaceutically acceptable salt thereof:

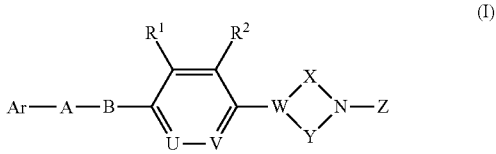

(I)

wherein Ar is an aryl or five-membered or six-membered heteroaryl group, which optionally has a substituent selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, a $C_{2-12}$ dialkylaminosulfonyl group, phenylsulfonyl, and a five-membered or six-membered heteroaryl group;

A is $(CH_2)_m$, O, S, $NR^3$, or a bond, wherein m is an integer of 1 to 3, and $R^3$ is hydrogen or a $C_{1-8}$ alkyl group;

B is $(CH_2)_n$, CH=CH, O, S, or $NR^4$, wherein n is an integer of 1 to 3, and $R^4$ is hydrogen or a $C_{1-8}$ alkyl group, provided that B is neither O, S, nor $NR^4$ when A is O, S, or $NR^3$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl, a alkoxy group, a $C_{1-8}$ alkyl group having one to three halogen atoms, or a $C_{1-8}$ alkoxy group having one to three halogen atoms;

X is a $C_{1-3}$ alkylene group, which optionally has a substituent selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-8}$ alkylene group, which optionally has a substituent selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is $C(O)OR^7$, $C(O)R^8$, $C(O) NR^{10}R^{11}$, $CH_2C(O)N(R^{12})(R^{13})$, or a five-membered or six-membered heteroaryl group comprising carbon and nitrogen atoms, said carbon atom combining to the nitrogen atom of the neighboring cyclic amine, and said heteroaryl group optionally having a substituent selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms, wherein each of $R^7$, $R^8$, $R^9$, $R^{10}$, $R^{11}$, $R^{12}$, and $R^{13}$ independently is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^1$ and $R^2$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

(B) The invention also relates to a compound having the following formula (I) or a pharmaceutically acceptable salt thereof:

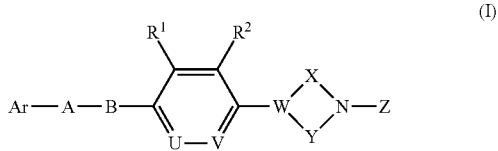

(I)

wherein Ar is an aryl or five-membered or six-membered heteroaryl group, which optionally has a substituent selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, phenylsulfonyl, and a five-membered or six-membered heteroaryl group;

A is $(CH_2)_m$, O, $NR^3$, or a bond, wherein m is an integer of 1 to 3, and $R^3$ is hydrogen or a $C_{1-8}$ alkyl group;

B is $(CH_2)_n$, O, or $NR^4$, wherein n is an integer of 1 to 3, and $R^4$ is hydrogen or a $C_{1-8}$ alkyl group, provided that B is neither O nor $NR^4$ when A is O or $NR^3$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

X is a $C_{1-8}$ alkylene group, which optionally has a substituent selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-8}$ alkylene group, which optionally has a substituent selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is $C(O)OR^7$, $C(O)R^8$, $C(O) NR^{10}R^{11}$, $CH_2C(O)N(R^{12})(R^{13})$, or a five-membered or six-membered heteroaryl group comprising carbon and nitrogen atoms, said carbon atom of the ring being combined to nitrogen atom of the neighboring cyclic amine, and said heteroaryl group optionally having a substituent selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms, wherein each of $R^7$, $R^8$, $R^9$, $R^{10}$, $R^{11}$, $R^{12}$, and $R^{13}$ is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^1$ and $R^2$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

The invention further relates to an agent for treating diabetes containing the compound of the formula (I) described in (A) or (B), or a pharmaceutically acceptable salt thereof as an active ingredient.

The invention further relates to a GPR119 agonist containing the compound of the formula (I) described in (A) or (B), or a pharmaceutically acceptable salt thereof as an active ingredient.

(C) The invention also relates to a cyclic amine derivative having the following formula (II) or a pharmaceutically acceptable salt thereof:

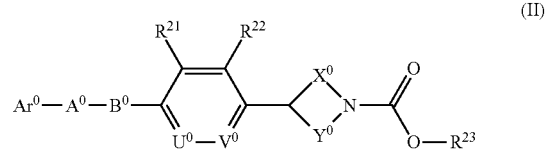

(II)

wherein $Ar^0$ is phenyl, phenyl having a substituent, pyridyl, or pyridyl having a substituent, said substituent being selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, a $C_{2-12}$ dialkylaminosulfonyl group, phenylsulfonyl, and a five-membered or six-membered heteroaryl group;

$A^0$ is $(CH_2)_p$, O, S, $NR^{24}$ or a bond, wherein p is an integer of 1 to 3, and $R^{24}$ is hydrogen or a $C_{1-8}$ alkyl group;

$B^0$ is $(OH_2)_q$, CH=CH, O, S, or $NR^{25}$, wherein q is an integer of 1 to 3, and $R^{25}$ is hydrogen or a $C_{1-8}$ alkyl group, provided that $B^0$ is neither O, S, nor $NR^{25}$ when $A^0$ is O, S, or $NR^{24}$;

one of $U^0$ and $V^0$ is N, and the other is N or $CR^{26}$, wherein $R^{26}$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

each of $X^0$ and $Y^0$ independently is a $C_{1-3}$ alkylene group, which optionally has a substituent selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

$R^{23}$ is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^{21}$ and $R^{22}$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

(D) The invention further relates to a cyclic amine derivative having the following formula (II) or a pharmaceutically acceptable salt thereof:

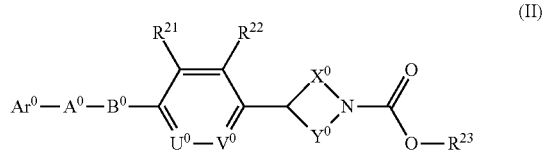

(II)

wherein $Ar^0$ is phenyl, phenyl having a substituent, pyridyl, or pyridyl having a substituent, said substituent being selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a alkylaminosulfonyl group, phenylsulfonyl, and a five-membered or six-membered heteroaryl group;

$A^0$ is $(CH_2)_p$, O, $NR^{24}$, or a bond, wherein p is an integer of 1 to 3, and $R^{24}$ is hydrogen or a $C_{1-8}$ alkyl group;

$B^0$ is $(CH_2)_q$, O, or $NR^{25}$, wherein q is an integer of 1 to 3, and $R^{25}$ is hydrogen or a $C_{1-8}$ alkyl group, provided that $B^0$ is neither O nor $NR^{25}$ when $A^0$ is O or $NR^{24}$;

one of $U^0$ and $V^0$ is N, and the other is N or $CR^{26}$, wherein $R^{26}$ is hydrogen, a halogen atom, hydroxyl, a $C_{1-8}$ alkyl group, a alkoxy group, a $C_{1-8}$ alkyl group having one to three halogen atoms, or a $C_{1-8}$ alkoxy group having one to three halogen atoms;

each of $X^0$ and $Y^0$ independently is a $C_{1-8}$ alkylene group, which optionally has a substituent selected from the group consisting of a halogen atom, a $C_{1-8}$ alkyl group, a alkoxy group, a $C_{1-8}$ alkyl group having one to three halogen atoms, and a $C_{1-8}$ alkoxy group having one to three halogen atoms;

$R^{23}$ is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^{21}$ and $R^{22}$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

The invention furthermore relates to an agent for treating diabetes containing the cyclic amine derivative of the formula (II) described in (C) or (D), or a pharmaceutically acceptable salt thereof as an active ingredient.

The invention furthermore relates to a GPR119 agonist containing the cyclic amine derivative of the formula (II) described in (C) or (D), or a pharmaceutically acceptable salt thereof as an active ingredient.

BEST MODE OF THE INVENTION

The present invention is described below in more detail.
Preferred embodiments of the compound of the formula (I) described in (A) or (B) are shown below.

(1) A compound of the formula (I) described in (A) or (B), or a pharmaceutically acceptable salt thereof, wherein Ar is phenyl, which optionally has a substituent selected from the group consisting of a halogen atom, nitro, cyano, hydroxyl, a $C_{1-8}$ alkyl group, a alkoxy group, a $C_{1-8}$ alkyl group having one to three halogen atoms, a $C_{1-8}$ alkoxy group having one to three halogen atoms, phenoxy, an alkoxycarbonyl group having a alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a alkylsulfonyl group, sulfamoyl, a $C_{1-8}$ alkylaminosulfonyl group, phenylsulfonyl, and a five-membered or six-membered heteroaryl group.

(2) A compound of the formula (I) described in (A) or (B), or a pharmaceutically acceptable salt thereof, wherein Ar is pyridyl, which optionally has a substituent selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a alkylsulfinyl group, a $C_{1-8}$ alkylsulfonyl group, sulfamoyl, a $C_{1-8}$ alkylaminosulfonyl group, phenylsulfonyl, and a five-membered or six-membered heteroaryl group.

(3) A compound of the formula (I) described in (A) or (3), or a pharmaceutically acceptable salt thereof, wherein Ar is phenyl having only one substituent or pyridyl having only one substituent, said substituent being selected from the group consisting of an alkoxycarbonyl group having a $C_{1-8}$ alkoxy group, an alkylaminocarbonyl group having a $C_{1-8}$ alkyl group, an alkoxycarbonylmethylcarbonyl group having a $C_{1-8}$ alkoxy group, an alkylsulfonylmethyl group having a $C_{1-8}$ alkyl group, a alkylsulfonyl group, phenylsulfonyl, a $C_{1-8}$ alkylaminosulfonyl group, and a five-membered or six-membered heteroaryl group.

(4) A compound of the formula (I) described in (A) or (3), or a pharmaceutically acceptable salt thereof, wherein Ar is phenyl, phenyl having a substituent, pyridyl, or pyridyl having a substituent, said substituent being $C_{1-8}$ alkylsulfonyl.

(5) A compound of the formula (I) described in (A) or (B), or a pharmaceutically acceptable salt thereof, wherein Ar is phenyl having two substituents or pyridyl having two substituents, one of said substituents being an alkylsulfonylmethyl group having a $C_{1-8}$ alkyl group or a $C_{1-8}$ alkylsulfonyl group, and the other being a $C_{1-8}$ alkyl group or a halogen atom.

(6) A compound of the formula (I) described in (A) or (B), or a pharmaceutically acceptable salt thereof, wherein Ar is phenyl having a substituent or pyridyl having a substituent, said substituent being 1-tetrazolyl.

(7) A compound of the formula (I) described in (A) or (B), or a pharmaceutically acceptable salt thereof, wherein Ar is phenyl having two substituents or pyridyl having two substituents, one of said substituents being 1-tetrazolyl, and the other being a $C_{1-8}$ alkyl group or a halogen atom.

(8) A compound of the formula (I) described in (A) or (B), (1)-(7), or a pharmaceutically acceptable salt thereof, wherein A is O, and B is $CH_2$.

(9) A compound of the formula (I) described in (A), (B), (1)-(7), or a pharmaceutically acceptable salt thereof, wherein A is $CH_2$, and B is O or NH.

(10) A compound of the formula (I) described in (A), (B), (1)-(7), or a pharmaceutically acceptable salt thereof, wherein A is $CH_2$, and B is $CH_2$.

(11) A compound of the formula (I) described in (A), (1)-(7), or a pharmaceutically acceptable salt thereof, wherein A is S, and B is $CH_2$.

(12) A compound of the formula (I) described in (A), (B), (1)-(11), or a pharmaceutically acceptable salt thereof, wherein one of U and V is N, and the other is CH.

(13) A compound of the formula (I) described in (A), (B), (1)-(11), or a pharmaceutically acceptable salt thereof, wherein each of U and V is N.

(14) A compound of the formula (I) described in (A), (B), (1)-(11), or a pharmaceutically acceptable salt thereof, wherein U is N, and V is CH.

(15) A compound of the formula (I) described in (A), (B), (1)-(14), or a pharmaceutically acceptable salt thereof, wherein each of X and Y is ethylene.

(16) A compound of the formula (I) described in (A), (B), (1)-(15), or a pharmaceutically acceptable salt thereof, wherein Z is $C(O)OR^7$.

(17) A compound of the formula (I) described in (16) or a pharmaceutically acceptable salt thereof, wherein $R^7$ is a $C_{1-8}$ alkyl group.

(18) A compound of the formula (I) described in (16) or a pharmaceutically acceptable salt thereof, wherein $R^7$ is a $C_{3-5}$ alkyl group.

(19) A compound of the formula (I) described in (A), (B), (1)-(15), or a pharmaceutically acceptable salt thereof, wherein Z is 3-$C_{1-8}$ alkyl-1,2,4-oxadiazol-5-yl or 5-$C_{1-8}$ alkyl-1,2,4-oxadiazol-3-yl.

(20) A compound of the formula (I) described in (A), (B), (1)-(15), or a pharmaceutically acceptable salt thereof, wherein Z is 5-$C_{1-8}$ alkylpyrimidin-2-yl.

(21) A compound of the formula (I) described in (A), (B), (1)-(20), or a pharmaceutically acceptable salt thereof, wherein each of $R^1$ and $R^2$ is hydrogen.

(22) A compound of the formula (I) described in (A), (B), (1)-(20), or a pharmaceutically acceptable salt thereof, wherein $R^1$ is a $C_{1-8}$ alkyl group, and $R^2$ is hydrogen.

(23) A compound of the formula (I) described in (A), (B), (1)-(20), or a pharmaceutically acceptable salt thereof, wherein $R^1$ is a halogen atom, and $R^2$ is hydrogen.

Preferred embodiments of the cyclic amine derivative of the formula (II) described in (C) or (D) are shown below.

(24) A cyclic amine derivative of the formula (II) described in (C), (D), or a pharmaceutically acceptable salt thereof, wherein $Ar^0$ is phenyl, which optionally has a substituent selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $CH_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, phenylsulfonyl, and a five-membered or six-membered heteroaryl group.

(25) A cyclic amine derivative of the formula (II) described in (C), (D), or a pharmaceutically acceptable salt thereof, wherein $Ar^0$ is pyridyl, which optionally has a substituent selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, phenylsulfonyl, and a five-membered or six-membered heteroaryl group.

(26) A cyclic amine derivative of the formula (II) described in (C), (D), or a pharmaceutically acceptable salt thereof, wherein $Ar^0$ is phenyl having only one substituent or pyridyl having only one substituent, said substituent being selected from the group consisting of an alkoxycarbonyl group having a $C_{1-8}$ alkoxy group, an alkylaminocarbonyl group having a $C_{1-8}$ alkyl group, an alkoxycarbonylmethylcarbonyl group having a $C_{1-8}$ alkoxy group, an alkylsulfonylmethyl group having a $C_{1-8}$ alkyl group, a $C_{1-8}$ alkylsulfonyl group, phenylsulfonyl, a $C_{1-8}$ alkylaminosulfonyl group, and a five-membered or six-membered heteroaryl group.

(27) A cyclic amine derivative of the formula (II) described in (C), (D), or a pharmaceutically acceptable salt thereof, wherein $Ar^0$ is phenyl, phenyl having a substituent, pyridyl, or pyridyl having a substituent, said substituent being a $C_{1-8}$ alkylsulfonyl group.

(28) A cyclic amine derivative of the formula (II) described in (C), (D), or a pharmaceutically acceptable salt thereof, wherein $Ar^0$ is phenyl having two substituents or pyridyl having two substituents, one of said substituents being an alkylsulfonylmethyl group having a $C_{1-8}$ alkyl group or a $C_{1-8}$ alkylsulfonyl group, and the other being a $C_{1-8}$ alkyl group or a halogen atom.

(29) A cyclic amine derivative of the formula (II) described in (C), (D), or a pharmaceutically acceptable salt thereof, wherein $Ar^0$ is phenyl having a substituent or pyridyl having a substituent, said substituent being 1-tetrazolyl.

(30) A cyclic amine derivative of the formula (II) described in (C), (D), or a pharmaceutically acceptable salt thereof, wherein $Ar^0$ is phenyl having two substituents or pyridyl having two substituents, one of said substituents being 1-tetrazolyl, and the other being a $C_{1-8}$ alkyl group or a halogen atom.

(31) A cyclic amine derivative of the formula (II) described in (C), (D), (24)-(30), or a pharmaceutically acceptable salt thereof, wherein $A^0$ is O, and $B^0$ is $CH_2$.

(32) A cyclic amine derivative of the formula (II) described in (C), (D), (24)-(30), or a pharmaceutically acceptable salt thereof, wherein $A^0$ is $CH_2$, and $B^0$ is O or NH.

(33) A cyclic amine derivative of the formula (II) described in (C), (D), (24)-(30), or a pharmaceutically acceptable salt thereof, wherein $A^0$ is $CH_2$, and $B^0$ is $CH_2$.

(34) A cyclic amine derivative of the formula (II) described in (C), (24)-(30), or a pharmaceutically acceptable salt thereof, wherein $A^0$ is S, and $B^0$ is $CH_2$.

(35) A cyclic amine derivative of the formula (II) described in (C), (D), (24)-(34), or a pharmaceutically acceptable salt thereof, wherein one of $U^0$ and $V^0$ is N, and the other is CH.

(36) A cyclic amine derivative of the formula (II) described in (C), (D), (24)-(34), or a pharmaceutically acceptable salt thereof, wherein each of $U^0$ and $V^0$ is N.

(37) A cyclic amine derivative of the formula (II) described in (C), (D), (24)-(34), or a pharmaceutically acceptable salt thereof, wherein $U^0$ is N, and $V^0$ is CH.

(38) A cyclic amine derivative of the formula (II) described in (C), (D), (24)-(37), or a pharmaceutically acceptable salt thereof, wherein each of $X^0$ and $Y^0$ is ethylene.

(39) A cyclic amine derivative of the formula (II) described in (C), (O), (24)-(38), or a pharmaceutically acceptable salt thereof, wherein $R^{23}$ is a $C_{1-8}$ alkyl group.

(40) A cyclic amine derivative of the formula (II) described in (C), (D), (24)-(38), or a pharmaceutically acceptable salt thereof, wherein $R^{23}$ is a $C_{3-5}$ alkyl group.

(41) A cyclic amine derivative of the formula (II) described in (C), (D), (24)-(40), or a pharmaceutically acceptable salt thereof, wherein each of $R^{21}$ and $R^{22}$ is hydrogen.

(42) A cyclic amine derivative of the formula (II) described in (C), (D), (24)-(40), or a pharmaceutically acceptable salt thereof, wherein $R^{21}$ is a $C_{1-8}$ alkyl group, and $R^{22}$ is hydrogen.

(43) A cyclic amine derivative of the formula (II) described in (C), (D), (24)-(40), or a pharmaceutically acceptable salt thereof, wherein $R^{21}$ is a halogen atom, and $R^{22}$ is hydrogen.

In the compound of the formula (I) described in (A) or (B), or the cyclic amine derivative of the formula (II) described in (C) or (D), examples of the halogen atoms include a fluorine atom, a chlorine atom, and a bromine atom. Examples of the $C_{1-8}$ alkyl groups include methyl, ethyl, propyl, isopropyl, butyl, t-butyl, pentyl, neopentyl, and hexyl. Examples of the $C_{2-8}$ alkenyl groups include 2-propenyl and 3-methyl-2-butenyl. Examples of the $C_{3-8}$ cycloalkyl groups include cyclopropyl, cyclopentyl, and cyclohexyl. Examples of the $C_{1-8}$ alkyl groups having phenyl include benzyl and phenethyl. Examples of the $C_{1-8}$ alkoxy groups include methoxy, ethoxy, and propoxy. Examples of the $C_{1-8}$ alkyl groups having one to three halogen atoms include chloromethyl, fluoromethyl, 2-fluoroethyl, and trifluoromethyl. Examples of the $C_{1-8}$ alkoxy groups having one to three halogen atoms include fluoromethoxy and trifluoromethoxy. Examples of the alkoxycarbonyl groups having a $C_{1-8}$ alkoxy group include methoxycarbonyl and ethoxycarbonyl. Examples of the acyl groups having a $C_{1-8}$ alkyl group include acetyl. Examples of the alkylaminocarbonyl groups having a $C_{1-8}$ alkyl group include methylaminocarbonyl and ethylaminocarbonyl. Examples of the dialkylaminocarbonyl groups having $C_{2-12}$ alkyl groups include dimethylaminocarbonyl and diethylaminocarbonyl. Examples of the alkoxycarbonylmethylcarbonyl groups having a $C_{1-8}$ alkoxy group include methoxycarbonylmethylcarbonyl and ethoxycarbonylmethylcarbonyl. Examples of the alkylsulfonylmethyl groups having a $C_{1-8}$ alkyl group include methanesulfonylmethyl and ethanesulfonylmethyl. Examples of the $C_{1-8}$ alkylamino groups include methylamino and ethylamino. Examples of the $C_{2-12}$ dialkylamino groups include dimethylamino and diethylamino. Examples of the $C_{1-8}$ alkylsulfonylamino groups include methanesulfonylamino and ethanesulfonylamino. Examples of the acylamino groups having a $C_{1-8}$ alkyl group include acetylamino. Examples of the $C_{1-8}$ alkylsulfinyl groups include methanesulfinyl and ethanesulfinyl. Examples of the $C_{1-8}$ alkylsulfonyl groups include methanesulfonyl and ethanesulfonyl. Examples of the $C_{1-8}$ alkylaminosulfonyl groups include methylaminosulfonyl and ethylaminosulfonyl. Examples of the $C_{2-12}$ dialkylaminosulfonyl groups include dimethylaminosulfonyl. Examples of the aryl groups include phenyl and naphthyl.

In the formula (I) described in (A) or (B), examples of the five-membered or six-membered heteroaryl groups of Ar, which optionally has a substituent, include pyridyl.

In the formula (I) described in (A) or (B), examples of the five-membered or six-membered heteroaryl groups of Z include 1,2,4-oxadiazolyl and pyrimidinyl.

In the formula (I) described in (A) or (B), examples of the five-membered or six-membered heteroaryl groups of the substituent for the aryl or five-membered or six-membered heteroaryl group of Ar include tetrazolyl and 1,2,4-triazolyl.

In the formula (II) described in (C) or (D), examples of the five-membered or six-membered heteroaryl groups of the substituent for phenyl or pyridyl of $Ar^0$ include tetrazolyl and 1,2,4-triazolyl.

The compound of the formula (I) described in (A) or (B), or the cyclic amine derivative of the formula (II) described in (C) or (D) can form a pharmaceutically acceptable salt with an organic or inorganic acid such as hydrochloric acid, sulfuric acid, fumaric acid, and oxalic acid.

The compound of the formula (I) described in (A) or (B), or the cyclic amine derivative of the formula (II) described in (C) or (D) include geometrical isomer such as cis and trans isomer, racemic mixture, and enantiomer (optically active isomer).

The compound of the formula (I) described in (A) or (B), or the cyclic amine derivative of the formula (II) described in (C) or (D) include a hydrate and a solvate.

The process for preparation of the compound of the formula (I) described in (A) or (B), the cyclic amine derivative of the formula (II) described in (C) or (D), or a pharmaceutically acceptable salt thereof is described below.

The following examples show the process for preparation of the compound of the formula (I) described in (A) or (B) in which A is O, each of X and Y is $CH_2CH_2$. The other compounds can also be prepared according to analogous processes.

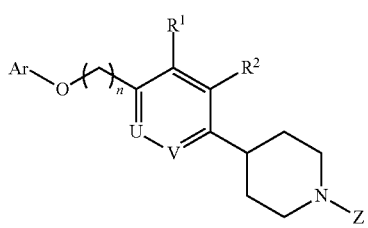

<Method A>
(First Process)

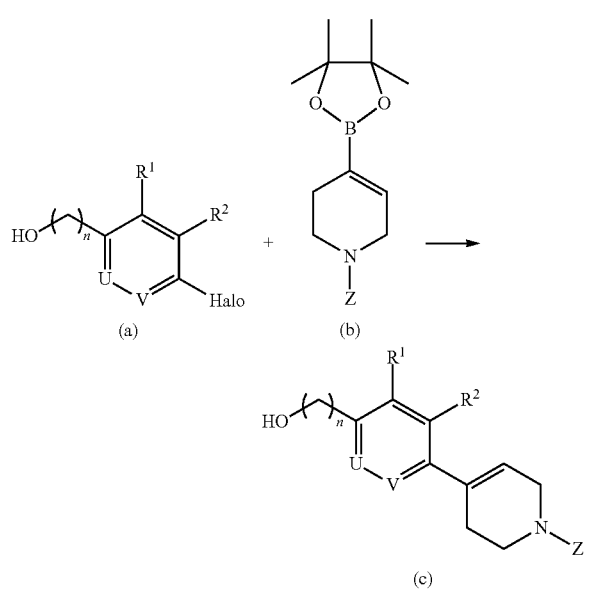

(Second Process)

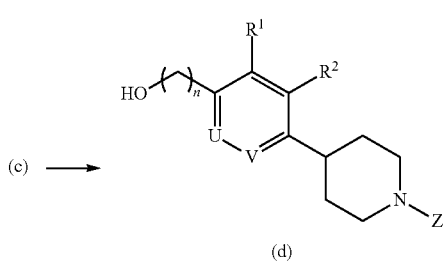

(Third Process)

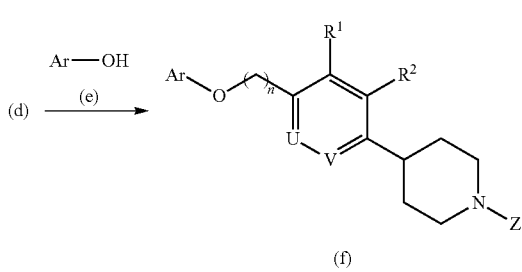

In the formulas, Halo is halogen such as chlorine, bromine and iodine, and each of $R^1$, $R^2$, U, V, Z and Ar are described above.

1) Starting Materials

The starting material (a) can be synthesized according to a known method (cf., M. V. Chelliah et al., J. Med. Chem., 2007, 50, 5147; and WO 2006/114213) or an analogous method thereof. The starting material (b) can also be synthesized according to a known method (cf., D. J. Wustrow et al., Synthesis, 1991, 993) or an analogous method thereof.

2) First Process

The condensation reaction of the starting material (a) with the starting material (b) can be conducted in an inert solvent such as toluene, tetrahydrofuran, dioxane and N,N-dimethylformamide, in the presence of a base such as potassium carbonate, cesium carbonate and sodium carbonate, using a catalyst such as tetrakis(triphenylphosphine)palladium and [1,1'-bis(diphenylphosphino)-ferrocene]palladium(II) dichloride dichloromethane complex, to give the compound of the formula (c). The reaction temperature is in the range from 20 to 110° C.

3) Second Process

The compound of the formula (c) can be converted into the compound of the formula (d) in an inert solvent such as methanol and ethanol, in the presence of a catalyst such as palladium-carbon according to a catalytic hydrogenation method.

4) Third Process

The compound of the formula (d) can be converted into the compound of the formula (f) by a reaction of the compound (d) with the compound of the formula (e) such as phenol and heteroaryl alcohol, in an inert solvent such as tetrahydrofuran, dioxane and toluene, in the presence of an azodicarboxylic ester such as diisopropyl azodicarboxylate and diethyl azodicarboxylate, and a phosphine such as triphenylphosphine. The reaction temperature is in the range from 0 to 80° C.

The intermediate of the formula (d) can also be synthesized according to the following method B or C.

<Method B>
(First Process)

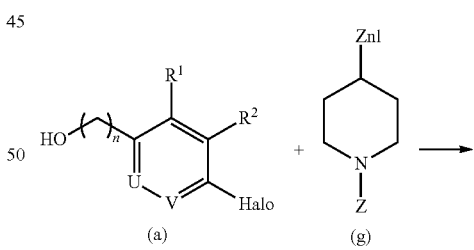

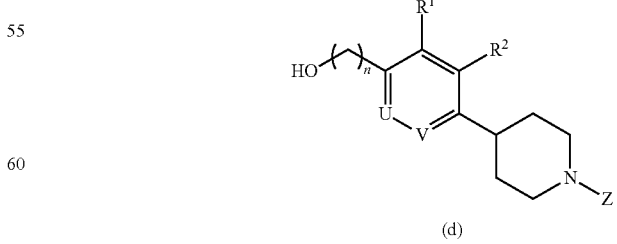

In the formulas, Halo is halogen such as chlorine, bromine and iodine, and each of $R^1$, $R^2$, U, V and Z are described above.

1) Starting Material

The starting material (g) can be synthesized according to a known method (cf., S., Billotte, Synlett, 1998, 379) or an analogous method thereof.

2) First Process

The condensation reaction of the starting material (a) with the starting material (g) can be conducted in an inert solvent such as toluene, tetrahydrofuran and N,N-dimethylformamide, optionally in the presence of an additive such as tri(2-furyl)phosphine, using a catalyst such as tris(dibenzylideneacetone)palladium and tetrakis(triphenylphosphine)palladium, to give the compound of the formula (d). The reaction temperature is in the range from 20 to 110° C.

<Method C>

(First Process)

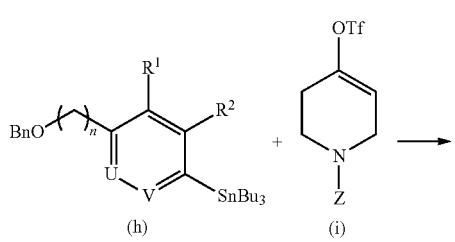

(Second Process)

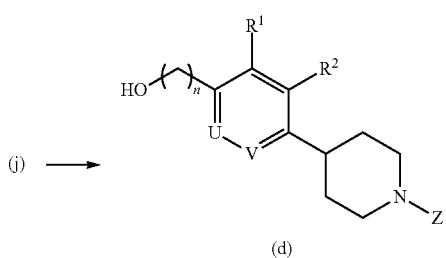

In the formulas, each of $R^1$, $R^2$, U, V and Z are described above.

1) Starting Materials

The starting material (h) can be synthesized according to a known method (cf., H. Azizian et al., J. Organomet. Chem., 1981, 215, 49; and C. Eaborn et al., J. Chem. Soc., 1962, 1131) or an analogous method thereof. The starting material (i) can also be synthesized according to a known method (cf., D. J. Wustrow et al., Synthesis, 1991, 993) or an analogous method thereof.

2) First Process

The condensation reaction of the starting material (h) with the starting material (i) can be conducted in an inert solvent such as toluene, tetrahydrofuran and N,N-dimethylformamide, using a catalyst such as tetrakis(triphenylphosphine)palladium and tris(dibenzylideneacetone)-palladium, to give the compound of the formula (d). The reaction temperature is in the range from 20 to 110° C.

3) Second Process

The compound of the formula (j) can be converted into the compound of the formula (d) in the same manner as in the above-mentioned method A.

The compound of the formula (d) can also be converted into the compound of the formula (f) according to the following method D.

<Method D>

(First Process)

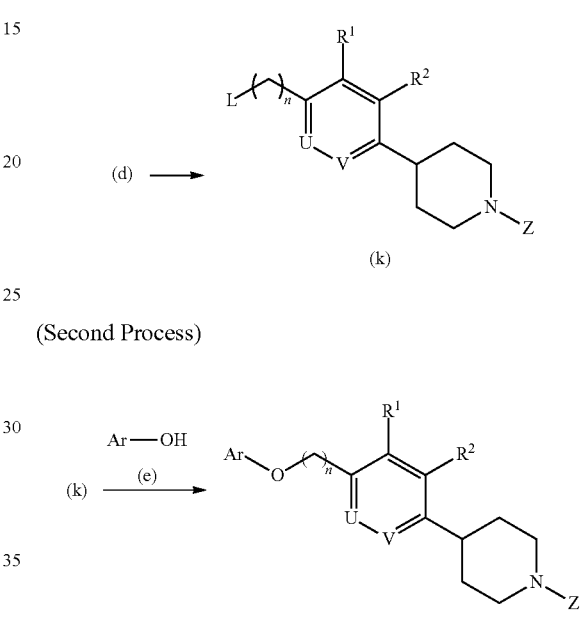

(Second Process)

In the formulas, L is a halogen atom such as chlorine atom, bromine atom, iodine atom or a leaving group such as methanesulfonyloxy and p-toluenesulfonyloxy, and each of $R^1$, $R^2$, U, V, Z and Ar are described above.

1) First Process

The compound of the formula (d) can be converted into the compound of the formula (k) by a reaction of the compound (d) with a reagent such as methanesulfonyl chloride, p-toluenesulfonyl chloride and thionyl chloride, in an inert solvent such as toluene and dichloromethane, optionally in the presence of a base such as pyridine and triethylamine.

3) Second Process

The compound of the formula (k) can be converted into the compound of the formula (f) by a reaction of the compound (k) with a phenol or a heteroaryl alcohol represented by the formula (e) in an inert solvent such as N,N-dimethylformamide and acetone, in the presence of a base such as sodium hydride and potassium carbonate. The reaction temperature is in the range from 0 to 80° C.

The compound of the formula (n), which is a compound of the present invention and is an intermediate in preparation of the compound represented by the formula (f), can also be prepared according to the following method E.

<Method E>
(First Process)

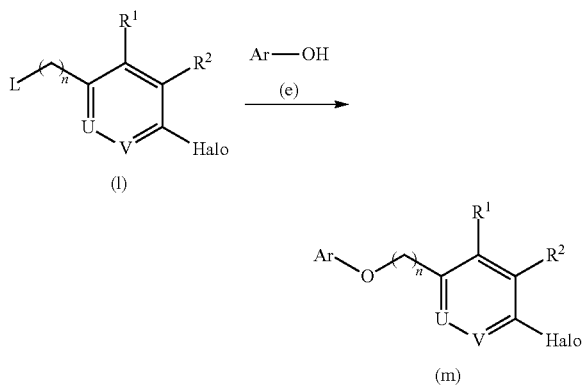

(Second Process)

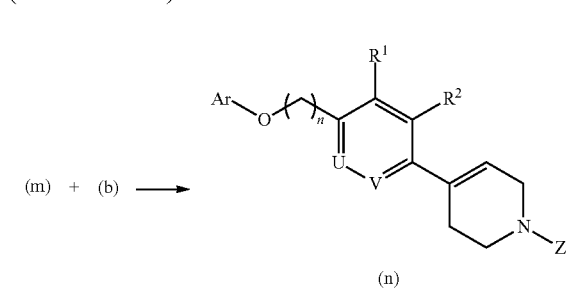

(Third Process)

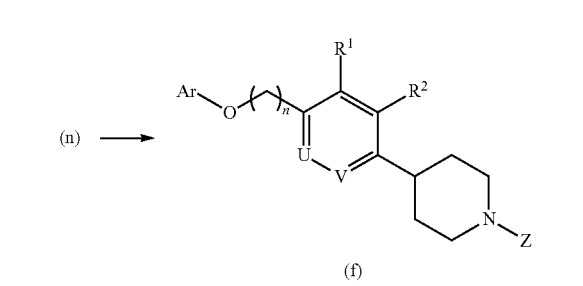

In the formulas, L is a halogen atom such as chlorine atom, bromine atom, iodine atom or a leaving group such as methanesulfonyloxy and p-toluenesulfonyloxy, and each of $R^1$, $R^2$, U, V, Z and Ar are described above.

1) Starting Material

The starting material (1) can be synthesized according to a known method (cf., SP 1555259) or an analogous method thereof.

2) First Process

The starting material (1) can be converted into the compound of the formula (m) in the same manner as in the above-mentioned method D.

3) Second Process

The compound of the formula (m) can be converted into the compound of the formula (n) in the same manner as in the above-mentioned method A.

4) Third Process

The compound of the formula (n) can be converted into the compound of the formula (f) in the same manner as in the above-mentioned method A.

The following examples show the process for preparation of the compound of the formula (I) described in (A) or (B) in which B is O or NH, each of X and Y is $CH_2CH_2$. The other compounds can also be prepared according to analogous processes.

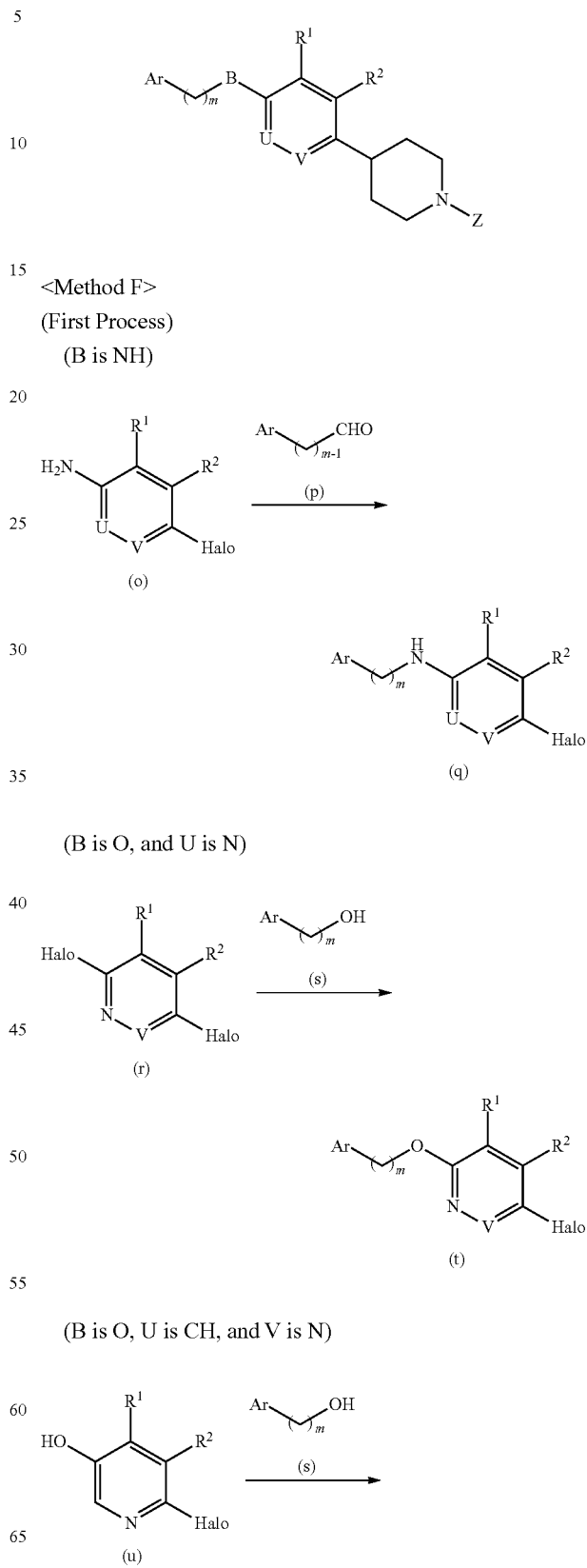

-continued

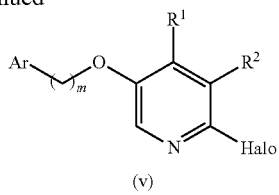

(v)

(Second Process)

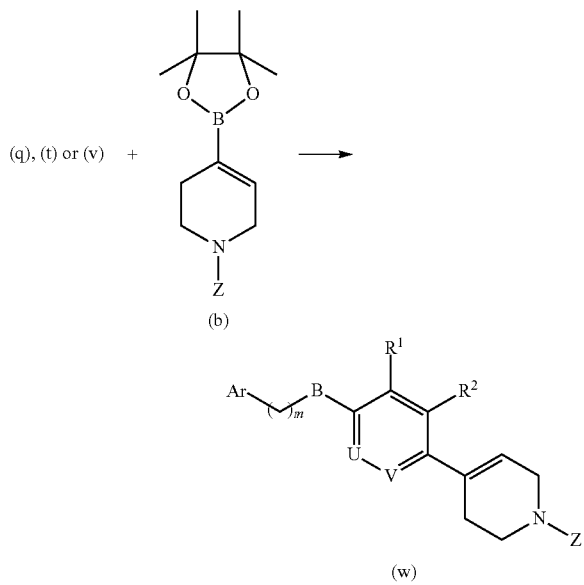

(Third Process)

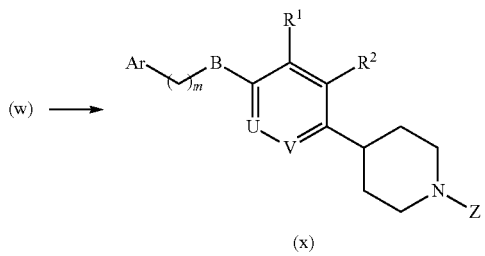

(x)

In the formulas, Halo is halogen such as chlorine, bromine and iodine, and each of Ar, B, $R^1$, $R^2$, U, V and Z are described above.

1) First Process (B is NH)

The compound of the formula (o) can be converted into the compound of the formula (q) by a condensation of the compound (o) with the aldehyde of the formula (p) in an inert solvent such as tetrahydrofuran and acetonitrile, optionally in the presence of an acid catalyst such as acetic acid and trifluoroacetic acid, and a subsequent reaction of the resulting compound with a reagent such as triethylsilane. The reaction temperature is in the range from 20 to 80° C.

(B is O, and U is N)

The compound of the formula (r) can be converted into the compound of the formula (t) by a reaction of the compound (r) with the alcohol of the formula (s) in an inert solvent such as tetrahydrofuran, toluene, and dichloromethane, in the presence of a base such as potassium tert-butoxide and sodium hydride. The reaction temperature is in the range from −20 to 110° C.

(B is O, U is CH, and V is N)

The compound of the formula (u) can be converted into the compound of the formula (v) by a reaction of the compound (u) with the alcohol of the formula (s) in an inert solvent such as tetrahydrofuran, dioxane, and toluene, in the presence of an azodicarboxylic ester such as diethyl azodicarboxylate and diisopropyl azodicarboxylate, and a phosphine such as triphenylphosphine. The reaction temperature is in the range from 0 to 80° C.

2) Second Process

The compound of the formula (q), (t) or (v) can be condensed with the starting material (b) in the same manner as in the above-mentioned method A.

3) Third Process

The compound of the formula (w) can be converted into the compound of the formula (x) in an inert solvent such as methanol and ethanol, in the presence of a catalyst such as platinum-carbon and palladium-carbon, according to a catalytic hydrogenation method.

The compound of the formula (I) described in (A) or (B) in which B is NH can also be synthesized according to the following method G.

<Method G>

(First Process)

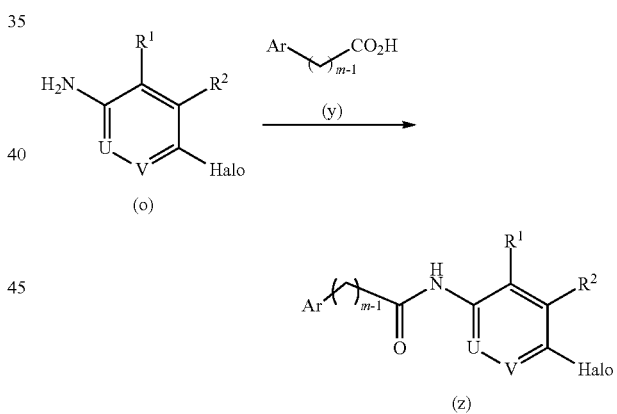

(Second Process)

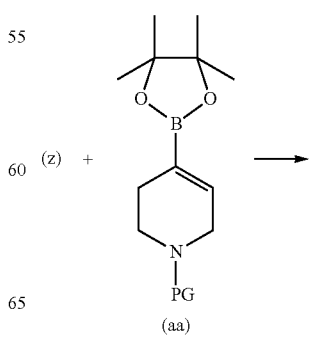

(aa)

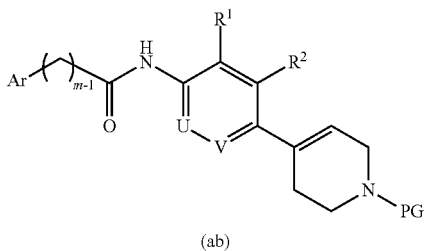

(ab)

(Third Process)

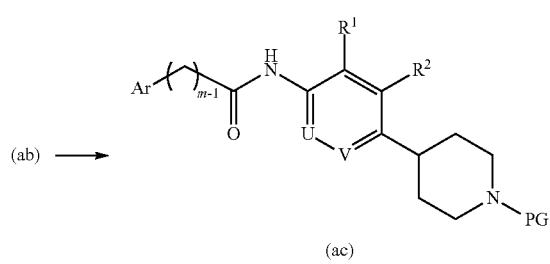

(ab) →

(ac)

(Fourth Process)

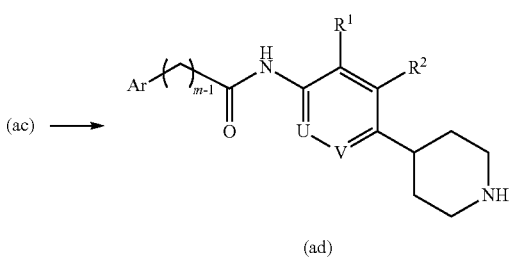

(ac) →

(ad)

(Fifth Process)

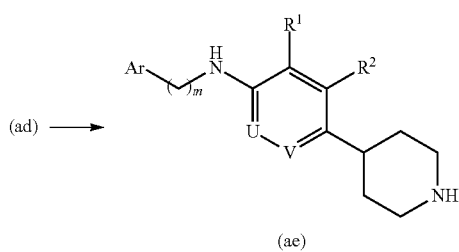

(ad) →

(ae)

(Sixth Process)

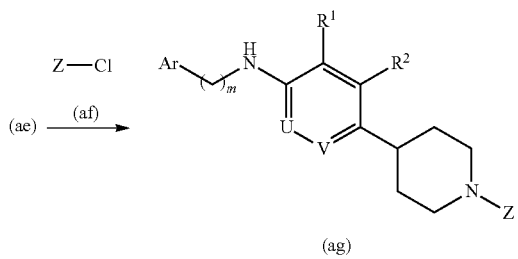

(ae) $\xrightarrow{\text{Z—Cl}}_{\text{(af)}}$ (ag)

In the formulas, Halo is halogen such as chlorine, bromine and iodine, PG is a protective group such as tert-butoxycarbonyl and benzyl, and each of Ar, $F^1$, $R^2$, O, V and Z are described above.

1) First Process

The compound of the formula (o) can be converted into the compound of the formula (z) by a condensation of the compound (o) with the carboxylic acid of the formula (y) in an inert solvent such as N,N-dimethylformamide and dichloromethane, in the presence of a base such as N-methylmorpholine and triethylamine, a condensing agent such as 1-ethyl-3-(3-dimethylaminopropyl)carbodiimide hydrochloride (WSC-HCl), and an additive such as 1-hydroxybenzotriazole. The reaction temperature is in the range from 0 to 20° C.

2) Second Process

The compound of the formula (z) can be condensed with the starting material (aa) in the same manner as in the above-mentioned method A.

3) Third Process

The compound of the formula (ab) can be converted into the compound of the formula (ac) in the same manner as in the above-mentioned method A.

4) Fourth Process

The protective group (PG) for amine can be cleaved from the compound of the formula (ac) according to a conventional method. When the protective group is tert-butoxycarbonyl, the group can be cleaved by a reaction of an acid such as trifluoroacetic acid, optionally in an inert solvent such as dichloromethane.

5) Fifth Process

The compound of the formula (ad) can be converted into the compound of the formula (ae) using a reducing agent such as lithium aluminum hydride, sodium bis(2-methoxyethoxy) aluminum hydride and diborane, in an inert solvent such as tetrahydrofuran and toluene.

6) Sixth Process

The compound of the formula (ae) can be converted into the compound of the formula (ag) by a reaction of the compound (ae) with the acid chloride of the formula (af) in an inert solvent such as dichloromethane, tetrahydrofuran and toluene, in the presence of a base such as triethylamine and pyridine. The reaction temperature is in the range from 0 to 50° C.

Examples of the representative compounds of the present invention are shown below.

Representative Compound (1)

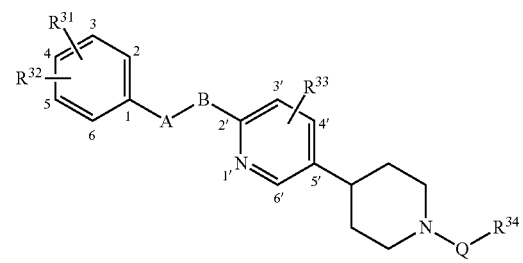

In the formula, $R^{31}$, $R^{32}$, $R^{33}$, A, B, Q and $R^{34}$ are set forth in Tables 1 to 5.

TABLE 1

| $R^{31}$ | $R^{32}$ | $R^{33}$ | A | B | Q | $R^{34}$ |
|---|---|---|---|---|---|---|
| 4-$CO_2C_2H_5$ | — | 3'-$CH_3$ | O | $CH_2$ | C(O)O | Isopropyl |
| 3-$CH_3$ | 4-CN | — | $CH_2$ | O | C(O)O | $C_2H_5$ |
| 4-$SO_2CH_3$ | — | — | O | $CH_2$ | C(O)O | t-Butyl |
| 2-$CH_3$ | 4-$SO_2CH_3$ | — | O | $CH_2$ | C(O) | $CH_2C(CH_3)_3$ |
| 4-$CF_3$ | — | — | O | $CH_2$ | $CH_2C(O)NH$ | $CH_3$ |
| 4-S(O)$CH_3$ | — | — | O | $CH_2$ | C(O)NH | Isopropyl |
| 3-F | 4-$SO_2CH_3$ | — | $CH_2$ | $NC_2H_5$ | C(O)O | Cyclopro* |
| 4-$SO_2NH_2$ | — | — | O | $CH_2$ | C(O)O | Isopropyl |

(Remark)
Cyclopro*: Cyclopropyl

TABLE 2

| $R^{31}$ | $R^{32}$ | $R^{33}$ | A | B | Q | $R^{34}$ |
|---|---|---|---|---|---|---|
| 4-$NHSO_2CH_3$ | — | 4'-$CH_3$ | O | $CH_2$ | C(O)O | t-Butyl |
| 4-$CH_2SO_2CH_3$ | — | — | $CH_2$ | NH | $S(O)_2$ | Cyclohexyl |
| 4-$N(CH_3)_2$ | — | — | $CH_2CH_2$ | O | C(O)O | n-Butyl |
| 2-F | 4-$SO_2CH_3$ | — | NH | $CH_2$ | C(O)O | t-Butyl |
| 4-$SO_2NHC_2H_5$ | — | 6'-$CH_3$ | O | $CH_2$ | C(O)O | $CH_3$ |
| 4-$SO_2CH_3$ | — | — | $CH_2$ | NH | C(O)O | t-Butyl |

TABLE 3

| $R^{31}$ | $R^{32}$ | $R^{33}$ | A | B | Q | $R^{34}$ |
|---|---|---|---|---|---|---|
| 2-$COCH_3$ | 4-$CO_2H$ | — | O | $CH_2CH_2$ | C(O)O | Benzyl |
| 4-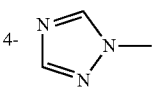 | — | — | O | $CH_2$ | 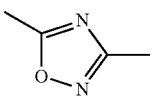 | Isopropyl |
| 4-$SO_2C_2H_5$ | — | — | O | $CH_2$ | 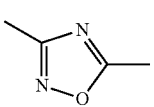 | Ethyl |
| 2-$CF_3$ | 4-$SO_2CH_3$ | — | O | $CH_2$ | C(O) | Phenyl |

TABLE 4

| $R^{31}$ | $R^{32}$ | $R^{33}$ | A | B | Q | $R^{34}$ |
|---|---|---|---|---|---|---|
| 4-Phenoxy | — | — | $NCH_3$ | $CH_2$ | C(O)O | Phenethyl |
| 3-$OC_2H_5$ | — | — | $CH_2$ | $CH_2$ | C(O)O | t-Butyl |
| 4-Br | — | 3'-Cl | Bond | O | C(O)O | $CH_2CH=CH_2$ |
| 4-$NO_2$ | — | — | O | $CH_2$ | C(O)NH | Isopropyl |
| 4-$SO_2$-Phenyl | — | — | O | $CH_2$ | C(O)O | $(CH_2)_5CH_3$ |
| 4-$CONHCH_3$ | — | — | O | $CH_2$ | C(O)O | t-Butyl |
| 4-$COCH_2CO_2CH_3$ | — | — | O | $CH_2$ | C(O) | $CH_2CH=C(CH_3)_2$ |

TABLE 5

| $R^{31}$ | $R^{32}$ | $R^{33}$ | A | B | Q | $R^{34}$ |
|---|---|---|---|---|---|---|
| 2-$CH_3$ | 4-$SO_2CH_3$ | 3'-Cl | O | $CH_2$ | C(O)O | t-Butyl |
| 2-Br | 4-$SO_2CH_3$ | 3'-$CF_3$ | O | $CH_2$ | C(O)O | Isopropyl |
| 2-Cl | 4-$SO_2CH_3$ | — | S | $CH_2$ | C(O)O | Isopentyl |

TABLE 5-continued

| $R^{31}$ | $R^{32}$ | $R^{33}$ | A | B | Q | $R^{34}$ |
|---|---|---|---|---|---|---|
| 2-F | 4-(1,2,4-triazol-1-yl) | 3'-Cl | O | $CH_2$ | C(O)O | t-Butyl |
| 2-F | 4-$SO_2CH_3$ | — | $CH_2$ | $CH_2$ | C(O)O | t-Butyl |
| 2-F | 4-$SO_2CH_3$ | 3'-$CH_3$ | O | $CH_2$ | 2,5-pyrimidinyl | $C_2H_5$ |
| 3-Cl | 4-$SO_2CH_3$ | — | O | $CH_2$ | C(O)O | t-Butyl |
| 3-$CH_3$ | 4-$SO_2CH_3$ | 3'-F | O | $CH_2$ | C(O)O | t-Butyl |
| 2-F | 4-$SO_2CH_3$ | 3'-F | O | $CH_2$ | 3,5-(1,2,4-oxadiazolyl) | Isopropyl |

Representative Compound (2)

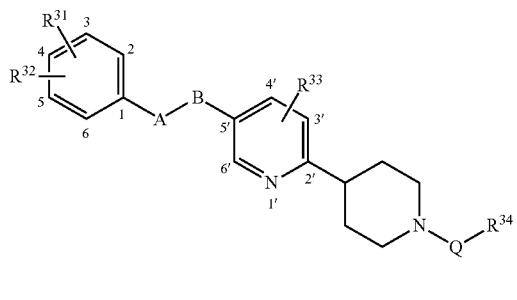

In the formula, $R^{31}$, $R^{32}$, $R^{33}$, A, B, Q and $R^{34}$ are set forth in Tables 6 to 8.

TABLE 6

| $R^{31}$ | $R^{32}$ | $R^{33}$ | A | B | Q | $R^{34}$ |
|---|---|---|---|---|---|---|
| 4-CN | — | 4'-$CH_3$ | O | $CH_2$ | C(O)O | $C_2H_5$ |
| 2-F | — | — | $CH_2$ | O | $S(O)_2$ | n-Propyl |
| 4-$SO_2CH_3$ | — | — | O | $CH_2$ | C(O)O | t-Butyl |
| 2-$CH_3$ | 4-$SO_2C_2H_5$ | — | $CH_2$ | NH | C(O)O | Isopropyl |
| 4-$S(O)CH_3$ | — | — | NH | $CH_2$ | C(O)O | $CH_3$ |
| 4-$SO_2NH_2$ | — | — | O | $CH_2$ | — | Cyclopropyl |

TABLE 7

| $R^{31}$ | $R^{32}$ | $R^{33}$ | A | B | Q | $R^{34}$ |
|---|---|---|---|---|---|---|
| 4-$NHSO_2CH_3$ | — | — | $CH_2$ | O | C(O)O | Isopropyl |
| 2-F | 4-$SO_2CH_3$ | 6'-$CH_3$ | NH | $CH_2$ | C(O)O | Cyclopentyl |
| 3-Br | — | — | O | $CH_2$ | C(O)O | Isopropyl |
| 4-$CH_2SO_2CH_3$ | — | — | O | $CH_2$ | C(O)O | t-Butyl |
| 4-(1,2,4-triazol-1-yl) | — | — | O | $CH_2$ | C(O)O | t-Butyl |

TABLE 8

| $R^{31}$ | $R^{32}$ | $R^{33}$ | A | B | Q | $R^{35}$ |
|---|---|---|---|---|---|---|
| 4-$SO_2CH_3$ | — | 3'-$CH_3$ | $CH_2$ | O | 3,5-(1,2,4-oxadiazolyl) | Isopropyl |
| 4-$COCH_2CO_2C_2H_5$ | — | — | O | $CH_2$ | C(O) | $CH_2C(CH_3)_3$ |
| 4-$SO_2NHC_2H_5$ | — | — | O | $CH_2$ | 3,5-(1,2,4-oxadiazolyl) | Isopropyl |

Representative Compound (3)

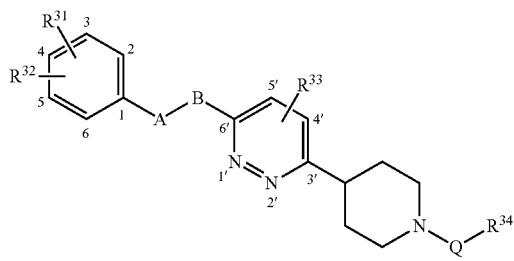

In the formula, $R^{31}$, $R^{32}$, $R^{33}$, A, B, Q and $R^{34}$ are set forth in Tables 9 and 10.

Representative Compound (4)

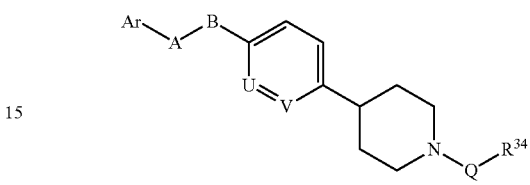

In the formula, Ar, A, B, U, V, Q and $R^{34}$ are set forth in Tables 11 and 12.

TABLE 10-continued

| $R^{31}$ | $R^{32}$ | $R^{33}$ | A | B | Q | $R^{34}$ |
|---|---|---|---|---|---|---|
| 4-SO$_2$NHC$_2$H$_5$ | — | — | O | CH$_2$ | 3,5-dimethyl-1,2,4-oxadiazol-yl | Isopropyl |

TABLE 11

| Ar | A | B | U | V | Q | $R^{34}$ |
|---|---|---|---|---|---|---|
| H$_3$CO$_2$S-pyridyl | O | CH$_2$ | N | CH | C(O)O | Isopropyl |
| H$_3$CO$_2$S-(CH$_3$)pyridyl | O | CH$_2$ | N | CH | C(O)O | t-Butyl |
| H$_3$CO$_2$S-pyridyl | CH$_2$ | O | CH | N | C(O)O | t-Butyl |
| 4-pyridyl | CH$_2$ | NH | CH | N | 3,5-dimethyl-1,2,4-oxadiazol-yl | Isopropyl |

TABLE 9

| $R^{31}$ | $R^{32}$ | $R^{33}$ | A | B | Q | $R^{34}$ |
|---|---|---|---|---|---|---|
| 2-F | 4-SO$_2$CH$_3$ | — | O | CH$_2$ | C(O)O | Isopropyl |
| 3-NHCOCH$_3$ | — | — | O | CH$_2$ | C(O) | n-Butyl |
| 4-SO$_2$CH$_3$ | — | — | O | CH$_2$ | C(O)O | t-Butyl |
| 2-CON(CH$_3$)$_2$ | — | — | CH$_2$ | O | C(O)O | Isopropyl |
| 3-CO$_2$-isopropyl | — | — | NH | CH$_2$ | C(O)O | CH$_3$ |
| 4-SO$_2$NH$_2$ | — | — | O | CH$_2$ | C(O)O | Cyclopropyl |

TABLE 10

| $R^{31}$ | $R^{32}$ | $R^{33}$ | A | B | Q | $R^{34}$ |
|---|---|---|---|---|---|---|
| 4-(1,2,4-triazol-1-yl) | — | — | O | CH$_2$ | C(O)O | t-Butyl |
| 4-COCH$_2$CO$_2$C$_2$H$_5$ | — | — | O | NH | C(O) | C$_2$H$_5$ |

TABLE 12

| Ar | A | B | U | V | Q | $R^{34}$ |
|---|---|---|---|---|---|---|
| 1,2,4-triazol-1-yl-(CH$_3$)pyridyl | O | CH$_2$ | N | CH | C(O)O | Iso-propyl |
| H$_3$CO$_2$S-(CH$_3$)pyridyl | O | CH$_2$ | N | N | C(O)O | Iso-propyl |
| 1,2,4-triazol-1-yl-(CH$_3$)pyridyl | CH$_2$ | O | N | N | C(O)O | t-Butyl |

Representative Compound (5)

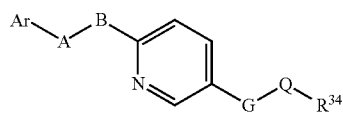

In the formula, Ar, A, B, G, Q and $R^{34}$ are set forth in Tables 13 and 14.

In the formula, $R^{32}$, $R^{35}$, $R^{33}$, A, B, Q and $R^{34}$ are set forth in Table 15.

TABLE 15

| $R^{33}$ | $R^{35}$ | $R^{32}$ | A | B | Q | $R^{34}$ |
|---|---|---|---|---|---|---|
| 3'-Cl | 2-F | 3-F | O | $CH_2$ | C(O)O | t-Butyl |
| — | 2-F | 5-F | O | $CH_2$ | C(O)O | Isopropyl |
| 3'-$CH_3$ | 2-$CH_3$ | 3-$CH_3$ | O | $CH_2$ | C(O)O | t-Butyl |

TABLE 13

| Ar | A | B | G | Q | $R^{34}$ |
|---|---|---|---|---|---|
| $H_3CO_2S$-(pyridyl with 2,3-di-CH₃) | O | $CH_2$ | 3-methyl-pyrrolidinyl | C(O)O | Isopropyl |
| $H_3CO_2S$-phenyl | O | $CH_2$ | 3-methyl-piperidinyl | C(O)O | t-Butyl |
| $H_3CO_2S$-phenyl-F | O | $CH_2$ | 4-methyl-tetrahydropyridinyl | C(O)O | t-Butyl |

TABLE 14

| Ar | A | B | G | Q | $R^{34}$ |
|---|---|---|---|---|---|
| $H_3CO_2S$-phenyl-F | $CH_2$ | O | 3-methyl-pyrrolidinyl | 1,2,4-oxadiazolyl | Isopropyl |
| $H_3CO_2S$-phenyl | O | $CH_2$ | 3-methyl-azetidinyl | C(O)O | t-Butyl |
| $H_3CO_2S$-phenyl | $CH_2$ | O | 4-methyl-tetrahydropyridinyl | C(O)O | t-Butyl |

Representative Compound (6)

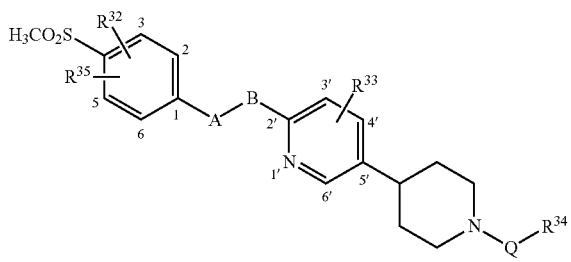

TABLE 15-continued

| $R^{33}$ | $R^{35}$ | $R^{32}$ | A | B | Q | $R^{34}$ |
|---|---|---|---|---|---|---|
| — | 2-$CH_3$ | 5-$CH_3$ | O | $CH_2$ | C(O)O | t-Butyl |
| — | 2-F | 5-$CH_3$ | $CH_2$ | $CH_2$ | C(O)O | t-Butyl |
| — | 2-F | 3-F | O | $CH_2$ | C(O)O | t-Butyl |
| 3'-F | 2-$CH_3$ | 5-F | O | $CH_2$ | C(O)O | Isopentyl |
| — | 2-F | 3-F | O | $CH_2$ | C(O)O | t-Butyl |
| — | 2-$CH_3$ | 3-$CH_3$ | O | $CH_2$ | C(O)O | t-Butyl |

The pharmacological tests are described below.

(Pharmacological Test A)

The GPR119 agonist effect was studied by measuring the effect of an analyte on increase of intracellular amount of cAMP in human GPR119 introduced cells. The testing method is described below.

(1) Construction of the Stable Cell Line Expressing Human G Protein-Coupled-Receptor 119 (hGPR119)

Human GPR119 gene (NM 178471) is purchased from American Type Culture Collection (ATCC No. 10807349). Hind III site-added forward side primer (tcctggatccatggaatcatctttctcatt: sequence No. 1) and Apa I site-added reverse side primer (tcctgggcccttagccatcaaactctgagc: sequence No. 2) are designed. The target gene is amplyfied by a polymerase chain reaction (PCR) method using KOD-Plus-Ver. 2 (TOYOBO #KOD-211). PCR is conducted by repeating three steps consisting of the step of 98° C.-10 seconds, the step of 55° C.-30 seconds, and the step of 68° C.-1 minute and 10 seconds in 35 cycles. The amplified PCR product is inserted into pcDNA5/FRT/TO (Invitrogen #V6520-20) plasmid. Cells, which can constantly express the target gene with tetracycline, are constructed using Flp-In T-REx-systen (invitorogen).

(2) Measurement of Intracellular Cyclic Adenosine Monophosphate (cAMP)

The hGPR119 introduced cells prepared in (1) are plated on a 96-well plate using Dulbecco's Modified Eagle Medium containing heat-inactived 10% fetal bovine serum. After incubation of 24 hours, tetracyclin (invitrogen #Q10019) is added to the culture medium to induce hGPR119 gene expression. After further incubation of 24 hours, the cells are stimulated with 0.5 mM 3-ISOBUTYL-1-METHYLXANTHINE (Sigma #I7018) phosphate buffer containing the analyte at 37° C. for 30 minutes. The amount of the intracellular cAMP is measured by using FLUOstar Optima (BMG LABTECH) according to the protocol of HitHunter™ cAMP XS+ Assay (GE Healthcare #90007503) to give the agonist activity of the analyte to the GPR119 receptor.

(3) Experimental Results

As is evident from Table 16 of Example 86 described below, the compounds of Examples 1 and 2 show an excellent GPR119 agonist effect.

As is also evident from Table 17 of Example 87 described below, the compounds of Examples 25, 83, or the like show an excellent GPR119 agonist effect.

(Pharmacological Test B)

Oral glucose tolerance is tested in normal mice.

(1) Experimental Procedure

In this experiment, the inhibitory effect of an analyte on glycemic excursions is examined after glucose administration in normal mice. The test methods are described below.

Male 9-week-old ICR mice, habituated to the experimental environment for two weeks, are fasted for 18 hours and used to this experiment. Mice are orally administered the analyte or vehicle (polyethylene glycol 400:ethanol:Tween 80=8:1:1). After 30 minutes, they were orally given glucose at the dose of 3 g/kg.

Blood was collected at just before the analyte or vehicle administration (−30 minutes), immediately before glucose challenge (0 minute), 20 minutes, 40 minutes, 60 minutes, and 120 minutes after glucose ingestion to determine blood glucose levels.

Inhibition rate (%) of the analyte versus vehicle in areas under the glycemic excursion curve between 0 and 120 min after glucose challenge is determined.

(2) Experimental Results

As is evident from Table 18 of Example 88 described below, the compound of Example 1 shows a strong inhibitory effect on glycemic excursions in oral glucose tolerance test of normal mice.

As is described above, the compound represented by the formula (I) described in (A) or (B), the cyclic amine derivative represented by the formula (II) described in (C) or (D), or a pharmaceutically acceptable salt thereof has a GPR119 agonist effect. Therefore, they are expected to be used for treatment of diabetes. They are also expected to be used for a life-style related diseases such as obesity and metabolic syndrome.

The compound represented by the formula (I) described in (A) or (B), the cyclic amine derivative represented by the formula (II) described in (C) or (D), or a pharmaceutically acceptable salt thereof can be used in combination with a conventional agent for treatment of diabetes.

The compound represented by the formula (I) described in (A) or (B), the cyclic amine derivative represented by the formula (II) described in (C) or (D), or a pharmaceutically acceptable salt thereof can be administered to human beings by suitable administration methods such as oral administration or parenteral administration.

The compound or salt can be granulated in suitable manners for the preparation of pharmaceuticals. For instance, the compound or salt can be processed to give tablets, granule, powder, capsule, suspension, injection, suppository, and the like.

For the preparation of these pharmaceuticals, when they are tablets, appropriate additives such as excipients, disintegrators, binders, lubricants and dyes can be used. Lactose, D-mannitol, crystalline cellulose and glucose can be used as the excipients. Starch and carboxymethylcellulose calcium (CMC-Ca) can be used as the disintegrators, magnesium stearate and talc as the lubricants. Hydroxypropylcellulose (HPC), gelatin and polyvinylpyrrolidone (PVP) can be used as the binders. For the preparation of injection, a solvent, a stabilizer, a solubilizer, a suspending agent, an emulsifier, an analgesic, a buffer and a preservative can be used.

The compound represented by the formula (I) described in (A) or (B), the cyclic amine derivative represented by the formula (II) described in (C) or (D), or a pharmaceutically acceptable salt thereof can be administered to an adult generally in an amount of 0.01 mg to 100 mg a day by injection and 1 mg to 2.000 mg a day by oral administration. The dosage can be adjusted according to age and conditions of the patient.

The invention is further described by the following non-limiting examples.

EXAMPLES

Example 1 tert-Butyl 4-[2-(4-methanesufonylphenoxymethyl)pyridin-5-yl]piperidine-1-carboxylate (1) Benzyl 4-[(2-hydroxymethyl)pyridin-5-yl]-3,6-dihydro-2H-pyridine-1-carboxylate To a solution of 5-bromopyridin-2-methanol (100 mg, 0.532 mmol) and benzyl 4-(4,4,5,5-tetramethyl-1,3,2-dioxaborolan-2-yl)-3,6-dihydro-2H-pyridine-1-carboxylate (200 mg, 0.585 mmol) in dry N,N-dimethylformamide (1.3 mL)-dry tetrahydrofuran (1.3 mL) was added [1,1-bis(diphenylphosphino)ferrocene]dichloropalladium(II) (complex with dichloromethane) (22 mg, 0.027 mmol) and cesium carbonate (347 mg, 1.06 mmol). The mixture was stirred at 90° C. under $N_2$ for 2.5 hours, allowed to cool to room temperature, diluted with water (5 mL) and extracted with ethyl acetate. The organic layer was washed with brine, dried over anhydrous sodium sulfate and concentrated under reduced pressure. The residue was purified by silica gel column chromatography (hexane/ethyl acetate=1/2) to give the title compound as an orange oil (120 mg, yield 70%).

$^1$H NMR (CDCl$_3$, 400 MHz): δ=2.5-2.6 (2H, m), 3.58 (1H, brs), 3.7-3.8 (2H, m), 4.1-4.2 (2H, m), 4.76 (2H, s), 5.18 (2H, s), 6.0-6.2 (1H, m), 7.22 (1H, d, J=8 Hz), 7.3-7.4 (5H, m), 7.65 (1H, dd, J=2 Hz, 8 Hz), 8.57 (1H, d, J=2 Hz).

(2) tert-Butyl 4-[(2-hydroxymethyl)pyridin-5-yl]piperidine-1-carboxylate

To a solution of benzyl 4-[(2-hydroxymethyl)pyridin-5-yl]-3,6-dihydro-2H-pyridine-1-carboxylate (527 mg, 1.63 mmol) in methanol (16 mL) was added 10% palladium-carbon (105 mg). The mixture was hydrogenated at room temperature for 17 hours and filtered through Celite pad. The filtrate was concentrated under reduced pressure. To a solution of the residue in tetrahydrofuran (8 mL)-water (8 mL) was added triethylamine (0.34 mL, 2.43 mmol) and di-tert-butyl dicarbonate (390 mg, 1.79 mmol). The mixture was stirred at room temperature for 10 minutes, diluted with water (15 mL) and extracted with ethyl acetate. The organic layer was washed with brine, dried over anhydrous sodium sulfate and concentrated under reduced pressure. The residue was purified by silica gel column chromatography (hexane/ethyl acetate=1/2→chloroform/methanol=30/1) to give the title compound as a pale yellow oil (322 mg, yield 68%).

$^1$H NMR (CDCl$_3$, 400 MHz): δ=1.49 (9H, s), 1.5-1.7 (2H, m), 1.8-1.9 (2H, m), 2.6-2.8 (1H, m), 2.7-2.9 (2H, m), 3.61 (1H, brs), 4.2-4.4 (2H, m), 4.74 (2H, s), 7.20 (1H, d, J=8 Hz), 7.51 (1H, dd, J=2 Hz, 8 Hz), 8.43 (1H, d, J=2 Hz).

(3) tert-Butyl 4-[2-(methanesulfonyloxymethyl)pyridin-5-yl]piperidine-1-carboxylate To an ice-cooled solution of tert-butyl 4-[(2-hydroxymethyl)pyridin-5-yl]piperidine-1-carboxylate (100 mg, 0.342 mmol) in chloroform (2.4 mL) was added triethylamine (0.07 mL, 0.51 mmol) and then added dropwise a solution of methanesulfonyl chloride (0.030 mL, 0.39 mmol) in chloroform (1 mL). The mixture was stirred at room temperature under $N_2$ for 3 hours and concentrated under reduced pressure. The residue was purified by silica gel column chromatography (hexane/ethyl acetate=9/1, ethyl acetate) to give the title compound as an orange oil (59 mg, yield 47%).

$^1$H NMR (CDCl$_3$, 400 MHz): δ=1.49 (9H, s), 1.6-1.7 (2H, m), 1.8-1.9 (2H, m), 2.6-2.8 (1H, m), 2.7-2.9 (2H, m), 3.09 (3H, s), 4.2-4.3 (2H, m), 5.31 (2H, s), 7.42 (1H, d, J=8 Hz), 7.58 (1H, dd, J=2 Hz, 8 Hz), 8.48 (1H, d, J=2 Hz).

(4) tert-Butyl 4-[2-(4-methanesufonylphenoxymethyl)-pyridin-5-yl]piperidine-1-carboxylate A solution of 4-(methanesulfonyl)phenol (25 mg, 0.14 mmol) in dry tetrahydrofuran (0.5 mL) was added dropwise over 5 minutes to an ice-cooled suspension of sodium hydride (55% dispersion in mineral oil, 10 mg, 0.22 mmol) in dry tetrahydrofuran (0.5 mL). After stirring for an additional 20 minutes under $N_2$, a solution of tert-butyl 4-[2-(methanesulfonyloxymethyl)pyridine-5-yl]piperidine-1-carboxylate (59 mg, 0.16 mmol) in dry tetrahydrofuran (0.5 mL) was added dropwise over 5 minutes to the mixture. The resulting mixture was stirred at room temperature for 2 hours and then refluxed overnight, to which was added saturated aqueous ammonium chloride solution and extracted with ethyl acetate. The organic layer was washed with brine, dried over anhydrous sodium sulfate and concentrated under reduced pressure. The residue was purified by silica gel column chromatography (hexane/ethyl acetate=1/2) to give a white solid. The solid was dissolved in ethyl acetate and extracted with 1N hydrochloric acid. The aqueous layer was neutralized by adding 1N sodium hydroxide and extracted with ethyl acetate. The organic layer was washed with brine, dried over anhydrous sodium sulfate and concentrated under reduced pressure to give the title compound as a white crystal (7.5 mg, yield 11%).

FAB-MS (m/z): 447 (M+1)

$^1$H NMR (CDCl$_3$, 400 MHz): δ=1.48 (9H, s), 1.6-1.7 (2H, m), 1.8-1.9 (2H, m), 2.6-2.8 (1H, m), 2.7-2.9 (2H, m), 3.03 (3H, s), 4.2-4.4 (2H, m), 5.25 (2H, s), 7.12 (2H, d, J=9 Hz), 7.42 (1H, d, J=8 Hz), 7.56 (1H, dd, J=2 Hz, 8 Hz), 7.87 (2H, d, J=9 Hz), 8.48 (1H, d, J=2 Hz).

Example 2 tert-Butyl 4-[5-(4-methanesulfonylphenoxymethyl)pyridin-2-yl]piperidine-1-carboxylate (1) Benzyl 4-[(5-hydroxymethyl)pyridin-2-yl]-3,6-dihydro-2H-pyridine-1-carboxylate The title compound was prepared from 2-bromopyridin-5-methanol (219 mg, 1.17 mmol) following a procedure analogous to that in Example 1(1) as a yellow oil (330 mg, yield 87%).

$^1$H NMR (CDCl$_3$, 400 MHz): δ=2.11 (1H, brs), 2.6-2.7 (2H, m), 3.7-3.8 (2H, m), 4.2-4.3 (2H, m), 4.72 (2H, brs), 5.18 (2H, s), 6.5-6.6 (1H, m), 7.3-7.4 (5H, m), 7.69 (1H, dd, J=2 Hz, 8 Hz), 8.01 (1H, d, J=8 Hz), 8.53 (1H, d, J=2 Hz).

(2) tert-Butyl 4-[(5-hydroxymethyl)pyridin-2-yl]piperidine-1-carboxylate

The title compound was prepared from benzyl 4-[(5-hydroxymethyl)pyridin-2-yl]-3,6-dihydro-2H-pyridine-1-carboxylate (330 mg, 1.02 mmol) following a procedure analogous to that in Example 1(2) as a colorless oil (172 mg, yield 58%).

$^1$H NMR (CDCl$_3$, 400 MHz): δ=1.47 (9H, s), 1.6-1.8 (2H, m), 1.8-2.0 (2H, m), 2.7-2.9 (3H, m), 4.2-4.3 (2H, m), 4.71 (2H, s), 7.16 (1H, d, J=8 Hz), 7.67 (1H, dd, J=2 Hz, 8 Hz), 8.52 (1H, d, J=2 Hz).

(3) tert-Butyl 4-[5-(4-methanesulfonylphenoxymethyl)-pyridin-2-yl]piperidine-1-carboxylate Diethyl azodicarboxylate (2.2M in toluene, 0.17 mL) was added dropwise under $N_2$ to an ice-cooled solution of tert-butyl 4-[(5-hydroxymethyl)pyridin-2-yl]piperidine-1-carboxylate (100 mg, 0.342 mmol), 4-(methanesulfonyl)phenol (65 mg, 0.38 mmol) and triphenylphosphine (99 mg, 0.38 mmol) in dry tetrahydrofuran (1.7 mL). The mixture was stirred at room temperature for 26 hours, and toluene (5 mL) and cyclohexane (5 mL) was added. The resulting mixture was stirred for an additional 3 hours, washed with 1N sodium hydroxide, dried over anhydrous sodium sulfate and concentrated under reduced pressure. The residue was purified by silica gel column chromatography (hexane/ethyl acetate=15/85→ethyl acetate) to give the title compound as a white crystal (59 mg, yield 39%).

FAB-MS (m/z): 447 (M+1)

m.p.: 140-142° C.

H NMR (CDCl$_3$, 400 MHz): δ=1.48 (9H, s), 1.6-1.8 (2H, m), 1.9-2.0 (2H, m), 2.8-3.0 (3H, m), 3.04 (3H, s), 4.2-4.4 (2H, m), 5.13 (2H, s), 7.10 (2H, d, J=9 Hz), 7.21 (1H, d, J=8 Hz), 7.72 (1H, dd, J=2 Hz, 8 Hz), 7.89 (2H, d, J=9 Hz), 6.60 (1H, d, J=2 Hz).

IR (KBr, cm$^{-1}$): 2976, 2922, 1699, 1678, 1595, 1577, 1498, 1423, 1406, 1365, 1317, 1298, 1254, 1173, 1147, 1117, 1095, 1016, 960, 835, 769, 544, 525.

Example 3 tert-Butyl 4-[2-(4-methanesulfonylbenzylamino)pyridin-5-yl]piperidine-1-carboxylate (1) N-(5-Bromopyridin-2-yl)-4-methanesulfonylbenzamide To a solution of 4-methanesulfonylbenzoic acid (100 mg, 0.50 mmol) and 2-amino-5-bromopyridine (104 mg, 0.60 mmol) in dry dichloromethane (10 mL) was added 4-(dimethylamino)pyridine (67 mg, 0.55 mmol) and 1-ethyl-3-(3-dimethylaminopropyl)carbodiimide hydrochloride (105 mg, 0.55 mmol). The mixture was stirred at room temperature overnight under N$_2$, diluted with water (10 mL) and extracted with ethyl acetate. The organic layer was washed with brine, dried over anhydrous sodium sulfate and concentrated under reduced pressure. The residue was purified by silica gel column chromatography (chloroform/ethyl acetate=3/1) to give the title compound as a white crystal (56 mg, yield 32%).

$^1$H NMR (CDCl$_3$, 400 MHz): δ=3.10 (3H, s), 7.90 (1H, dd, J=2 Hz, 9 Hz), 8.10 (4H, s), 8.32 (1H, d, J=9 Hz), 8.39 (1H, d, J=2 Hz), 8.55 (1H, brs).

(2) tert-Butyl 4-[2-(4-methanesulfonylbenzoylamino)-pyridin-5-yl]-3,6-dihydro-2H-pyridine-1-carboxylate To a solution of N-(5-bromopyridin-2-yl)-4-methanesulfonylbenzamide (287 mg, 0.81 mmol) and tert-butyl 4-(4,4,5,5-tetramethyl-1,3,2-dioxaborolan-2-yl)-3,6-dihydro-2H-pyridine-1-carboxylate (305 mg, 0.97 mmol) in dry N,N-dimethylformamide (10 mL) was added [1,1-bis(diphenylphosphino)ferrocene]dichloropalladium(II) (complex with dichloromethane) (33 mg, 0.040 mmol) and cesium carbonate (527 mg, 1.6 mmol). The mixture was stirred at 90° C. overnight under N$_2$, allowed to cool to room temperature, diluted with water (10 mL) and extracted with ethyl acetate. The organic layer was washed with brine, dried over anhydrous sodium sulfate and concentrated under reduced pressure. The residue was purified by silica gel column chromatography (hexane/ethyl acetate=1/2) to give the title compound as a white crystal (83 mg, yield 22%).

$^1$H NMR (CDCl$_3$, 400 MHz): δ=1.50 (9H, s), 2.4-2.6 (2H, m), 3.10 (3H, s), 3.6-3.7 (2H, m), 4.0-4.2 (2H, m), 6.0-6.2 (1H, m), 7.78 (1H, dd, J=2 Hz, 9 Hz), 8.09 (2H, d, J=8 Hz), 8.12 (2H, d, J=8 Hz), 8.31 (1H, d, J=2 Hz), 8.34 (1H, d, J=9 Hz), 8.79 (1H, brs).

(3) tert-Butyl 4-[2-(4-methanesulfonylbenzoylamino)pyridin-5-yl]piperidine-1-carboxylate To a solution of tert-butyl 4-[2-(4-methanesulfonylbenzoylamino)pyridin-5-yl]-3,6-dihydro-2H-pyridine-1-carboxylate (83 mg, 0.18 mmol) in methanol (2 mL) was added 10% palladium-carbon (8.3 mg). The mixture was hydrogenated at room temperature for 4 hours and filtered through Celite pad. The filtrate was concentrated under reduced pressure. The residue was purified by silica gel column chromatography (hexane/ethyl acetate=2/3) to give the title compound as a white crystal (47 mg, yield 57%).

$^1$H NMR (CDCl$_3$, 400 MHz): δ=1.49 (9H, s), 1.5-1.7 (2H, m), 1.7-1.9 (2H, m), 2.5-2.8 (1H, m), 2.7-2.9 (2H, m), 3.10 (3H, s), 4.2-4.4 (2H, m), 7.63 (1H, dd, J=2 Hz, 8 Hz), 8.0-8.2 (5H, m), 8.31 (1H, d, J=8 Hz), 9.03 (1H, brs).

(4) tert-Butyl 4-[2-(4-methanesulfonylbenzylamino)-pyridin-5-yl]piperidine-1-carboxylate To a solution of tert-butyl 4-[2-(4-methanesulfonylbenzoylamino)pyridin-5-yl]piperidine-1-carboxylate (47 mg, 0.10 mmol) in dichloromethane (1 mL) was added trifluoroacetic acid (1 mL). The mixture was stirred at room temperature for 30 minutes, diluted with water (10 mL) and extracted with ethyl acetate. To the aqueous layer was added 30% ammonia solution (3 mL) and extracted with ethyl acetate. The combined organic layer was washed with brine, dried over anhydrous sodium sulfate and concentrated under reduced pressure.

A solution of the residue in dry tetrahydrofuran (1 mL) was added dropwise under N$_2$ to a suspension of lithium aluminum hydride (4.7 mg, 0.12 mmol) in dry tetrahydrofuran (2 mL). The mixture was stirred at 80° C. for 17 hours and cooled in an ice bath followed by the addition of diethyl ether (5 mL) and aqueous sodium sulfate solution. The resulting mixture was stirred for 5 minutes, filtered through Celite pad and the filtrate was concentrated under reduced pressure.

The residue was dissolved in tetrahydrofuran (1 mL)-water (1 mL), and was added triethylamine (21 μL, 0.15 mmol) and di-tert-butyl dicarbonate (22 mg, 0.10 mmol). The mixture was stirred at room temperature for 17 hours, diluted with water (5 mL) and extracted with ethyl acetate. The organic layer was washed with brine, dried over anhydrous sodium sulfate and concentrated under reduced pressure. The residue was purified by silica gel column chromatography (hexane/ethyl acetate=2/1) to give the title compound as a white amorphous (4.3 mg, yield 9%).

FAB-MS (m/z): 446 (M+1)

$^1$H NMR (CDCl$_3$, 400 MHz): δ=1.47 (9H, s), 1.5-1.7 (2H, m), 1.7-1.8 (2H, m), 2.5-2.6 (1H, m), 2.7-2.9 (2H, m), 3.04 (3H, s), 4.1-4.4 (2H, m), 4.64 (2H, d, J=6 Hz), 4.9-5.0 (1H, m), 6.35 (1H, d, J=8 Hz), 7.2-7.3 (1H, m), 7.55 (2H, d, J=8 Hz), 7.89 (2H, d, J=8 Hz), 7.96 (1H, d, J=2 Hz).

Example 4 tert-Butyl 4-[6-(4-methanesulfonylphenoxymethyl)pyridazin-3-yl]-3,6-dihydro-2H-pyridine-1-carboxylate (1) 3-Chloro-6-(4-methanesulfonylphenoxymethyl)-pyridazine To a solution of potassium 4-(methanesulfonyl)phenolate (150 mg, 0.713 mmol) in N,N-dimethylformamide (2 mL) was added a solution of 3-bromomethyl-6-chloropyridazine (221 mg, 1.07 mmol) in N,N-dimethylformamide (2 mL). The mixture was stirred at room temperature for 2.5 hours, poured into water and extracted with ethyl acetate. The organic layer was washed with brine, dried over anhydrous sodium sulfate and concentrated under reduced pressure. The residue was purified by silica gel column chromatography (hexane/ethyl acetate=1/1→2/3) to give the title compound as a white crystal (148 mg, yield 69%).

$^1$H NMR (CDCl$_3$, 400 MHz): δ=3.04 (3H, s), 5.50 (2H, s), 7.14 (2H, d, J=9 Hz), 7.59 (1H, d, J=9 Hz), 7.70 (1H, d, J=9 Hz), 7.90 (2H, d, J=9 Hz).

(2) tert-Butyl 4-[6-(4-methanesulfonylphenoxymethyl)-pyridazin-3-yl]-3,6-dihydro-2H-pyridine-1-carboxylate To a solution of 3-chloro-6-(4-methanesulfonylphenoxymethyl)pyridazine (79 mg, 0.26 mmol) and tert-butyl 4-(4,4,5,5-tetramethyl-1,3,2-dioxaborolan-2-yl)-3,6-dihydro-2H-pyridine-1-carboxylate (82 mg, 0.26 mmol) in dry N,N-dimethylformamide (3 mL) was added tetrakis(triphenylphosphine)palladium (9.0 mg, 7.9 μmol) and cesium carbonate (129 mg, 0.397 mmol). The mixture was stirred at 80° C. for 2 hours, allowed to cool to room temperature, poured into water and extracted with ethyl acetate. The organic layer was washed with brine, dried over anhydrous sodium sulfate and concentrated under reduced pressure. The residue was purified by silica gel column chromatography (chloroform/ethyl acetate=10/1 and hexane/ethyl acetate=1/2) to give the title compound as a white crystal (16 mg, yield 14%).

FAB-MS (m/z): 446 (M+1)

$^1$H NMR (CDCl$_3$, 400 MHz): δ=1.50 (9H, s), 2.7-2.9 (2H, m), 3.03 (3H, s), 3.6-3.8 (2H, m), 4.1-4.3 (2H, m), 5.51 (2H, s), 6.67 (1H, brs), 7.15 (2H, d, J=9 Hz), 7.63 (2H, s), 7.88 (2H, d, J=9 Hz).

Example 5 tert-Butyl 4-[6-(4-methanesulfonylphenoxymethyl)pyridazin-3-yl]piperidine-1-carboxylate The title compound was prepared from tert-butyl 4-[6-(4-methanesulfonylphenoxymethyl)pyridazin-3-yl]-3,6-dihydro-2H-pyridine-1-carboxylate (Example 4) (14 mg, 31.4 μmol) following a procedure analogous to that in Example 3(3) as a white crystal (10 mg, yield 73%).

$^1$H NMR (CDCl$_3$, 400 MHz): δ=1.48 (9H, s), 1.7-1.9 (2H, m), 1.9-2.1 (2H, m), 2.8-3.0 (2H, m), 3.03 (3H, s), 3.0-3.2 (1H, m), 4.2-4.4 (2H, m), 5.49 (2H, s), 7.15 (2H, d, J=9 Hz), 7.39 (1H, d, J=9 Hz), 7.63 (1H, d, J=9 Hz), 7.89 (2H, d, J=9 Hz).

Example 6 tert-Butyl 4-[2-(4-methanesulfonylbenzyloxy)pyridin-5-yl]-3,6-dihydro-2H-pyridine-1-carboxylate (1) 5-Bromo-2-(4-methanesulfonylbenzyloxy)pyridine A solution of 2,5-dibromopyridine (474 mg, 2.00 mmol) and 4-(methanesulfonyl)benzyl alcohol (372 mg, 2.00 mmol) in tetrahydrofuran (5 mL) was cooled to −15° C. under N$_2$ and potassium tert-butoxide (1.0M in tetrahydrofuran, 2.2 mL, 2.20 mmol) was added dropwise over 10 minutes. The mixture was stirred at 0° C. for 5.5 hours, poured into saturated aqueous ammonium chloride solution and extracted with ethyl acetate. The organic layer was washed with brine, dried over anhydrous sodium sulfate and concentrated under reduced pressure. The residue was purified by silica gel column chromatography (hexane/ethyl acetate=1/1) to give the title compound (210 mg, yield 31%).

$^1$H NMR (CDCl$_3$, 400 MHz): δ=3.05 (3H, s), 5.45 (2H, s), 6.76 (1H, d, J=9 Hz), 7.63 (2H, d, J=9 Hz), 7.69 (1H, dd, J=2 Hz, 9 Hz), 7.94 (2H, d, J=9 Hz), 8.19 (1H, d, J=2 Hz).

(2) tert-Butyl 4-[2-(4-methanesulfonylbenzyloxy)pyridin-5-yl]-3,6-dihydro-2H-pyridine-1-carboxylate The title compound was prepared from 5-bromo-2-(4-methanesulfonylbenzyloxy)pyridine (50 mg, 0.146 mmol) following a procedure analogous to that in Example 3(2) as a white crystal (25 mg, yield 39%).

FAB-MS (m/z): 445 (M+1)

$^1$H NMR (CDCl$_3$, 400 MHz): δ=1.49 (9H, s), 2.4-2.6 (2H, m), 3.04 (3H, s), 3.6-3.7 (2H, m), 4.0-4.1 (2H, m), 5.49 (2H, s), 5.97 (1H, brs), 6.82 (1H, d, J=8 Hz), 7.6-7.7 (3H, m), 7.94 (2H, d, J=9 Hz), 8.14 (1H, d, J=2 Hz).

Example 7 tert-Butyl 4-[2-(4-methanesulfonylbenzyloxy)pyridin-5-yl]piperidine-1-carboxylate To a solution of tert-Butyl 4-[2-(4-methanesulfonylbenzyloxy)pyridin-5-yl]-3,6-dihydro-2H-pyridine-1-carboxylate (Example 6) (39 mg, 87.7 μmol) in methanol (2 mL) was added 10% platinum-carbon (15 mg). The mixture was hydrogenated at room temperature for 17 hours and filtered through Celite pad. The filtrate was concentrated under reduced pressure. The residue was purified by silica gel column chromatography (hexane/ethyl acetate=1/1) to give the title compound as a white crystal (20 mg, yield 51%).

FAB-MS (m/z): 447 (M+1)

$^1$H NMR (CDCl$_3$, 400 MHz): δ=1.48 (9H, s), 1.5-1.7 (2H, m), 1.7-1.9 (2H, m), 2.5-2.7 (1H, m), 2.7-2.9 (2H, m), 3.05 (3H, s), 4.1-4.4 (2H, m), 5.46 (2H, s), 6.80 (1H, d, J=8 Hz), 7.47 (1H, dd, J=2 Hz, 8 Hz), 7.64 (2H, d, J=8 Hz), 7.94 (2H, d, J=8 Hz), 7.99 (1H, d, J=2 Hz).

Example 8

5-[1-(5-Isopropyl-1,2,4-oxadiazol-3-yl)piperidin-4-yl]-2-(4-methanesulfonylphenoxymethyl)pyridine (1) 4-[2-(4-Methanesulfonylphenoxymethyl)pyridin-5-yl]piperidine To a solution of tert-butyl 4-[2-(4-methanesulfonyl-phenoxymethyl)pyridin-5-yl]piperidine-1-carboxylate (Example 1) (164 mg, 0.367 mmol) in dichloromethane (1.5 mL) was added trifluoroacetic acid (1.5 mL). The mixture was stirred at room temperature overnight and was then concentrated in vacuo. To the residue was added saturated aqueous sodium hydrogen carbonate solution and extracted with chloroform. The organic layer was dried over anhydrous sodium sulfate and concentrated under reduced pressure to give the title compound (125 mg, yield 98%).

$^1$H NMR (CDCl$_3$, 400 MHz): δ=1.6-1.8 (2H, m), 1.7-1.9 (2H, m), 2.6-2.9 (3H, m), 3.03 (3H, s), 3.1-3.3 (2H, m), 5.25 (2H, s), 7.12 (2H, d, J=9 Hz), 7.41 (1H, d, J=8 Hz), 7.59 (1H, dd, J=2 Hz, 8 Hz), 7.86 (2H, d, J=9 Hz), 8.49 (1H, d, J=2 Hz).

(2) 4-[2-(4-Methanesulfonylphenoxymethyl)pyridin-5-yl]piperidin-1-carbonitrile

To a solution of 4-[2-(4-methanesulfonylphenoxymethyl)pyridin-5-yl]piperidine (124 mg, 0.358 mmol) in dichloromethane (1 mL) was added a solution of sodium hydrogen carbonate (60 mg, 0.716 mmol) in water (0.5 mL). The mixture was cooled in an ice bath followed by the addition of a solution of cyanogen bromide (45 mg, 0.430 mmol) in dichloromethane (1 mL). The mixture was stirred at 0° C. for 30 minutes and then stirred at room temperature for an additional 1 hour. The mixture was poured into saturated aqueous sodium hydrogen carbonate solution and extracted with chloroform. The organic layer was dried over anhydrous sodium sulfate and concentrated under reduced pressure. The residue was purified by silica gel column chromatography (ethyl acetate) to give the title compound (114 mg, yield 86%).

$^1$H NMR (CDCl$_3$, 400 MHz): δ=1.8-2.0 (4H, m), 2.6-2.8 (1H, m), 3.03 (3H, s), 3.1-3.3 (2H, m), 3.5-3.7 (2H, m), 5.26 (2H, s), 7.12 (2H, d, J=9 Hz), 7.46 (1H, d, J=8 Hz), 7.58 (1H, dd, J=2 Hz, 8 Hz), 7.87 (2H, d, J=9 Hz), 8.48 (1H, d, J=2 Hz).

(3) N-Hydroxy-4-[2-(4-methanesulfonylphenoxymethyl)-pyridin-5-yl]piperidin-1-carboxamidine To a solution of 4-[2-(4-methanesulfonylphenoxymethyl)pyridin-5-yl]piperidin-1-carbonitrile (92 mg, 0.248 mmol) in ethanol (0.8 mL) was added 50% hydroxylamine solution (0.2 mL). The mixture was stirred at 60° C. for 4 hours, allowed to cool to room temperature and concentrated under reduced pressure to give the title compound (98 mg, yield 98%).

FAB-MS (m/z): 405 (M+1)

(4) 5-[1-(5-Isopropyl-1,2,4-oxadiazol-3-yl)piperidin-4-yl]-2-(4-methanesulfonylphenoxymethyl)pyridine A solution of N-hydroxy-4-[2-(4-methanesulfonylphenoxymethyl)pyridin-5-yl]piperidin-1-carboxamidine (98 mg, 0.242 mmol), isobutyric acid (22 μL, 0.242 mmol) and 1-hydroxybenzotriazole monohydrate (41 mg, 0.267 mmol) in N,N-dimethylformamide (2 mL) was cooled in an ice bath followed by the addition of N,N-diisopropylethylamine (0.14 mL, 0.800 mmol) and 1-(3-dimethylaminopropyl)-3-ethyl-carbodiimide hydrochloride (55 mg, 0.291 mmol). The mixture was stirred at room temperature overnight, poured into saturated aqueous sodium hydrogen carbonate solution and extracted with ethyl acetate. The organic layer was dried over anhydrous sodium sulfate and concentrated under reduced pressure. A suspension of the residue in toluene (4 mL) was refluxed for 2 hours, allowed to cool to room temperature and concentrated under reduced pressure. The residue was purified by silica gel column chromatography (hexane/ethyl acetate=1/2→1/5) to give a crystal. The crystal was recrystallized from ethyl acetate/hexane to give the title compound as a white crystal (59 mg, yield 53%).

FAB-MS (m/z): 457 (M+1)
m.p.: 143-145° C.
$^1$H NMR (CDCl$_3$, 400 MHz): δ=1.36 (6H, d, J=7 Hz), 1.7-2.0 (4H, m), 2.7-2.9 (1H, m), 2.9-3.2 (3H, m), 3.03 (3H, s), 4.1-4.3 (2H, m), 5.25 (2H, s), 7.12 (2H, d, J=9 Hz), 7.42 (1H, d, J=8 Hz), 7.58 (1H, dd, J=2 Hz, 8 Hz), 7.87 (2H, d, J=9 Hz), 8.50 (1H, d, J=2 Hz).
IR (KBr, cm$^{-1}$): 2976, 2925, 2836, 1579, 1541, 1498, 1458, 1406, 1387, 1292, 1246, 1140, 1093, 1039, 1007, 972, 910, 833, 771, 550, 526.

Example 9 tert-Butyl 4-[2-(4-ethoxycarbonyl-3-fluorophenoxymethyl)pyridin-5-yl]piperidine-1-carboxylate Diethyl azodicarboxylate (2.2M in toluene, 0.19 mL, 0.411 mmol) was added dropwise under N$_2$ to an ice-cooled solution of ethyl 2-fluoro-4-hydroxybenzoate (76 mg, 0.411 mmol), tert-butyl 4-[2-hydroxymethyl)pyridin-5-yl]piperidine-1-carboxylate (80 mg, 0.274 mmol) and triphenylphosphine (108 mg, 0.411 mmol) in dry tetrahydrofuran (2.1 mL). The mixture was stirred at room temperature overnight, poured into water and extracted with ethyl acetate. The organic layer was washed with brine, dried over anhydrous sodium sulfate and concentrated under reduced pressure. The residue was purified by silica gel column chromatography (hexane/ethyl acetate=3/1→1/2) to give the title compound as a pale yellow crystal (71 mg, yield 56%).

FAB-MS (m/z): 459 (M+1)
m.p.: 92-95° C.
$^1$H NMR (CDCl$_3$, 400 MHz): δ=1.37 (3H, t, 3=7 Hz), 1.49 (9H, s), 1.5-1.7 (2H, m), 1.8-1.9 (2H, m), 2.6-2.9 (3H, m), 4.2-4.4 (2H, m), 4.35 (2H, q, J=7 Hz), 5.22 (2H, s), 6.73 (1H, dd, J=2 Hz, 12 Hz), 6.81 (1H, dd, J=2 Hz, 8 Hz), 7.42 (1H, d, J=8 Hz), 7.57 (1H, dd, 3=2 Hz, 8 Hz), 7.90 (1H, t, 3=8 Hz), 8.48 (1H, d, J=2 Hz).
IR (KBr, cm$^{-1}$): 2978, 2856, 1705, 1684, 1622, 1576, 1508, 1456, 1429, 1363, 1340, 1273, 1238, 1176, 1128, 1086, 1041, 1018, 976, 862, 843, 771, 688.

Example 10 tert-Butyl 4-[2-(4-carboxy-3-fluorophenoxymethyl)pyridin-5-yl]piperidine-1-carboxylate To a solution of tert-butyl 4-[2-(4-ethoxycarbonyl-3-fluorophenoxymethyl)pyridin-5-yl]piperidine-1-carboxylate (Example 9) (60 mg, 0.131 mmol) in ethanol (0.9 mL)-water (0.2 mL) was added lithium hydroxide monohydrate (16 mg, 0.393 mmol). The mixture was stirred at room temperature overnight, diluted with water, neutralized by the addition of 1N hydrochloric acid and then extracted with chloroform. The organic layer was washed with brine, dried over anhydrous sodium sulfate and concentrated under reduced pressure to give the title compound as a white crystal (57 mg, quantitative yield).

FAB-MS (m/z): 431 (M+1)
$^1$H NMR (CDCl$_3$, 400 MHz): δ=1.49 (9H, s), 1.5-1.7 (2H, m), 1.8-1.9 (2H, m), 2.7-2.9 (3H, m), 4.2-4.4 (2H, m), 5.29 (2H, s), 6.77 (1H, dd, J=2 Hz, 13 Hz), 6.85 (1H, dd, J=2 Hz, 9 Hz), 7.48 (1H, d, J=8 Hz), 7.64 (1H, d, J=8 Hz), 7.96 (1H, t, J=9 Hz), 8.51 (1H, brs).
IR (KBr, cm$^{-1}$): 2974, 2929, 2850, 1691, 1620, 1576, 1508, 1450, 1419, 1365, 1342, 1298, 1277, 1232, 1173, 1155, 1117, 1093, 1043, 1020, 978, 943, 891, 849, 771, 752, 640, 607.

Example 11 tert-Butyl 4-[2-(2,6-dimethyl-4-methanesulfonylphenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (50 mg, 0.171 mmol) and 2,6-dimethyl-4-(methanesulfonyl)phenol (51 mg, 0.257 mmol) following a procedure analogous to that in Example 9 as a colorless oil (13 mg, yield 15%).

FAB-MS (m/z): 447 (M+1)
$^1$H NMR (CDCl$_3$, 400 MHz): δ=1.48 (9H, s), 1.6-1.7 (2H, m), 1.8-1.9 (2H, m), 2.37 (6H, s), 2.6-2.8 (1H, m), 2.7-2.9 (2H, m), 3.03 (3H, s), 4.2-4.4 (2H, m), 5.25 (2H, s), 7.12 (2H, d, J=9 Hz), 7.42 (1H, d, J=8 Hz), 7.56 (1H, dd, J=2 Hz, 8 Hz), 7.87 (2H, d, J=9 Hz), 8.48 (1H, d, J=2 Hz).

Example 12 tert-Butyl 4-[2-(2-fluoro-4-methanesulfonylphenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (33 mg, 0.113 mmol) and 2-fluoro-4-methanesulfonyl)phenol (32 mg, 0.170 mmol) following a procedure analogous to that in Example 9 as a white crystal (18 mg, yield 33%).

FAB-MS (m/z): 465 (M+1)

$^1$H NMR (CDCl$_3$, 400 MHz): δ=1.48 (9H, s), 1.5-1.7 (2H, m), 1.8-1.9 (2H, m), 2.6-2.9 (3H, m), 3.04 (3H, s), 4.2-4.4 (2H, m), 5.32 (2H, s), 7.19 (1H, t, J=8 Hz), 7.47 (1H, d, J=8 Hz), 7.58 (1H, dd, J=2 Hz, 8 Hz), 7.6-7.7 (2H, m), 8.47 (1H, d, J=2 Hz).

IR (KBr, cm$^{-1}$): 2978, 2927, 2850, 1680, 1606, 1576, 1512, 1450, 1429, 1365, 1327, 1304, 1238, 1178, 1147, 1128, 1076, 1036, 1005, 968, 906, 837, 766, 602, 534, 494.

Example 13 tert-Butyl 4-[2-(4-cyano-3-fluorophenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (30 mg, 0.103 mmol) and 2-fluoro-4-hydroxybenzonitrile (21 mg, 0.155 mmol) following a procedure analogous to that in Example 9 as a pale yellow crystal (18 mg, yield 42%).

FAB-MS (m/z): 412 (M+1)

$^1$H NMR (CDCl$_3$, 400 MHz): δ=1.48 (9H, s), 1.5-1.7 (2H, m), 1.8-1.9 (2H, m), 2.6-2.9 (3H, m), 4.2-4.4 (2H, m), 5.23 (2H, s), 6.82 (1H, dd, J=2 Hz, 11 Hz), 6.87 (1H, dd, J=2 Hz, 8 Hz), 7.41 (1H, d, J=8 Hz), 7.52 (1H, t, J=8 Hz), 7.58 (1H, dd, J=2 Hz, 8 Hz), 8.48 (1H, brs).

IR (KBr, cm$^{-1}$): 2976, 2943, 2918, 2229, 1699, 1620, 1574, 1506, 1444, 1417, 1365, 1335, 1302, 1254, 1238, 1205, 1174, 1126, 1101, 1061, 1043, 1011, 976, 864, 825, 769, 737, 625.

Example 14 tert-Butyl 4-[2-(4-acetylaminophenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (30 mg, 0.103 mmol) and N-(4-hydroxyphenyl)acetamide (23 mg, 0.155 mmol) following a procedure analogous to that in Example 9 as a white crystal (19 mg, yield 44%).

FAB-MS (m/z): 426 (M+1)

$^1$H NMR (CDCl$_3$, 400 MHz): δ=1.48 (9H, s), 1.5-1.9 (4H, m), 2.15 (3H, s), 2.6-2.9 (3H, m), 4.1-4.4 (2H, m), 5.17 (2H, s), 6.94 (2H, d, J=9 Hz), 7.09 (1H, brs), 7.38 (2H, d, J=9 Hz), 7.45 (1H, d, J=8 Hz), 7.55 (1H, d, J=8 Hz), 8.45 (1H, brs).

IR (KBr, cm$^{-1}$): 3309, 2927, 1685, 1655, 1601, 1541, 1510, 1479, 1458, 1437, 1363, 1300, 1277, 1236, 1174, 1126, 1055, 1012, 935, 883, 860, 827, 769, 520.

Example 15 tert-Butyl 4-[2-[3-fluoro-4-((R)-2-hydroxy-1-methylethyl-carbamoyl)phenoxymethyl]pyridin-5-yl]piperidine-1-carboxylate A solution of tert-butyl 4-[2-(4-carboxy-3-fluorophenoxymethyl)pyridin-5-yl]piperidine-1-carboxylate (Example 10) (21 mg, 0.049 mmol), 1-hydroxybenzotriazole monohydrate (9.3 mg, 0.061 mmol) and 1-(3-dimethylaminopropyl)-3-ethylcarbodiimide hydrochloride (12 mg, 0.061 mmol) in dry tetrahydrofuran (0.5 mL) was stirred at room temperature for 1 hour followed by the addition of a solution of (S)-(−)-2-amino-1-propanol (7.6 μL, 0.098 mmol) in dry tetrahydrofuran (0.05 mL). The mixture was stirred at room temperature overnight, to which was added saturated aqueous sodium hydrogen carbonate solution and extracted with chloroform. The organic layer was washed with brine, dried over anhydrous sodium sulfate and concentrated under reduced pressure. The residue was purified by silica gel column chromatography (chloroform/methanol=100/1) to give the title compound as a white crystal (21 mg, yield 86%).

FAB-MS (m/z): 488 (M+1)

$^1$H NMR (CDCl$_3$, 400 MHz): δ=1.28 (3H, d, J=7 Hz), 1.49 (9H, s), 1.5-1.7 (2H, m), 1.8-1.9 (2H, m), 2.6-2.9 (4H, m), 3.6-3.7 (1H, m), 3.7-3.8 (1H, m), 4.2-4.4 (3H, m), 5.22 (2H, s), 6.72 (1H, dd, J=2 Hz, 14 Hz), 6.7-6.8 (1H, m), 6.87 (1H, dd, J=2 Hz, 9 Hz), 7.43 (1H, d, J=8 Hz), 7.57 (1H, dd, J=2 Hz, 8 Hz), 8.03 (1H, t, J=9 Hz), 8.48 (1H, d, J=2 Hz).

IR (KBr, cm$^{-1}$): 3325, 2976, 2935, 2858, 1695, 1627, 1573, 1539, 1504, 1456, 1427, 1365, 1335, 1306, 1273, 1236, 1171, 1117, 1095, 1045, 1014, 974, 887, 843, 769.

Example 16 tert-Butyl 4-[2-[4-(1,2,4-triazol-1-yl)phenoxymethyl]pyridin-5-yl]piperidine-1-carboxylate The title compound was prepared from 4-(1,2,4-triazol-1-yl)phenol (13 mg, 0.079 mmol) following a procedure analogous to that in Example 1(4) as a white crystal (28 mg, yield 82%).

FAB-MS (m/z): 436 (M+1)

m.p.: 147-150° C.

$^1$H NMR (CDCl$_3$, 400 MHz): δ=1.49 (9H, s), 1.5-1.7 (2H, m), 1.8-1.9 (2H, m), 2.6-2.9 (3H, m), 4.2-4.4 (2H, m), 5.23 (2H, s), 7.10 (2H, d, J=9 Hz), 7.45 (1H, d, J=8 Hz), 7.56 (1H, dd, J=2 Hz, 8 Hz), 7.56 (2H, d, J=9 Hz), 8.07 (1H, s), 8.45 (1H, s), 8.49 (1H, brs).

IR (KBr, cm$^{-1}$): 3107, 3006, 2976, 2920, 2860, 1693, 1595, 1576, 1523, 1456, 1419, 1369, 1306, 1277, 1232, 1171, 1115, 1086, 1059, 1016, 982, 953, 926, 889, 862, 829, 769, 673, 642, 521.

Example 17 tert-Butyl 4-[2-[4-(tetrazol-1-yl)phenoxymethyl]pyridin-5-yl]piperidine-1-carboxylate The title compound was prepared from 4-(tetrazol-1-yl)phenol (9.8 mg, 0.060 mmol) following a procedure analogous to that in Example 1(4) as a white crystal (12 mg, yield 45%).

FAB-MS (m/z): 437 (M+1)

$^1$H NMR (CDCl$_3$, 400 MHz): δ=1.49 (9H, s), 1.5-1.7 (2H, m), 1.8-1.9 (2H, m), 2.6-2.9 (3H, m), 4.2-4.4 (2H, m), 5.25

(2H, s), 7.16 (2H, d, J=9 Hz), 7.45 (1H, d, J=8 Hz), 7.57 (1H, dd, J=1 Hz, 8 Hz), 7.59 (2H, d, J=9 Hz), 8.49 (1H, brs), 8.69 (1H, s).

IR (KBr, cm$^{-1}$): 3124, 2978, 2929, 2852, 1699, 1684, 1520, 1458, 1419, 1365, 1309, 1277, 1248, 1207, 1173, 1117, 1093, 1053, 1020, 997, 833, 773, 525.

Example 18 tert-Butyl 4-[2-(3-fluoro-4-methanesulfonylphenoxymethyl)pyridin-5-yl]piperdine-1-carboxylate The title compound was prepared from 3-fluoro-4-methanesulfonylphenol (10 mg, 0.053 mmol) following a procedure analogous to that in Example 1(4) as a white crystal (7.6 mg, yield 41%).

FAB-MS (m/z): 465 (M+1)

$^1$H NMR (CDCl$_3$, 400 MHz): δ=1.49 (9H, s), 1.5-1.7 (2H, m), 1.8-1.9 (2H, m), 2.6-2.9 (3H, m), 3.18 (3H, s), 4.2-4.4 (2H, m), 5.23 (2H, s), 6.85 (1H, dd, J=2 Hz, 12 Hz), 6.91 (1H, dd, J=2 Hz, 8 Hz), 7.39 (1H, d, J=8 Hz), 7.57 (1H, dd, J=2 Hz, 8 Hz), 7.86 (1H, t, J=8 Hz), 8.48 (1H, d, J=2 Hz).

IR (KBr, cm$^{-1}$): 3005, 2974, 2929, 2854, 1685, 1610, 1577, 1489, 1456, 1431, 1363, 1323, 1304, 1277, 1236, 1171, 1157, 1134, 1078, 1036, 1012, 970, 887, 835, 771, 619, 509.

Example 19 tert-Butyl 4-[2-(3-methanesulfonylmethylphenoxymethyl)-pyridin-5-yl]piperidine-1-carboxylate The title compound was prepared from tert-butyl 4-[(2-hydroxymethyl)pyridin-5-yl]piperidine-1-carboxylate (Example 1(2)) (31 mg, 0.105 mmol) and 3-methanesulfonylmethylphenol (29 mg, 0.158 mmol) following a procedure analogous to that in Example 9 as a white crystal (23 mg, yield 48%).

FAB-MS (m/z): 461 (M+1)

$^1$H NMR (CDCl$_3$, 400 MHz): δ=1.49 (9H, s), 1.5-1.7 (2H, m), 1.7-1.9 (2H, m), 2.6-2.9 (3H, m), 2.72 (3H, s), 4.21 (2H, s), 4.2-4.4 (2H, m), 5.19 (2H, s), 6.9-7.1 (3H, m), 7.33 (1H, t, J=8 Hz), 7.45 (1H, d, J=8 Hz), 7.55 (1H, dd, J=2 Hz, 8 Hz), 8.47 (1H, brs).

IR (KBr, cm$^{-1}$): 3018, 2979, 2924, 2856, 1712, 1597, 1495, 1448, 1414, 1367, 1298, 1271, 1232, 1176, 1113, 1053, 1009, 958, 910, 887, 833, 798, 362, 734, 704, 507, 461.

Example 20 tert-Butyl 4-[2-(3-methanesulfonylphenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (45 mg, 0.155 mmol) and 3-methanesulfonylphenol (40 mg, 0.233 mmol) following a procedure analogous to that in Example 9 as a white crystal (22 mg, yield 39%).

FAB-MS (m/z): 447 (M+1)

$^1$H NMR (CDCl$_3$, 400 MHz): δ=1.49 (9H, s), 1.5-1.7 (2H, m), 1.8-1.9 (2H, m), 2.6-2.9 (3H, m), 3.05 (3H, s), 4.2-4.4 (2H, m), 5.23 (2H, s), 7.2-7.3 (1H, m), 7.44 (1H, d, J=8 Hz), 7.48 (1H, t, J=8 Hz), 7.5-7.6 (3H, m), 8.48 (1H, d, J=2 Hz).

IR (KBr, cm$^{-1}$): 3003, 2976, 2922, 2860, 1689, 1599, 1500, 1481, 1448, 1412, 1387, 1363, 1298, 1240, 1173, 1140, 1119, 1095, 1065, 1007, 972, 768, 681, 534, 492.

Example 21 tert-Butyl 4-[2-(4-sulfamoylphenoxymethyl)pyridin-5-yl]piperidine-1-carboxylate (1) Potassium 4-sulfamoylphenolate To a solution of 4-hydroxybenzenesulfonamide (200 mg, 1.15 mmol) in ethanol (1 mL) was added potassium hydroxide solution (0.5M in ethanol, 2.5 mL). The mixture was stirred at room temperature for 1 hour and concentrated under reduced pressure to give the title compound as a pale orange crystal (quantitative yield).

(2) tert-Butyl 4-[2-(4-sulfamoylphenoxymethyl)pyridin-5-yl]piperidine-1-carboxylate To a solution of tert-butyl 4-[2-(methanesulfonyloxymethyl)pyridin-5-yl]piperidine-1-carboxylate (Example 1(3)) (24 mg, 0.065 mmol) in dimethyl sulfoxide (1 mL) was added potassium 4-sulfamoylphenolate (14 mg, 0.065 mmol). The mixture was stirred at room temperature for 3.5 hours, to which was added saturated aqueous ammonium chloride solution and extracted with chloroform. The organic layer was washed with brine, dried over anhydrous sodium sulfate and concentrated under reduced pressure. The residue was purified by silica gel column chromatography (hexane/ethyl acetate=1/8 and chloroform/methanol=200/1→20/1) to give the title compound as a white crystal (16 mg, yield 54%).

FAB-MS (m/z): 448 (M+1)

$^1$H NMR (CDCl$_3$, 400 MHz): δ=1.48 (9H, s), 1.5-1.7 (2H, m), 1.8-1.9 (2H, m), 2.6-2.9 (3H, m), 4.2-4.4 (2H, m), 4.9-5.1 (2H, m), 5.21 (2H, s), 7.05 (2H, d, J=9 Hz), 7.42 (1H, d, J=8 Hz), 7.56 (1H, dd, J=2 Hz, 8 Hz), 7.85 (2H, d, J=9 Hz), 8.47 (1H, d, J=2 Hz).

IR (KBr, cm$^{-1}$): 3329, 3005, 2981, 2858, 1676, 1593, 1576, 1496, 1450, 1414, 1365, 1331, 1313, 1277, 1240, 1159, 1120, 1097, 1014, 989, 947, 897, 858, 839, 777, 627, 579, 548.

Example 22 tert-Butyl 4-[2-(4-methanesulfonyl-2-methylphenoxymethyl) pyridin-5-yl]piperidine-1-carboxylate The title compound was prepared from tert-butyl 4-[(2-hydroxymethyl)pyridin-5-yl]piperidine-1-carboxylate (Example 1(2)) (39 mg, 0.135 mmol) and 4-methanesulfonyl-2-methylphenol (38 mg, 0.203 mmol) following a procedure analogous to that in Example 9 as a white crystal (16 mg, yield 26%).

FAB-MS (m/z): 461 (M+1)

$^1$H NMR (CDCl$_3$, 400 MHz): δ=1.49 (9H, s), 1.5-1.7 (2H, m), 1.8-1.9 (2H, m), 2.37 (3H, s), 2.6-2.9 (3H, m), 3.02 (3H, s), 4.2-4.4 (2H, m), 5.27 (2H, s), 6.99 (1H, d, J=9 Hz), 7.43 (1H, d, J=8 Hz), 7.57 (1H, dd, J=2 Hz, 8 Hz), 7.7-7.8 (2H, m), 8.47 (1H, d, J=2 Hz).

IR (KBr, cm$^{-1}$): 3008, 2978, 2925, 2856, 1689, 1595, 1498, 1450, 1427, 1365, 1321, 1298, 1269, 1236, 1173, 1124, 1095, 1045, 1012, 972, 887, 822, 769, 642, 619, 582, 532, 496.

Example 23 tert-Butyl 4-[2-(4-dimethylsulfamoylphenoxymethyl)-pyridin-5-yl]piperidine-1-carboxylate (1) Potassium 4-(N,N-dimethylsulfamoyl)phenolate The title compound was prepared from 4-hydroxy-N,N-dimethylbenzenesulfonamide (46 mg, 0.227 mmol) following a procedure analogous to that in Example 21(1) as a pale yellow crystal (quantitative yield).

(2) tert-Butyl 4-[2-(4-dimethylsulfamoylphenoxymethyl)-pyridin-5-yl]piperidine-1-carboxylate The title compound was prepared from potassium 4-(N,N-dimethylsulfamoyl)phenolate (45 mg, 0.188 mmol) following a procedure analogous to that in Example 21(2) as a pale yellow crystal (14 mg, yield 16%).
FAB-MS (m/z): 476 (M+1)
$^1$H NMR (CDCl$_3$, 400 MHz): δ=1.49 (9H, s), 1.5-1.7 (2H, m), 1.8-1.9 (2H, m), 2.69 (6H, s), 2.6-2.9 (3H, m), 4.2-4.4 (2H, m), 5.23 (2H, s), 7.10 (2H, d, J=9 Hz), 7.43 (1H, d, J=8 Hz), 7.56 (1H, dd, J=2 Hz, 8 Hz), 7.72 (2H, d, J=9 Hz), 8.48 (1H, d, J=2 Hz).
IR (KBr, cm$^{-1}$): 2978, 2912, 2854, 1695, 1599, 1500, 1450, 1402, 1367, 1336, 1306, 1273, 1240, 1178, 1159, 1120, 1093, 1061, 1026, 950, 833, 777, 741, 712, 681, 623, 573, 538.

Example 24 tert-Butyl 4-[2-(4-methanesulfonylphenoxymethyl)pyridin-5-yl]-3,6-dihydro-2H-pyridine-1-carboxylate (1) tert-Butyl 4-[(2-hydroxymethyl)pyridin-5-yl]-3,6-dihydro-2H-pyridine-1-carboxylate The title compound was prepared from 5-bromopyridin-2-methanol (1.00 g, 5.32 mmol) and tert-butyl 4-(4,4,5,5-tetramethyl-1,3,2-dioxaborolan-2-yl)-3,6-dihydro-2H-pyridine-1-carboxylate (1.64 g, 5.32 mmol) following a procedure analogous to that in Example 1(1) as a pale yellow oil (1.33 g, yield 86%).
FAB-MS (m/z): 445 (M+1)
$^1$H NMR (CDCl$_3$, 400 MHz): δ=1.50 (9H, s), 2.4-2.6 (2H, m), 3.6-3.7 (2H, m), 4.0-4.2 (2H, m), 4.76 (2H, s), 6.0-6.2 (1H, m), 7.22 (1H, d, J=8 Hz), 7.65 (1H, dd, J=2 Hz, 8 Hz), 8.58 (1H, brs).

(2) tert-Butyl 4-[2-(4-methanesulfonylphenoxymethyl)-pyridin-5-yl]-3,6-dihydro-2H-pyridine-1-carboxylate The title compound was prepared from tert-butyl 4-[(2-hydroxymethyl)pyridin-5-yl]-3,6-dihydro-2H-pyridine-1-carboxylate (30 mg, 0.103 mmol) following a procedure analogous to that in Example 9 as a white crystal (6.1 mg, yield 13%).
FAB-MS (m/z): 445 (M+1)
$^1$H NMR (CDCl$_3$, 400 MHz): δ=1.50 (9H, s), 2.5-2.6 (2H, m), 3.03 (3H, s), 3.6-3.7 (2H, m), 4.0-4.2 (2H, m), 5.27 (2H, s), 6.1-6.2 (1H, m), 7.11 (2H, d, J=9 Hz), 7.43 (1H, d, J=8 Hz), 7.69 (1H, dd, J=2 Hz, 8 Hz), 7.87 (2H, d, J=9 Hz), 8.64 (1H, brs).
IR (KBr, cm$^{-1}$): 3003, 2979, 2921, 2854, 1697, 1653, 1593, 1498, 1456, 1410, 1365, 1296, 1238, 1169, 1140, 1111, 1061, 1038, 972, 860, 833, 810, 773, 552, 528.

Example 25 tert-Butyl 4-[2-(2-chloro-4-methanesulfonylphenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (33 mg, 0.114 mmol) and 2-chloro-4-methanesulfonylphenol (35 mg, 0.171 mmol) following a procedure analogous to that in Example 9 as a white crystal (23 mg, yield 42%).
FAB-MS (m/z): 481 (M+1)
$^1$H NMR (CDCl$_3$, 400 MHz): δ=1.49 (9H, s), 1.5-1.7 (2H, m), 1.8-1.9 (2H, m), 2.6-2.9 (3H, m), 3.04 (3H, s), 4.2-4.4 (2H, m), 5.34 (2H, s), 7.14 (1H, d, J=8 Hz), 7.52 (1H, d, J=8 Hz), 7.58 (1H, dd, J=2 Hz, 8 Hz), 7.79 (1H, dd, J=2 Hz, 8 Hz), 7.98 (1H, d, J=2 Hz), 8.47 (1H, brs).
IR (KBr, cm$^{-1}$): 2974, 2929, 2854, 1689, 1585, 1495, 1456, 1423, 1394, 1365, 1317, 1234, 1151, 1101, 1065, 1016, 964, 862, 769, 739, 584, 528, 491.

Example 26 tert-Butyl 4-[2-(4-methanesulfonyl-2-methoxyphenoxymethyl)pyridin-5-yl]piperidine-1-carboxylate (1) 4-Methanesulfonyl-2-methoxyphenol A mixture of 4-bromo-2-methoxyphenol (500 mg, 2.46 mmol), sodium methanesulfinate (1 g, 9.84 mmol), copper(I) trifluoromethanesulfonate benzene complex (124 mg, 0.25 mmol) and N,N'-dimethylethylenediamine (53 μL, 0.49 mmol) in dimethyl sulfoxide (3 mL) was stirred overnight at 130° C. The mixture was allowed to cool to room temperature followed by the addition of ethyl acetate (8 mL) and water (8 mL). The resulting mixture was filtered through Celite pad and to the filtrate was added 2N hydrochloric acid and extracted with ethyl acetate. The organic layer was washed sequentially with water and brine, dried over anhydrous sodium sulfate and concentrated under reduced pressure. The residue was purified by silica gel column chromatography (hexane/ethyl acetate=3/1→1/1) to give the title compound as a white crystal (258 mg, yield 52%).
$^1$H NMR (CDCl$_3$, 400 MHz): δ=3.04 (3H, s), 3.98 (3H, s), 6.10 (1H, s), 7.06 (1H, d, J=8 Hz), 7.41 (1H, d, J=2 Hz), 7.51 (1H, dd, J=2 Hz, 8 Hz).

(2) tert-Butyl 4-[2-(4-methanesulfonyl-2-methoxyphenoxy-methyl)pyridin-5-yl]piperidine-1-carboxylate The title compound was prepared from tert-butyl 4-[(2-hydroxymethyl)pyridin-5-yl]piperidine-1-carboxylate (Example 1(2)) (30 mg, 0.103 mmol) and 4-methanesulfonyl-2-methoxyphenol (31 mg, 0.155 mmol) following a procedure analogous to that in Example 9 as a white crystal (40 mg, yield 81%).
FAB-MS (m/z): 477 (M+1)
m.p.: 135-138° C.
$^1$H NMR (CDCl$_3$, 400 MHz): δ=1.48 (9H, s), 1.5-1.7 (2H, m), 1.8-1.9 (2H, m), 2.6-2.9 (3H, m), 3.04 (3H, s), 3.97 (3H, s), 4.2-4.4 (2H, m), 5.32 (2H, s), 7.03 (1H, d, J=8 Hz), 7.4-7.5 (3H, m), 7.54 (1H, dd, J=2 Hz, 8 Hz), 8.47 (1H, brs).
IR (KBr, cm$^{-1}$): 2974, 2925, 2852, 1685, 1587, 1508, 1458, 1425, 1404, 1363, 1308, 1261, 1234, 1169, 1134, 1092, 1020, 968, 893, 858, 764, 606, 541, 495.

Example 27 tert-Butyl 4-[2-(4-methanesulfonyl-2-trifluoromethyl-phenoxymethyl)pyridin-5-yl]piperidine-1-carboxylate (1) 4-Methanesulfonyl-2-trifluoromethylphenol The title compound was prepared from 4-bromo-2-trifluoromethylphenol (316 mg, 1.31 mmol) following a procedure analogous to that in Example 26(1) (90 mg, yield 29%).

$^1$H NMR (CD$_3$OD, 400 MHz): δ=3.11 (3H, s), 7.14 (1H, d, J=9 Hz), 7.98 (1H, dd, J=2 Hz, 9 Hz), 8.05 (1H, d, J=2 Hz).

(2) tert-Butyl 4-[2-(4-methanesulfonyl-2-trifluoromethylphenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (40 mg, 0.137 mmol) and 4-methanesulfonyl-2-trifluoromethylphenol (49 mg, 0.205 mmol) following a procedure analogous to that in Example 9 as a white crystal (24 mg, yield 35%).
FAB-MS (m/z): 447 (M+1)
$^1$H NMR (CDCl$_3$, 400 MHz): δ=1.48 (9H, s), 1.5-1.7 (2H, m), 1.7-1.9 (2H, m), 2.6-2.9 (3H, m), 3.06 (3H, s), 4.1-4.4 (2H, m), 5.38 (2H, s), 7.25 (1H, d, J=9 Hz), 7.48 (1H, d, J=8 Hz), 7.58 (1H, dd, J=2 Hz, 8 Hz), 8.06 (1H, dd, J=2 Hz, 9 Hz), 8.19 (1H, brs), 8.46 (1H, brs).
IR (KBr, cm$^{-1}$): 2978, 2927, 2860, 1741, 1697, 1614, 1498, 1456, 1427, 1369, 1308, 1284, 1286, 1147, 1126, 1099, 1059, 1012, 968, 910, 862, 845, 820, 796, 766, 698, 623, 553, 532, 492.

Example 28 tert-Butyl 4-[2-(2-acetyl-4-methanesulfonylphenoxymethyl)pyridin-5-yl]piperidine-1-carboxylate The title compound was prepared from tert-butyl 4-[(5-hydroxymethyl)pyridin-2-yl]piperidine-1-carboxylate (Example 1(2)) (36 mg, 0.123 mmol) and 2-hydroxy-5-methanesulfonylacetophenone (40 mg, 0.187 mmol) following a procedure analogous to that in Example 9 as a white amorphous (35 mg, yield 58%).
FAB-MS (m/z): 489 (M+1)
$^1$H NMR (CDCl$_3$, 400 MHz): δ=1.48 (9H, s), 1.5-1.7 (2H, m), 1.8-1.9 (2H, m), 2.67 (3H, s), 2.6-2.9 (3H, m), 3.05 (3H, s), 4.1-4.4 (2H, m), 5.37 (2H, s), 7.22 (1H, d, J=8 Hz), 7.41 (1H, d, J=8 Hz), 7.58 (1H, dd, J=2 Hz, 8 Hz), 7.99 (1H, dd, J=2 Hz, 8 Hz), 8.26 (1H, d, J=2 Hz), 8.49 (1H, d, J=2 Hz).

Example 29 tert-Butyl 4-[2-(2-ethyl-4-methanesulfonylphenoxymethyl)pyridin-5-yl]piperidine-1-carboxylate (1) 2-Ethyl-4-methanesulfonylphenol To an ice-cooled solution of aluminum chloride (172 mg, 1.29 mmol) in dry dichloromethane (4.3 mL) under N$_2$ was added borane tert-butylamine complex (224 mg, 2.57 mmol). The mixture was stirred for 10 minutes and a solution of 2-hydroxy-5-methanesulfonylacetophenone (92 mg, 0.429 mmol) in dry dichloromethane (1 mL) was added dropwise. The resulting mixture was stirred at room temperature overnight followed by the addition of 0.1M hydrochloric acid (2.2 mL) and concentrated under reduced pressure. The residue was extracted with ethyl acetate. The organic layer was washed sequentially with 0.1M hydrochloric acid and brine, dried over anhydrous sodium sulfate and concentrated under reduced pressure. The residue was purified by silica gel column chromatography (hexane/ethyl acetate=2/1) to give the title compound as a colorless oil (23 mg, yield 27%).
$^1$H NMR (CDCl$_3$, 400 MHz): δ=1.26 (3H, t, J=7 Hz), 2.69 (2H, q, J=7 Hz), 3.04 (3H, s), 6.00 (1H, brs), 6.8-6.9 (1H, m), 7.6-7.8 (2H, m).

(2) tert-Butyl 4-[2-(2-ethyl-4-methanesulfonylphenoxymethyl)pyridin-5-yl]piperidine-1-carboxylate The title compound was prepared from 2-ethyl-4-methanesulfonylphenol (20 mg, 0.10 mmol) following a procedure analogous to that in Example 1(4) as a pale yellow oil (16 mg, yield 34%).
FAB-MS (m/z): 475 (M+1)
$^1$H NMR (CDCl$_3$, 400 MHz): δ=1.28 (3H, t, J=7 Hz), 1.49 (9H, s), 1.5-1.7 (2H, m), 1.7-1.9 (2H, m), 2.6-2.9 (5H, m), 3.03 (3H, s), 4.2-4.4 (2H, m), 5.27 (2H, s), 7.00 (1H, d, J=9 Hz), 7.42 (1H, d, J=8 Hz), 7.56 (1H, dd, J=2 Hz, 8 Hz), 7.7-7.8 (2H, m), 8.48 (1H, d, J=2 Hz).

Example 30 tert-Butyl 4-[2-(3-nitrophenoxymethyl)pyridin-5-yl]piperidine-1-carboxylate

The title compound was prepared from tert-butyl 4-[(5-hydroxymethyl)pyridin-2-yl]piperidine-1-carboxylate (Example 1(2)) (150 mg, 0.517 mmol) and 3-nitrophenol (108 mg, 0.775 mmol) following a procedure analogous to that in Example 9 as a yellow crystal (147 mg, yield 69%).
FAB-MS (m/z): 414 (M+1)
m.p.: 94-96° C.
$^1$H NMR (CDCl$_3$, 400 MHz): δ=1.49 (9H, s), 1.5-1.7 (2H, m), 1.7-1.9 (2H, m), 2.6-2.9 (3H, m), 4.1-4.4 (2H, m), 5.24 (2H, s), 7.2-7.4 (1H, m), 7.4-7.5 (2H, m), 7.57 (1H, dd, J=2 Hz, 8 Hz), 7.7-7.9 (2H, m), 8.49 (1H, brs).
IR (KBr, cm$^{-1}$): 2970, 2931, 2848, 1685, 1525, 1477, 1427, 1348, 1296, 1246, 1167, 1117, 1078, 1051, 1014, 989, 918, 891, 845, 814, 766, 739, 675.

Example 31 tert-Butyl 4-[2-(3-aminophenoxymethyl)pyridin-5-yl]piperidine-1-carboxylate

A suspension of zinc powder (553 mg, 8.46 mmol) and calcium chloride (16 mg, 0.144 mmol) in ethanol (2.6 mL)-water (0.6 mL) was warmed to 90° C. followed by the addition of a solution of tert-butyl 4-[2-(3-nitrophenoxymethyl)pyridin-5-yl]piperidine-1-carboxylate (Example 30) (97 mg, 0.23 mmol) in ethanol (2 mL). The mixture was stirred at 90° C. for 1.5 hours, allowed to cool to room temperature and filtered through Celite pad. The filtrate was extracted with ethyl acetate. The organic layer was washed sequentially with water and brine, dried over anhydrous sodium sulfate and concentrated under reduced pressure. The residue was purified by silica gel column chromatography (chloroform/methanol=100/1→100/2) to give the title compound (84 mg, yield 94%).
FAB-MS (m/z): 384 (M+1)
$^1$H NMR (CDCl$_3$, 400 MHz): δ=1.49 (9H, s), 1.5-1.7 (2H, m), 1.7-1.9 (2H, m), 2.6-2.9 (3H, m), 3.66 (2H, brs), 4.1-4.4 (2H, m), 5.14 (2H, s), 6.2-6.5 (3H, m), 7.05 (1H, t, J=8 Hz), 7.45 (1H, d, J=8 Hz), 7.53 (1H, dd, J=1 Hz, 8 Hz), 8.44 (1H, brs).

Example 32 tert-Butyl 4-[2-(3-methanesulfonylaminophenoxymethyl)-pyridin-5-yl]piperidine-1-carboxylate The title compound was prepared from tert-butyl 4-[2-(3-aminophenoxymethyl)pyridin-5-yl]piperidine-1-carboxylate (Example 31) (20 mg, 0.051 mmol) following a procedure analogous to that in Example 1(3) as a pale yellow amorphous (18 mg, yield 74%).

FAB-MS (m/z): 462 (M+1)

$^1$H NMR (CDCl$_3$, 400 MHz): δ=1.49 (9H, s), 1.5-1.7 (2H, m), 1.7-1.9 (2H, m), 2.6-2.9 (3H, m), 3.00 (3H, s), 4.1-4.4 (2H, m), 5.17 (2H, s), 6.48 (1H, brs), 6.7-6.9 (2H, m), 6.90 (1H, t, J=2 Hz), 7.2-7.3 (1H, m), 7.45 (1H, d, J=8 Hz), 7.55 (1H, dd, J=2 Hz, 8 Hz), 8.47 (1H, d, J=2 Hz).

Example 33 tert-Butyl 4-[2-(4-nitrophenoxymethyl)pyridin-5-yl]-piperidine-1-carboxylate

The title compound was prepared from tert-butyl 4-[(5-hydroxymethyl)pyridin-2-yl]piperidine-1-carboxylate (Example 1(2)) (150 mg, 0.517 mmol) and 4-nitrophenol (108 mg, 0.775 mmol) following a procedure analogous to that in Example 9 as a pale yellow crystal (75 mg, yield 35%).

FAB-MS (m/z): 414 (M+1)

m.p.: 149-150° C.

$^1$H NMR (CDCl$_3$, 400 MHz): δ=1.48 (9H, s), 1.5-1.7 (2H, m), 1.8-1.9 (2H, m), 2.6-2.9 (3H, m), 4.2-4.4 (2H, m), 5.26 (2H, s), 7.06 (2H, d, J=9 Hz), 7.42 (1H, d, J=8 Hz), 7.56 (1H, dd, J=2 Hz, 8 Hz), 8.20 (2H, d, J=9 Hz), 8.49 (1H, d, J=2 Hz).

IR (KBr, cm$^{-1}$): 2972, 2912, 2837, 1685, 1591, 1510, 1450, 1417, 1365, 1333, 1279, 1259, 1232, 1167, 1117, 1084, 1045, 1020, 989, 944, 887, 860, 840, 818, 771, 752, 675.

Example 34 tert-Butyl 4-[2-(4-aminophenoxymethyl)pyridin-5-yl]-piperidine-1-carboxylate

The title compound was prepared from tert-butyl 4-[2-(4-nitrophenoxymethyl)pyridin-5-yl]piperidine-1-carboxylate (Example 33) (103 mg, 0.249 mmol) following a procedure analogous to that in Example 31 as a yellow oil (98 mg, yield 100%).

$^1$H NMR (CDCl$_3$, 400 MHz): δ=1.49 (9H, s), 1.5-1.7 (2H, m), 1.7-1.9 (2H, m), 2.6-2.9 (3H, m), 3.5-3.8 (2H, m), 4.1-4.4 (2H, m), 5.14 (2H, s), 6.68 (2H, d, J=9 Hz), 6.82 (2H, d, J=9 Hz), 7.46 (1H, d, J=8 Hz), 7.53 (1H, dd, J=2 Hz, 8 Hz), 8.45 (1H, d, J=2 Hz).

Example 35 tert-Butyl 4-[2-(4-methanesulfonylaminophenoxymethyl)-pyridin-5-yl]piperidine-1-carboxylate The title compound was prepared from tert-butyl 4-[2-(4-aminophenoxymethyl)-pyridin-5-yl]piperidine-1-carboxylate (Example 34) (26 mg, 0.067 mmol) following a procedure analogous to that in Example 1(3) as a pale yellow crystal (24 mg, yield 78%).

FAB-MS (m/z): 462 (M+1)

m.p.: 171-173° C.

$^1$H NMR (CDCl$_3$, 400 MHz): δ=1.49 (9H, s), 1.5-1.7 (2H, m), 1.8-1.9 (2H, m), 2.6-2.9 (3H, m), 2.95 (3H, s), 4.2-4.4 (2H, m), 5.15 (2H, s), 6.47 (1H, brs), 6.97 (2H, d, J=9 Hz), 7.19 (2H, d, J=9 Hz), 7.44 (1H, d, J=8 Hz), 7.55 (1H, dd, J=2 Hz, 8 Hz), 8.47 (1H, d, J=2 Hz).

IR (KBr, cm$^{-1}$): 2976, 2929, 2852, 2349, 1689, 1508, 1458, 1417, 1365, 1325, 1277, 1238, 1149, 1117, 1020, 974, 835, 771, 526.

Example 36 tert-Butyl 4-[2-(2-bromo-4-methanesulfonylphenoxymethyl)-pyridin-5-yl]piperidine-1-carboxylate The title compound was prepared from tert-butyl 4-[(5-hydroxymethyl)pyridin-2-yl]piperidine-1-carboxylate (Example 1(2)) (45 mg, 0.155 mmol) and 2-bromo-4-methanesulfonylphenol (58 mg, 0.232 mmol) following a procedure analogous to that in Example 9 as a pale yellow amorphous (49 mg, yield 61%).

FAB-MS (m/z): 525 (M+1), 527 (M+3)

$^1$H NMR (CDCl$_3$, 400 MHz): δ=1.49 (9H, s), 1.5-1.7 (2H, m), 1.8-1.9 (2H, m), 2.6-2.9 (3H, m), 3.04 (3H, s), 4.2-4.4 (2H, m), 5.33 (2H, s), 7.10 (1H, d, J=9 Hz), 7.55 (1H, d, J=8 Hz), 7.59 (1H, dd, J=2 Hz, 8 Hz), 7.83 (1H, dd, J=2 Hz, 9 Hz), 8.15 (1H, d, J=2 Hz), 8.46 (1H, d, J=2 Hz).

Example 37 tert-Butyl 4-[2-[2-fluoro-4-(tetrazol-1-yl)phenoxymethyl]pyridin-5-yl]piperidine-1-carboxylate The title compound was prepared from tert-butyl 4-[(5-hydroxymethyl)pyridin-2-yl]piperidine-1-carboxylate (Example 1(2)) (96 mg, 0.33 mmol) and 1-(3-fluoro-4-hydroxyphenyl)tetrazole (61 mg, 0.33 mmol) following a procedure analogous to that in Example 9 as a pink crystal (4.6 mg, yield 3%).

FAB-MS (m/z): 455 (M+1)

$^1$H NMR (CDCl$_3$, 400 MHz): δ=1.49 (9H, s), 1.5-1.7 (2H, m), 1.8-1.9 (2H, m), 2.6-2.8 (1H, m), 2.7-2.9 (2H, m), 4.2-4.4 (2H, m), 5.32 (2H, s), 7.23 (1H, t, J=9 Hz), 7.3-7.4 (1H, m), 7.3-7.6 (2H, m), 7.59 (1H, dd, J=2 Hz, 8 Hz), 8.49 (1H, d, J=2 Hz), 8.91 (1H, s).

Example 38 tert-Butyl 4-[2-[4-(tetrazol-1-yl)-2-trifluoromethylphenoxymethyl]pyridin-5-yl]piperidine-1-carboxylate The title compound was prepared from tert-butyl 4-[(2-hydroxymethyl)pyridin-5-yl]piperidine-1-carboxylate (Example 1(2)) (64 mg, 0.22 mmol) and 1-(4-hydroxy-3-trifluoromethylphenyl)tetrazole (50 mg, 0.22 mmol) following a procedure analogous to that in Example 9 as a pale orange crystal (34 mg, yield 31%).

FAB-MS (m/z): 505 (M+1)

$^1$H NMR (CDCl$_3$, 400 MHz): δ=1.49 (9H, s), 1.5-1.7 (2H, m), 1.8-1.9 (2H, m), 2.6-2.8 (1H, m), 2.7-2.9 (2H, m), 4.2-4.4 (2H, m), 5.38 (2H, s), 7.30 (1H, d, J=9 Hz), 7.51 (1H, d, J=8 Hz), 7.60 (1H, dd, J=2 Hz, 8 Hz), 7.82 (1H, dd, J=3 Hz, 9 Hz), 7.94 (1H, d, J=3 Hz), 8.47 (1H, d, J=2 Hz), 8.94 (1H, s).

Example 39 tert-Butyl 4-[2-[2-chloro-4-(tetrazol-1-yl)phenoxymethyl]pyridin-5-yl]piperidine-1-carboxylate The title compound was prepared from tert-butyl 4-[(2-hydroxymethyl)pyridin-5-yl]piperidine-1-carboxylate (Example 1(2)) (75 mg, 0.26 mmol) and 1-(3-chloro-4-hydroxyphenyl)tetrazole (50 mg, 0.25 mmol) following a procedure analogous to that in Example 9 as a pink crystal (23 mg, yield 20%).

FAB-MS (m/z): 471 (M+1)
$^1$H NMR (CDCl$_3$, 400 MHz): δ=1.49 (9H, s), 1.5-1.7 (2H, m), 1.8-1.9 (2H, m), 2.6-2.8 (1H, m), 2.7-2.9 (2H, m), 4.2-4.4 (2H, m), 5.34 (2H, s), 7.19 (1H, d, J=9 Hz), 7.5-7.7 (3H, m), 7.79 (1H, d, J=2 Hz), 8.47 (1H, s), 8.90 (1H, s).

Example 40 tert-Butyl 4-[2-[2-methyl-4-(tetrazol-1-yl)phenoxymethyl]pyridin-5-yl]piperidine-1-carboxylate The title compound was prepared from tert-butyl 4-[(2-hydroxymethyl)pyridin-5-yl]piperidine-1-carboxylate (Example 1(2)) (75 mg, 0.26 mmol) and 1-(3-methyl-4-hydroxyphenyl)tetrazole (51 mg, 0.29 mmol) following a procedure analogous to that in Example 9 as a pink crystal (15 mg, yield 12%).
FAB-MS (m/z): 451 (M+1)
$^1$H NMR (CDCl$_3$, 400 MHz): δ=1.49 (9H, s), 1.5-1.7 (2H, m), 1.8-1.9 (2H, m), 2.41 (3H, s), 2.6-2.8 (1H, m), 2.7-2.9 (2H, m), 4.2-4.4 (2H, m), 5.27 (2H, s), 7.02 (1H, d, J=9 Hz), 7.43 (1H, dd, J=2 Hz, 9 Hz), 7.47 (1H, d, J=8 Hz), 7.50 (1H, s), 7.58 (1H, dd, J=2 Hz, 8 Hz), 8.49 (1H, d, J=1 Hz), 8.89 (1H, s).

Example 41

1,1-Dimethylpropyl 4-[2-(4-methanesulfonylphenoxymethyl)-pyridin-5-yl]piperidine-1-carboxylate To a solution of tert-butyl 4-[2-(4-methanesulfonyl-phenoxymethyl)pyridin-5-yl]piperidine-1-carboxylate (Example 1) (30 mg, 0.067 mmol) in dry dichloromethane (0.35 mL) under N$_2$ was added trifluoroacetic acid (0.35 mL). The mixture was stirred at room temperature for 2 hours and concentrated in vacuo. To a solution of the residue in dry tetrahydrofuran (0.7 mL) was added triethylamine (28 μL, 0.2 mmol) and di-tert-amyl dicarbonate (25 μL, 0.1 mmol). The mixture was stirred at room temperature for 3 hours, diluted with water (1 mL) and extracted with ethyl acetate. The organic layer was washed with brine, dried over anhydrous sodium sulfate and concentrated under reduced pressure. The residue was purified by silica gel column chromatography (hexane/ethyl acetate=1/1) to give the title compound as a white crystal (28 mg, yield 91%).
FAB-MS (m/z): 461 (M+1)
m.p.: 114-115° C.
$^1$H NMR (CDCl$_3$, 400 MHz): δ=0.91 (3H, t, J=8 Hz), 1.45 (6H, s), 1.6-1.7 (2H, m), 1.8-1.9 (4H, m), 2.7-2.8 (3H, m), 3.03 (3H, s), 4.26 (2H, m), 5.25 (2H, s), 7.11 (2H, d, J=9 Hz), 7.41 (1H, d, J=8 Hz), 7.55 (1H, dd, J=2 Hz, 8 Hz), 7.86 (2H, d, J=9 Hz), 8.48 (1H, d, J=2 Hz).
IR (KBr, cm$^{-1}$): 2974, 2925, 2858, 1687, 1593, 1498, 1466, 1427, 1365, 1313, 1292, 1228, 1165, 1140, 1093, 1049, 1011, 968, 941, 837, 773, 615, 550, 526.

Example 42

Benzyl 4-[2-(4-methanesulfonylphenoxymethyl)pyridin-5-yl]piperidine-1-carboxylate The title compound was prepared from tert-butyl 4-[2-(4-methanesulfonylphenoxymethyl)pyridin-5-yl]piperidine-1-carboxylate (Example 1) (30 mg, 0.067 mmol) following a procedure analogous to that in Example 41 as a white amorphous (24 mg, yield 73%).
FAB-MS (m/z): 481 (M+1)
$^1$H NMR (CDCl$_3$, 400 MHz): δ=1.6-1.8 (2H, m), 1.8-2.0 (2H, m), 2.7-2.8 (1H, m), 2.8-3.0 (2H, m), 3.03 (3H, s), 4.2-4.5 (2H, m), 5.16 (2H, s), 5.25 (2H, s), 7.12 (2H, d, J=9 Hz), 7.3-7.5 (6H, m), 7.55 (1H, dd, J=2 Hz, 8 Hz), 7.87 (2H, d, J=9 Hz), 8.48 (1H, d, J=2 Hz).

Example 43

Ethyl 4-[2-(4-methanesulfonylphenoxymethyl)pyridin-5-yl]piperidine-1-carboxylate The title compound was prepared from tert-butyl 4-[2-(4-methanesulfonylphenoxymethyl)pyridin-5-yl]piperidine-1-carboxylate (Example 1) (30 mg, 0.067 mmol) following a procedure analogous to that in Example 41 as a white crystal (20 mg, yield 69%).
FAB-MS (m/z): 419 (M+1)
m.p.: 119-121° C.
$^1$H NMR (CDCl$_3$, 400 MHz): δ=1.28 (3H, t, J=7 Hz), 1.5-1.7 (2H, m), 1.8-1.9 (2H, m), 2.7-2.8 (1H, m), 2.8-3.0 (2H, m), 3.03 (3H, s), 4.16 (2H, q, J=7 Hz), 4.2-4.4 (2H, m), 5.25 (2H, s), 7.12 (2H, d, J=9 Hz), 7.42 (1H, d, J=8 Hz), 7.56 (1H, dd, J=2 Hz, 8 Hz), 7.87 (2H, d, J=9 Hz), 8.48 (1H, d, J=2 Hz).
IR (KBr, cm$^{-1}$): 2925, 2854, 1693, 1595, 1579, 1498, 1437, 1385, 1292, 1230, 1142, 1093, 1034, 970, 839, 773, 546, 526.

Example 44

Isobutyl 4-[2-(4-methanesulfonylphenoxymethyl)pyridin-5-yl]piperidine-1-carboxylate The title compound was prepared from tert-butyl 4-[2-(4-methanesulfonylphenoxymethyl)pyridin-5-yl]piperidine-1-carboxylate (Example 1) (30 mg, 0.067 mmol) following a procedure analogous to that in Example 41 as a white crystal (23 mg, yield 77%).
FAB-MS (m/z): 447 (M+1)
m.p.: 114-117° C.
$^1$H NMR (CDCl$_3$, 400 MHz): δ=0.95 (6H, d, J=7 Hz), 1.5-1.8 (2H, m), 1.8-1.9 (2H, m), 1.9-2.0 (1H, m), 2.7-2.8 (1H, m), 2.8-3.0 (2H, m), 3.03 (3H, s), 3.90 (2H, d, J=7 Hz), 4.2-4.4 (2H, m), 5.25 (2H, s), 7.12 (2H, d, J=9 Hz), 7.42 (1H, d, J=8 Hz), 7.56 (1H, dd, J=2 Hz, 8 Hz), 7.87 (2H, d, J=9 Hz), 8.49 (1H, d, J=2 Hz).
IR (KBr, cm$^{-1}$): 2960, 2929, 2873, 1691, 1593, 1577, 1498, 1469, 1437, 1389, 1313, 1290, 1269, 1248, 1228, 1140, 1120, 1093, 1047, 968, 837, 775, 550, 528.

Example 45

1-Methylcyclopropyl-4-[2-(4-methanesulfonyl-2-trifluoromethylphenoxymethyl)pyridin-5-yl]piperidine-1-carboxylate The title compound was prepared from tert-butyl 4-[2-(4-methanesulfonylphenoxymethyl)pyridin-5-yl]piperidine-1-carboxylate (Example 1) (28 mg, 0.063 mmol) following a procedure analogous to that in Example 41 as a white crystal (19 mg, yield 68%).
FAB-MS (m/z): 445 (M+1)
$^1$H NMR (CDCl$_3$, 400 MHz): δ=0.6-0.8 (2H, m), 0.8-1.0 (2H, m), 1.57 (3H, s), 1.5-1.8 (2H, m), 1.8-2.0 (2H, m), 2.6-2.9 (3H, m), 3.03 (3H, s), 4.0-4.4 (2H, m), 5.25 (2H, s), 7.11 (2H, d, J=9 Hz), 7.42 (1H, d, J=8 Hz), 7.55 (1H, dd, J=2 Hz, 8 Hz), 7.87 (2H, d, J=9 Hz), 8.48 (1H, d, J=2 Hz).

Example 46

1-[4-[2-(4-Methanesulfonylphenoxymethyl)pyridin-5-yl]piperidin-1-yl]-3,3-dimethylbutan-1-one The title compound was prepared from tert-butyl 4-[2-(4-methanesulfonylphenoxymethyl)pyridin-5-yl]piperidine-1-carboxylate (Example 1) (30 mg, 0.067 mmol) and 3,3-dimethylbutyryl chloride (14 µL, 0.1 mmol) following a procedure analogous to that in Example 41 as a white crystal (28 mg, yield 94%).
FAB-MS (m/z): 445 (M+1)
m.p.: 140-142° C.
$^1$H NMR (CDCl$_3$, 400 MHz): δ=1.08 (9H, s), 1.6-1.7 (2H, m), 1.9-2.0 (2H, m), 2.2-2.4 (2H, m), 2.6-2.7 (1H, m), 2.7-2.8 (1H, m), 3.03 (3H, s), 3.1-3.2 (1H, m), 4.0-4.2 (1H, m), 4.8-5.0 (1H, m), 5.25 (2H, s), 7.12 (2H, d, J=9 Hz), 7.42 (1H, d, J=8 Hz), 7.55 (1H, dd, J=2 Hz, 8 Hz), 7.86 (2H, d, J=9 Hz), 8.58 (1H, d, J=2 Hz).
IR (KBr, cm$^{-1}$): 2952, 2925, 2366, 1633, 1593, 1498, 1419, 1365, 1317, 1298, 1254, 1146, 1095, 1051, 1007, 962, 833, 769, 544.

Example 47

1-[4-[2-(4-Methanesulfonylphenoxymethyl)pyridin-5-yl]piperidin-1-yl]-2-methylpropan-1-one The title compound was prepared from tert-butyl 4-[2-(4-methanesulfonylphenoxymethyl)pyridin-5-yl]piperidine-1-carboxylate (Example 1) following a procedure analogous to that in Example 41 as a pale brown crystal.
FAB-MS (m/z): 417 (M+1)
$^1$H NMR (CDCl$_3$, 400 MHz): δ=1.15 (6H, brs), 1.5-1.7 (2H, m), 1.8-2.0 (2H, m), 2.5-2.7 (1H, m), 2.7-2.9 (2H, m), 3.03 (3H, s), 3.1-3.3 (1H, m), 4.0-4.2 (1H, m), 4.8-4.9 (1H, m), 5.26 (2H, s), 7.12 (2H, d, J=9 Hz), 7.44 (1H, d, J=8 Hz), 7.57 (1H, dd, J=2 Hz, 8 Hz), 7.87 (2H, d, J=9 Hz), 8.49 (1H, d, J=2 Hz).

Example 48

5-Ethyl-2-[4-[2-(4-methanesulfonylphenoxymethyl)pyridin-5-yl]piperidin-1-yl]pyrimidine To a solution of tert-butyl 4-[2-(4-methanesulfonylphenoxymethyl)pyridin-5-yl]piperidine-1-carboxylate (Example 1) (50 mg, 0.11 mmol) in dry dichloromethane (0.55 mL) was added trifluoroacetic acid (0.55 mL). The mixture was stirred at room temperature for 2 hours and concentrated in vacuo.
To a solution of the residue in dry acetonitrile (1 mL) was added potassium carbonate (76 mg, 0.55 mmol) and 5-ethyl-2-bromopyrimidine (26 µL, 0.22 mmol). The mixture was stirred at 80° C. for 18 hours, allowed to cool to room temperature, diluted with water (1 mL) and extracted with ethyl acetate. The organic layer was washed with brine, dried over anhydrous sodium sulfate and concentrated under reduced pressure. The residue was purified by silica gel column chromatography (hexane/ethyl acetate=1/2) to give the title compound as a white crystal (35 mg, yield 70%).
FAB-MS (m/z): 453 (M+1)
m.p.: 185-187° C.
$^1$H NMR (CDCl$_3$, 400 MHz): δ=1.20 (3H, t, J=8 Hz), 1.7-1.8 (2H, m), 1.8-2.0 (2H, m), 2.48 (2H, q, J=8 Hz), 2.8-2.9 (1H, m), 2.9-3.1 (2H, m), 3.03 (3H, s), 4.8-5.0 (2H, m), 5.25 (2H, s), 7.11 (2H, d, J=9 Hz), 7.40 (1H, d, J=8 Hz), 7.56 (1H, dd, J=2 Hz, 8 Hz), 7.86 (2H, d, J=9 Hz), 8.19 (2H, s), 8.51 (1H, d, J=2 Hz).
IR (KBr, cm$^{-1}$): 2997, 2917, 1844, 1732, 1604, 1536, 1500, 1456, 1408, 1361, 1317, 1296, 1271, 1241, 1178, 1147, 1093, 1043, 1009, 966, 947, 827, 795, 771, 739, 658, 627, 538, 486, 407.

Example 49

2-[4-[2-(4-Methanesulfonylphenoxymethyl)pyridin-5-yl]piperidin-1-yl]-5-propylpyrimidine The title compound was prepared from tort-butyl 4-[2-(4-methanesulfonylphenoxymethyl)pyridin-5-yl]piperidine-1-carboxylate (Example 1) (50 mg, 0.11 mmol) and 5-propyl-2-bromopyrimidine (26 µL, 0.22 mmol) following a procedure analogous to that in Example 48 as a white crystal (31 mg, yield 60%).
FAB-MS (m/z): 467 (M+1)
m.p.: 164-166° C.
$^1$H NMR (CDCl$_3$, 400 MHz): δ=0.94 (3H, t, J=7 Hz), 1.5-1.6 (2H, m), 1.6-1.8 (2H, m), 1.9-2.0 (2H, m), 2.41 (2H, t, J=7 Hz), 2.8-2.9 (1H, m), 2.9-3.1 (2H, m), 3.03 (3H, s), 4.9-5.0 (2H, m), 5.25 (2H, s), 7.11 (2H, d, J=9 Hz), 7.41 (1H, d, J=8 Hz), 7.58 (1H, dd, J=2 Hz, 8 Hz), 7.86 (2H, d, J=9 Hz), 8.17 (2H, s), 8.50 (1H, d, J=2 Hz).
IR (KBr, cm$^{-1}$): 2958, 2927, 2852, 2359, 2322, 1603, 1541, 1481, 1458, 1369, 1302, 1254, 1174, 1147, 1093, 1047, 1014, 964, 947, 841, 798, 769, 739, 629, 528, 492, 418.

Example 50

2-[4-[2-(4-Methanesulfonylphenoxymethyl)pyridin-5-yl]piperidin-1-yl]-5-pentylpyrimidine The title compound was prepared from tert-butyl 4-[2-(4-methanesulfonylphenoxymethyl)pyridin-5-yl]piperidine-1-carboxylate (Example 1) (50 mg, 0.11 mmol) and 5-pentyl-2-bromopyrimidine (37 µL, 0.22 mmol) following a procedure analogous to that in Example 48 as a white crystal (35 mg, yield 64%).
FAB-MS (m/z): 495 (M+1)
m.p.: 154-157° C.
$^1$H NMR (CDCl$_3$, 400 MHz): δ=0.89 (3H, t, J=7 Hz), 1.3-1.4 (4H, m), 1.4-1.6 (2H, m), 1.6-1.8 (2H, m), 1.9-2.0 (2H, m), 2.42 (2H, t, J=7 Hz), 2.8-2.9 (1H, m), 2.9-3.1 (2H, m), 3.03 (3H, s), 4.9-5.0 (2H, m), 5.25 (2H, s), 7.12 (2H, d, J=9 Hz), 7.41 (1H, d, J=8 Hz), 7.57 (1H, dd, J=2 Hz, 8 Hz), 7.86 (2H, d, J=9 Hz), 8.17 (2H, s), 8.51 (1H, d, J=2 Hz).
IR (KBr, cm$^{-1}$): 2952, 2925, 2852, 2360, 2322, 1601, 1541, 1489, 1456, 1363, 1298, 1250, 1149, 1093, 1053, 1012, 958, 839, 798, 771, 638, 532, 488.

Example 51

5-Ethyl-2-[4-[2-[4-(tetrazol-1-yl)phenoxymethyl]pyridin-5-yl]piperidin-1-yl]pyrimidine The title compound was prepared from tort-butyl 4-[2-[4-(tetrazol-1-yl)phenoxymethyl]pyridin-5-yl]piperidine-1-carboxylate (Example 17) (26 mg, 0.06 mmol) and 5-ethyl- 2-bromopyrimidine (14 μL, 0.12 mmol) following a procedure analogous to that in Example 48 as a white crystal (10 mg, yield 38%).

FAB-MS (m/z): 437 (M+1)

$^1$H NMR (CDCl$_3$, 400 MHz): δ=1.26 (3H, t, J=7 Hz), 1.6-1.8 (2H, m), 1.9-2.0 (2H, m), 2.47 (2H, q, J=7 Hz), 2.8-2.9 (1H, m), 2.9-3.0 (2H, m), 4.8-5.0 (2H, m), 5.25 (2H, s), 7.16 (2H, d, J=9 Hz), 7.44 (1H, d, J=8 Hz), 7.5-7.6 (3H, m), 8.20 (2H, s), 8.51 (1H, d, J=2 Hz), 8.88 (1H, s).

Example 52

2-[4-[2-(4-Cyano-3-fluorophenoxymethyl)pyridin-5-yl]piperidin-1-yl]-5-ethylpyrimidine The title compound was prepared from tert-butyl 4-[2-(4-cyano-3-fluorophenoxymethyl)pyridin-5-yl]piperidine-1-carboxylate (Example 13) (50 mg, 0.12 mmol) and 5-ethyl-2-bromopyrimidine (29 μL, 0.24 mmol) following a procedure analogous to that in Example 48 as a white crystal (37 mg, yield 73%).

FAB-MS (m/z): 418 (M+1)

m.p.: 129-131° C.

$^1$H NMR (CDCl$_3$, 400 MHz): δ=1.20 (3H, t, J=8 Hz), 1.6-1.8 (2H, m), 1.9-2.0 (2H, m), 2.47 (2H, q, J=8 Hz), 2.8-2.9 (1H, m), 2.9-3.0 (2H, m), 4.9-5.0 (2H, m), 5.21 (2H, s), 6.8-6.9 (2H, m), 7.37 (1H, d, J=8 Hz), 7.52 (1H, t, J=8 Hz), 7.57 (1H, dd, J=2 Hz, 8 Hz), 8.19 (2H, s), 8.50 (1H, d, J=2 Hz).

IR (KBr, cm$^{-1}$): 2970, 2933, 2815, 2233, 1618, 1603, 1572, 1543, 1506, 1475, 1446, 1381, 1360, 1302, 1246, 1223, 1171, 1115, 1041, 1013, 939, 847, 816, 789, 754, 634, 507, 453, 409.

Example 53

2-[4-[2-(4-Cyano-3-fluorophenoxymethyl)pyridin-5-yl]piperidin-1-yl]-5-propylpyrimidine The title compound was prepared from tert-butyl 4-[2-(4-cyano-3-fluorophenoxymethyl)pyridin-5-yl]piperidine-1-carboxylate (Example 13) (50 mg, 0.12 mmol) and 5-propyl-2-bromopyrimidine (33 μL, 0.24 mmol) following a procedure analogous to that in Example 48 as a white crystal (35 mg, yield 67%).

FAB-MS (m/z): 431 (M+1)

m.p.: 118-120° C.

$^1$H NMR (CDCl$_3$, 400 MHz): δ=0.94 (3H, t, J=7 Hz), 1.5-1.8 (4H, m), 1.9-2.0 (2H, m), 2.41 (2H, t, J=7 Hz), 2.8-2.9 (1H, m), 2.9-3.0 (2H, m), 4.9-5.0 (2H, m), 5.21 (2H, s), 6.8-6.9 (2H, m), 7.38 (1H, d, J=8 Hz), 7.52 (1H, dd, J=8 Hz, 9 Hz), 7.57 (1H, dd, J=2 Hz, 8 Hz), 8.17 (2H, s), 8.51 (1H, d, J=2 Hz).

IR (KBr, cm$^{-1}$): 3014, 2927, 2854, 2359, 2229, 1622, 1601, 1574, 1541, 1506, 1477, 1450, 1365, 1329, 1300, 1269, 1244, 1171, 1115, 1047, 1012, 972, 943, 833, 798, 736, 627, 498.

Example 54

2-[4-[2-(4-Cyano-3-fluorophenoxymethyl)pyridin-5-yl]piperidin-1-yl]-5-pentylpyrimidine The title compound was prepared from tert-butyl 4-[2-(4-cyano-3-fluorophenoxymethyl)pyridin-5-yl]piperidine-1-carboxylate (Example 13) (33 mg, 0.08 mmol) and 5-pentyl-2-bromopyrimidine (27 μL, 0.16 mmol) following a procedure analogous to that in Example 48 as a white crystal (24 mg, yield 65%).

FAB-MS (m/z): 460 (M+1)

m.p.: 92-94° C.

$^1$H NMR (CDCl$_3$, 400 MHz): δ=0.89 (3H, t, J=7 Hz), 1.2-1.4 (4H, m), 1.5-1.6 (2H, m), 1.6-1.8 (2H, m), 1.9-2.0 (2H, m), 2.42 (2H, t, J=8 Hz), 2.8-2.9 (1H, m), 2.9-3.0 (2H, m), 4.8-5.0 (2H, m), 5.21 (2H, s), 6.7-6.9 (2H, m), 7.38 (1H, d, J=8 Hz), 7.52 (1H, dd, J=8 Hz, 9 Hz), 7.58 (1H, dd, J=2 Hz, 8 Hz), 8.17 (2H, s), 8.51 (1H, d, J=2 Hz).

IR (KBr, cm$^{-1}$): 2958, 2929, 2856, 2362, 2322, 2227, 1621, 1599, 1574, 1540, 1508, 1456, 1365, 1335, 1304, 1240, 1225, 1174, 1105, 1043, 1014, 974, 943, 843, 800, 735, 629, 505.

Example 55

5-Propyl-2-[4-[2-[4-(tetrazol-1-yl)phenoxymethyl]pyridin-5-yl]piperidin-1-yl]pyrimidine The title compound was prepared from tert-butyl 4-[2-[4-(tetrazol-1-yl)phenoxymethyl]pyridin-5-yl]piperidine-1-carboxylate (Example 17) (56 mg, 0.13 mmol) and 5-propyl-2-bromopyrimidine (36 μL, 0.26 mmol) following a procedure analogous to that in Example 48 as a white crystal (6 mg, yield 10%).

FAB-MS (m/z): 457 (M+1)

$^1$H NMR (CDCl$_3$, 400 MHz): δ=0.95 (3H, t, J=7 Hz), 1.4-1.6 (2H, m), 1.6-1.8 (2H, m), 1.9-2.0 (2H, m), 2.41 (2H, t, J=7 Hz), 2.8-3.0 (3H, m), 4.9-5.0 (2H, m), 5.25 (2H, s), 7.1-7.2 (2H, m), 7.4-7.5 (1H, m), 7.5-7.7 (3H, m), 8.18 (2H, s), 8.52 (1H, s), 8.88 (1H, s).

Example 56

5-Pentyl-2-[4-[2-[4-(tetrazol-1-yl)phenoxymethyl]pyridin-5-yl]piperidin-1-yl]pyrimidine The title compound was prepared from tert-butyl 4-[2-[4-(tetrazol-1-yl)phenoxymethyl]pyridin-5-yl]piperidine-1-carboxylate (Example 17) (52 mg, 0.12 mmol) and 5-pentyl-2-bromopyrimidine (41 μL, 0.24 mmol) following a procedure analogous to that in Example 48 as a white crystal (26 mg, yield 45%).

FAB-MS (m/z): 485 (M+1)

m.p.: 174-176° C.

$^1$H NMR (CDCl$_3$, 400 MHz): δ=0.89 (3H, t, J=7 Hz), 1.2-1.4 (4H, m), 1.4-1.6 (2H, m), 1.6-1.8 (2H, m), 1.9-2.0 (2H, m), 2.42 (2H, t, J=7 Hz), 2.8-2.9 (1H, m), 2.9-3.0 (2H, m), 4.9-5.0 (2H, m), 5.25 (2H, s), 7.16 (2H, d, J=9 Hz), 7.44 (1H, d, J=8 Hz), 7.5-7.7 (3H, m), 8.17 (2H, s), 8.51 (1H, d, J=2 Hz), 8.88 (1H, s).

IR (KBr, cm$^{-1}$): 3128, 2952, 2927, 2854, 1604, 1541, 1520, 1483, 1460, 1367, 1306, 1248, 1207, 1173, 1093, 1055, 947, 831, 796, 677, 642, 526, 496.

Example 57

5-Bromo-2-[4-[2-(4-methanesulfonylphenoxymethyl)pyridin-5-yl]piperidin-1-yl]pyrimidine The title compound was prepared from tert-butyl 4-[2-(4-methanesulfonylphenoxymethyl)pyridin-5-yl]piperidine-1-carboxylate (Example 1) (30 mg, 0.067 mmol) following a procedure analogous to that in Example 48 as a white crystal (31 mg, yield 92%).

¹H NMR (CDCl₃, 400 MHz): δ=1.6-1.8 (2H, m), 1.9-2.0 (2H, m), 2.8-2.9 (1H, m), 2.9-3.1 (2H, m), 3.03 (3H, s), 4.8-5.0 (2H, m), 5.25 (2H, s), 7.11 (2H, d, J=9 Hz), 7.42 (1H, d, J=8 Hz), 7.56 (1H, dd, J=2 Hz, 8 Hz), 7.86 (2H, d, J=9 Hz), 8.30 (2H, s), 8.58 (1H, d, J=2 Hz).

Example 58

5-Isopropenyl-2-[4-[2-(4-methanesulfonylphenoxymethyl)pyridin-5-yl]piperidin-1-yl]pyrimidine To a solution of 5-bromo-2-[4-[2-(4-methanesulfonylphenoxymethyl)pyridin-5-yl]piperidin-1-yl]pyrimidine (Example 57) (31 mg, 0.062 mmol) and isopropenylboronic acid pinacol ester (23 μL, 0.124 mmol) in dry N,N-dimethylformamide (0.3 mL) was added [1,1-bis(diphenylphosphino)ferrocene]dichloropalladium (complex with dichloromethane) (1 mg, 0.012 mmol) and cesium carbonate (40 mg, 0.124 mmol). The mixture was stirred at 90° C. overnight under N₂, allowed to cool to room temperature, diluted with water (1 mL) and extracted with ethyl acetate. The organic layer was washed with brine, dried over anhydrous sodium sulfate and concentrated under reduced pressure. The residue was purified by silica gel column chromatography (hexane/ethyl acetate=1/2) to give the title compound as a white crystal (23 mg, yield 78%).
FAB-MS (m/z): 465 (M+1)
¹H NMR (CDCl₃, 400 MHz): δ=1.6-1.8 (2H, m), 1.9-2.0 (2H, m), 2.09 (3H, s), 2.8-3.0 (3H, m), 3.02 (3H, s), 4.9-5.0 (3H, m), 5.25 (2H, s), 5.26 (1H, brs), 7.11 (2H, d, J=9 Hz), 7.41 (1H, d, J=8 Hz), 7.57 (1H, dd, J=2 Hz, 8 Hz), 7.86 (2H, d, J=9 Hz), 8.45 (2H, s), 8.50 (1H, brs).

Example 59

5-Isopropyl-2-[4-[2-(4-methanesulfonylphenoxymethyl)pyridin-5-yl]piperidin-1-yl]pyrimidine To a solution of 5-isopropenyl-2-[4-[2-(4-methanesulfonylphenoxymethyl)pyridin-5-yl]piperidin-1-yl]pyrimidine (Example 58) (21 mg, 0.045 mmol) in methanol (0.45 mL) was added 10% palladium-carbon (10 mg). The mixture was hydrogenated at room temperature for 1 hour and filtered through Celite pad. The filtrate was concentrated under reduced pressure. The residue was purified by silica gel column chromatography (hexane/ethyl acetate=1/2) to give the title compound as a white crystal (15 mg, yield 71%).
FAB-MS (m/z): 467 (M+1)
¹H NMR (CDCl₃, 400 MHz): δ=1.23 (6H, d, J=7 Hz), 1.6-1.8 (2H, m), 1.9-2.0 (2H, m), 2.7-2.9 (2H, m), 2.9-3.0 (2H, m), 3.03 (3H, s), 4.9-5.0 (2H, m), 5.25 (2H, s), 7.12 (2H, d, J=9 Hz), 7.40 (1H, d, J=8 Hz), 7.57 (1H, dd, J=2 Hz, 8 Hz), 7.87 (2H, d, J=9 Hz), 8.22 (2H, s), 8.51 (1H, d, J=2 Hz).
IR (KBr, cm⁻¹): 2958, 2920, 2852, 1597, 1541, 1496, 1458, 1362, 1313, 1302, 1254, 1230, 1176, 1149, 1095, 1051, 1014, 964, 947, 841, 804, 769, 528.

Example 60 tert-Butyl 4-[2-[2-(4-methanesulfonylphenoxyethyl)pyridine-5-yl]piperidine-1-carboxylate (1) 2-(5-Bromopyridin-2-yl)ethanol To a solution of (5-bromopyridin-2-yl)acetic acid (60.0 mg, 0.278 mmol) in dry tetrahydrofuran (1.4 mL) was added dropwise borane-tetrahydrofuran complex (1.06M in tetrahydrofuran, 0.34 mL, 0.361 mmol) under N₂. The mixture was stirred at room temperature for 19 hours and water (5 mL)-acetic acid (5 mL) was added slowly. The mixture was concentrated under reduced pressure, the residue was poured into saturated aqueous sodium hydrogen carbonate solution and extracted with ethyl acetate. The organic layer was washed with saturated aqueous sodium hydrogen carbonate solution, dried over anhydrous sodium sulfate and concentrated under reduced pressure. The residue was purified by silica gel column chromatography (hexane/ethyl acetate=7/3→ethyl acetate) to give the title compound as a yellow oil (45 mg, yield 80%).
¹H NMR (CDCl₃, 400 MHz): δ=2.98 (2H, t, J=5 Hz), 3.68 (1H, brs), 4.01 (2H, t, J=5 Hz), 7.09 (1H, d, J=8 Hz), 7.75 (1H, dd, J=2 Hz, 8 Hz), 8.57 (1H, d, J=2 Hz).

(2) tert-Butyl 4-[2-(2-hydroxyethyl)pyridin-2-yl]-3,6-dihydro-2H-pyridine-1-carboxylate The title compound was prepared from 2-(5-bromopyridin-2-yl)ethanol (202 mg, 1.00 mmol) following a procedure analogous to that in Example 3(2) as a yellow oil (310 mg, yield 99%).
¹H NMR (CDCl₃, 400 MHz): δ=1.50 (9H, s), 2.4-2.6 (2H, m), 3.01 (2H, t, J=5 Hz), 3.6-3.7 (2H, m), 4.02 (2H, t, J=5 Hz), 4.0-4.2 (2H, m), 4.15 (1H, brs), 6.06 (1H, s), 7.13 (1H, d, J=8 Hz), 7.59 (1H, dd, J=2 Hz, 8 Hz), 8.52 (1H, d, J=2 Hz).

(3) tert-Butyl 4-[2-(2-hydroxyethyl)pyridin-5-yl]piperidine-1-carboxylate

The title compound was prepared from tert-butyl 4-[2-(2-hydroxyethyl)pyridin-2-yl]-3,6-dihydro-2H-pyridine-1-carboxylate (310 mg, 1.02 mmol) following a procedure analogous to that in Example 3(3) as a yellow oil (312 mg, yield 99%).
¹H NMR (CDCl₃, 400 MHz): δ=1.48 (9H, s), 1.5-1.7 (2H, m), 1.8-1.9 (2H, m), 2.6-2.9 (3H, m), 3.05 (2H, t, J=5 Hz), 4.02 (2H, t, J=5 Hz), 4.2-4.4 (2H, m), 7.20 (1H, d, J=8 Hz), 7.55 (1H, dd, J=2 Hz, 8 Hz), 8.37 (1H, d, J=2 Hz).

(4) tert-Butyl 4-[2-[2-(4-methanesulfonylphenoxyethyl)-pyridine-5-yl]-piperidine-1-carboxylate The title compound was prepared from tert-butyl 4-[2-(2-hydroxyethyl)pyridin-5-yl]piperidine-1-carboxylate (150 mg, 0.490 mmol) following a procedure analogous to that in Example 9 as a white crystal (84 mg, yield 37%).
FAB-MS (m/z): 461 (M+1)
m.p.: 123-126° C.
¹H NMR (CDCl₃, 400 MHz): δ=1.48 (9H, s), 1.5-1.7 (2H, m), 1.7-1.9 (2H, m), 2.6-2.8 (1H, m), 2.7-2.9 (2H, m), 3.01 (3H, s), 3.26 (2H, t, J=7 Hz), 4.2-4.3 (2H, m), 4.44 (2H, t, J=7 Hz), 7.02 (2H, d, J=9 Hz), 7.20 (1H, d, J=8 Hz), 7.46 (1H, dd, J=2 Hz, 8 Hz), 7.84 (2H, d, J=9 Hz), 8.42 (1H, d, J=2 Hz).
IR (KBr, cm⁻¹): 3014, 2981, 2920, 2870, 1685, 1597, 1577, 1493, 1460, 1423, 1365, 1313, 1298, 1261, 1236, 1165, 1144, 1119, 1088, 1026, 966, 831, 808, 764, 555, 534.

Example 61 tert-Butyl 4-[2-[1-(4-methanesulfonylphenoxy)ethyl]pyridin-5-yl]piperidine-1-carboxylate (1) tert-Butyl 4-[2-(1-hydroxyethyl)pyridin-5-yl]-3,6-dihydro-2H-pyridine-1-carboxylate The title compound was prepared from 1-(5-bromopyridin-2-yl)ethanol (100 mg, 0.495 mmol) following a procedure analogous to that in Example 3(2) as a brown oil (71 mg, yield 47%).

¹H NMR (CDCl₃, 400 MHz): δ=1.50 (9H, s), 1.51 (3H, s), 2.4-2.6 (2H, m), 3.6-3.7 (2H, m), 4.0-4.2 (2H, m), 4.12 (1H, brs), 4.89 (1H, q, J=6 Hz), 6.09 (1H, brs), 7.25 (1H, d, J=8 Hz), 7.66 (1H, dd, J=2 Hz, 8 Hz), 8.55 (1H, d, J=2 Hz).

(2) tert-Butyl 4-[2-(1-hydroxyethyl)pyridin-5-yl]piperidine-1-carboxylate

The title compound was prepared from tert-butyl 4-[2-(1-hydroxyethyl)pyridin-5-yl]-3,6-dihydro-2H-pyridine-1-carboxylate (310 mg, 1.02 mmol) following a procedure analogous to that in Example 3(3) as a yellow oil (71 mg, yield 99%).

¹H NMR (CDCl₃, 400 MHz): δ=1.49 (9H, s), 1.4-1.6 (3H, m), 1.5-1.7 (2H, m), 1.8-1.9 (2H, m), 2.6-2.8 (1H, m), 2.7-2.9 (2H, m), 4.1-4.4 (3H, m), 4.87 (1H, q, J=6 Hz), 7.22 (1H, d, J=8 Hz), 7.52 (1H, dd, J=2 Hz, 8 Hz), 8.40 (1H, d, J=2 Hz).

(3) tert-Butyl 4-[2-[1-(4-methanesulfonylphenoxy)ethyl]-pyridin-5-yl]piperidine-1-carboxylate The title compound was prepared from tert-butyl 4-[2-(1-hydroxyethyl)pyridin-5-yl]piperidine-1-carboxylate (70 mg, 0.229 mmol) following a procedure analogous to that in Example 9 as a pale yellow amorphous (79 mg, yield 75%).

FAB-MS (m/z): 461 (M+1)

¹H NMR (CDCl₃, 400 MHz): δ=1.48 (9H, s), 1.5-1.7 (2H, m), 1.70 (3H, d, J=6 Hz), 1.8-1.9 (2H, m), 2.6-2.9 (3H, m), 2.99 (3H, s), 4.2-4.3 (2H, m), 5.47 (1H, q, J=6 Hz), 7.99 (2H, d, J=9 Hz), 7.30 (1H, d, J=8 Hz), 7.49 (1H, dd, J=2 Hz, 8 Hz), 7.77 (2H, d, J=9 Hz), 8.44 (1H, d, J=2 Hz).

Example 62 tert-Butyl 4-[2-(4-methanesulfonylphenoxymethyl)-3-methylpyridin-5-yl]-3,6-dihydro-2H-pyridine-1-carboxylate (1) 5-Bromo-2-(4-methanesulfonylphenoxymethyl)-3-methylpyridine The title compound was prepared from (5-bromo-3-methylpyridin-2-yl)methanol (200 mg, 0.990 mmol) following a procedure analogous to that in Example 9 as a pale yellow oil (238 mg, yield 68%).

¹H NMR (CDCl₃, 400 MHz): δ=2.42 (3H, s), 3.02 (3H, s), 5.25 (2H, s), 7.14 (2H, d, J=9 Hz), 7.70 (1H, d, J=2 Hz), 7.85 (2H, d, J=9 Hz), 8.50 (1H, d, J=2 Hz).

(2) tert-Butyl 4-[2-(4-methanesulfonylphenoxymethyl)-3-methylpyridin-5-yl]-3,6-dihydro-2H-pyridine-1-carboxylate The title compound was prepared from 5-bromo-2-(4-methanesulfonylphenoxymethyl)-3-methylpyridine (100 mg, 0.281 mmol) following a procedure analogous to that in Example 3(2) as a pale brown crystal (116 mg, yield 90%).

¹H NMR (CDCl₃, 400 MHz): δ=1.49 (9H, s), 2.43 (3H, s), 2.4-2.6 (2H, m), 3.02 (3H, s), 3.6-3.7 (2H, m), 4.0-4.2 (2H, m), 5.29 (2H, s), 6.11 (1H, brs), 7.16 (2H, d, J=9 Hz), 7.48 (1H, s), 7.85 (2H, d, J=9 Hz), 8.46 (1H, s).

Example 63 tert-Butyl 4-[2-(4-methanesulfonylphenoxymethyl)-3-methylpyridin-5-yl]piperidine-1-carboxylate The title compound was prepared from tert-butyl 4-[2-(4-methanesulfonylphenoxymethyl)-3-methylpyridin-5-yl]-3,6-dihydro-2H-pyridine-1-carboxylate (Example 62) (114 mg, 0.249 mmol) following a procedure analogous to that in Example 3(3) as a white crystal (90 mg, yield 79%).

FAB-MS (m/z): 461 (M+1)

m.p.: 130-132° C.

¹H NMR (CDCl₃, 400 MHz): δ=1.48 (9H, s), 1.5-1.7 (2H, m), 1.8-1.9 (2H, m), 2.41 (3H, s), 2.6-2.9 (3H, m), 3.02 (3H, s), 4.2-4.4 (2H, m), 5.27 (2H, s), 7.16 (2H, d, J=9 Hz), 7.35 (1H, s), 7.85 (2H, d, J=9 Hz), 8.31 (1H, s).

IR (KBr, cm⁻¹): 2972, 2924, 2843, 1693, 1595, 1577, 1502, 1400, 1367, 1313, 1298, 1265, 1232, 1165, 1147, 1115, 1093, 1036, 1001, 970, 910, 866, 829, 802, 775, 621, 542, 526.

Example 64 tert-Butyl 4-[6-(4-methanesulfonylphenoxymethyl)-2-methylpyridin-3-yl]-3,6-dihydro-2H-pyridine-1-carboxylate (1) 3-Bromo-6-(4-methanesulfonylphenoxymethyl)-2-methylpyridine The title compound was prepared from (3-bromo-2-methylpyridin-6-yl)methanol (160 mg, 0.792 mmol) following a procedure analogous to that in Example 9 as a brown crystal (296 mg, yield 99%).

¹H NMR (CDCl₃, 400 MHz): δ=2.69 (3H, s), 3.03 (3H, s), 5.19 (2H, s), 7.10 (2H, d, J=9 Hz), 7.19 (1H, d, J=8 Hz), 7.83 (1H, d, J=8 Hz), 7.87 (2H, d, J=9 Hz).

(2) tert-Butyl 4-[6-(4-methanesulfonylphenoxymethyl)-2-methylpyridin-3-yl]-3,6-dihydro-2H-pyridine-1-carboxylate The title compound was prepared from 3-bromo-6-(4-methanesulfonylphenoxymethyl)-2-methylpyridine (80 mg, 0.225 mmol) following a procedure analogous to that in Example 3(2) as a pale brown amorphous (75 mg, yield 73%).

FAB-MS (m/z): 459 (M+1)

¹H NMR (CDCl₃, 400 MHz): δ=1.51 (9H, s), 2.3-2.4 (2H, m), 2.53 (3H, s), 3.03 (3H, s), 3.6-3.7 (2H, m), 4.0-4.1 (2H, m), 5.23 (2H, s), 5.63 (1H, brs), 7.12 (2H, d, J=9 Hz), 7.27 (1H, d, J=8 Hz), 7.41 (1H, d, J=8 Hz), 7.87 (2H, d, J=9 Hz).

Example 65 tert-Butyl 4-[6-(4-methanesulfonylphenoxymethyl)-2-methylpyridin-3-yl]piperidine-1-carboxylate The title compound was prepared from tert-butyl 4-[6-(4-methanesulfonylphenoxymethyl)-2-methylpyridin-3-yl]-3,6-dihydro-2H-pyridine-1-carboxylate (Example 64) (45 mg, 0.0981 mmol) following a procedure analogous to that in Example 7 as a white crystal (10.3 mg, yield 23%).

FAB-MS (m/z): 461 (M+1)

¹H NMR (CDCl₃, 400 MHz): δ=1.49 (9H, s), 1.5-1.7 (2H, m), 1.7-1.9 (2H, m), 2.63 (3H, s), 2.7-2.9 (3H, m), 3.03 (3H, s), 4.2-4.3 (2H, m), 5.23 (2H, s), 7.12 (2H, d, J=9 Hz), 7.31 (1H, s), 7.52 (1H, s), 7.87 (2H, d, J=9 Hz).

Example 66 tert-Butyl 4-[2-(4-methanesulfonylphenoxymethyl)-3-methoxypyridin-5-yl]-3,6-dihydro-2H-pyridine-1-carboxylate (1) 5-Bromo-2-(4-methanesulfonylphenoxymethyl)-3-methoxypyridine The title compound was prepared from (5-bromo-3-methoxypyridin-2-yl)methanol (112 mg, 0.514 mmol) following a procedure analogous to that in Example 9 as a white amorphous (141 mg, yield 74%).
$^1$H NMR (CDCl$_3$, 400 MHz): δ=3.02 (3H, s), 3.91 (3H, s), 5.25 (2H, s), 7.14 (2H, d, J=9 Hz), 7.40 (1H, d, J=2 Hz), 7.85 (2H, d, J=9 Hz), 8.29 (1H, d, J=2 Hz).

(2) tert-Butyl 4-[2-(4-methanesulfonylphenoxymethyl)-3-methoxypyridin-5-yl]-3,6-dihydro-2H-pyridine-1-carboxylate The title compound was prepared from 5-bromo-2-(4-methanesulfonylphenoxymethyl)-3-methoxypyridine (141 mg, 0.379 mmol) following a procedure analogous to that in Example 3(2) as a pale yellow amorphous (159 mg, yield 88%).
FAB-MS (m/z): 475 (M+1)
$^1$H NMR (CDCl$_3$, 400 MHz): δ=1.49 (9H, s), 2.5-2.6 (2H, m), 3.02 (3H, s), 3.6-3.7 (2H, m), 3.91 (3H, s), 4.0-4.2 (2H, m), 5.29 (2H, s), 6.12 (1H, brs), 7.17 (2H, d, J=8 Hz), 7.18 (1H, s), 7.84 (2H, d, J=8 Hz), 8.25 (1H, s).

Example 67 tert-Butyl 4-[2-(4-methanesulfonylphenoxymethyl)-3-methoxypyridin-5-yl]piperidine-1-carboxylate The title compound was prepared from tert-butyl 4-[2-(4-methanesulfonylphenoxymethyl)-3-methoxypyridin-5-yl]-3,6-dihydro-2H-pyridine-1-carboxylate (Example 66) (125 mg, 0.263 mmol) following a procedure analogous to that in Example 7 as a white crystal (70 mg, yield 56%).
FAB-MS (m/z): 477 (M+1)
m.p.: 153-154° C.
$^1$H NMR (CDCl$_3$, 400 MHz): δ=1.49 (9H, s), 1.5-1.7 (2H, m), 1.8-1.9 (2H, m), 2.7-2.9 (3H, m), 3.02 (3H, s), 3.89 (3H, s), 4.2-4.4 (2H, m), 5.27 (2H, s), 7.06 (1H, s), 7.17 (2H, d, J=9 Hz), 7.85 (2H, d, J=9 Hz), 8.12 (1H, s).
IR (KBr, cm$^{-1}$): 2999, 2976, 2933, 2860, 1695, 1591, 1498, 1456, 1415, 1367, 1296, 1246, 1163, 1140, 1117, 1086, 1020, 989, 955, 877, 839, 769, 571, 542, 523.

Example 68 tert-Butyl 4-[3-benzyloxy-2-(4-methanesulfonylphenoxymethyl)pyridin-5-yl]-3,6-dihydro-2H-pyridine-1-carboxylate (1) 3-Benzyloxy-2,5-dibromopyridine To a solution of 2,5-dibromopyridin-3-ol (200 mg, 0.791 mmol) in dry N,N-dimethylformamide (8 mL) was added potassium carbonate (164 mg, 1.19 mmol) and benzyl bromide (0.11 mL, 0.949 mmol). The mixture was stirred at room temperature for 2 hours, diluted with water (10 mL) and extracted with ethyl acetate. The organic layer was washed with brine, dried over anhydrous sodium sulfate and concentrated under reduced pressure. The residue was purified by silica gel column chromatography (hexane/ethyl acetate=19/1→3/2) to give the title compound as a white crystal (211 mg, yield 78%).
$^1$H NMR (CDCl$_3$, 400 MHz): δ=5.17 (2H, s), 7.30 (1H, d, J=2 Hz), 7.3-7.5 (5H, m), 8.07 (1H, d, J=2 Hz).

(2) (3-Benzyloxy-5-bromopyridin-2-yl)methanol

A solution of 3-benzyloxy-2,5-dibromopyridine (210 mg, 0.612 mmol) in toluene was cooled to −78° C. under N$_2$ and n-butyllithium (1.60M, 0.46 mL, 0.735 mmol) was added dropwise. The mixture was stirred at −78° C. for 2.5 hours followed by the addition of dry N,N-dimethylformamide (0.095 mL, 1.22 mmol). After gradually warming to room temperature, methanol (5 mL) and sodium borohydride (23 mg, 0.612 mmol) was added to the mixture. The resulting mixture was stirred for 30 minutes, to which was added saturated aqueous ammonium chloride solution and extracted with ethyl acetate. The organic layer was washed with brine, dried over anhydrous sodium sulfate and concentrated under reduced pressure. The residue was purified by silica gel column chromatography (hexane/ethyl acetate=4/1) to give the title compound as a yellow crystal (111 mg, yield 62%).
$^1$H NMR (CDCl$_3$, 400 MHz): δ=3.91 (1H, brs), 4.74 (2H, s), 5.10 (2H, s), 7.34 (1H, s), 7.3-7.5 (5H, m), 8.24 (1H, s).

(3) 3-Benzyloxy-5-bromo-2-(4-methanesulfonylphenoxy-methyl)pyridine

The title compound was prepared from (3-benzyloxy-5-bromopyridin-2-yl)methanol (111 mg, 0.377 mmol) following a procedure analogous to that in Example 9 as a yellow amorphous (185 mg, yield 99%).
$^1$H NMR (CDCl$_3$, 400 MHz): δ=3.02 (3H, s), 5.14 (2H, s), 5.29 (2H, s), 7.12 (2H, d, J=9 Hz), 7.3-7.5 (5H, m), 7.45 (1H, d, J=2 Hz), 7.83 (2H, d, J=9 Hz), 8.30 (1H, d, J=2 Hz).

(4) tert-Butyl 4-[3-benzyloxy-2-(4-methanesulfonylphenoxymethyl)pyridin-5-yl]-3,6-dihydro-2H-pyridine-1-carboxylate The title compound was prepared from 3-benzyloxy-5-bromo-2-(4-methanesulfonylphenoxymethyl)pyridine (185 mg, 0.413 mmol) following a procedure analogous to that in Example 3(2) as a brown oil (168 mg, yield 74%).
$^1$H NMR (CDCl$_3$, 400 MHz): δ=1.62 (9H, s), 2.4-2.5 (2H, m), 3.02 (3H, s), 3.6-3.7 (2H, m), 4.0-4.1 (2H, m), 5.17 (2H, s), 5.34 (2H, s), 6.08 (1H, brs), 7.15 (2H, d, J=9 Hz), 7.23 (1H, s), 7.3-7.5 (5H, m), 7.82 (2H, d, J=9 Hz), 8.26 (1H, s).

Example 69 tert-Butyl 4-[3-hydroxy-2-(4-methanesulfonylphenoxymethyl)pyridin-5-yl]piperidine-1-carboxylate The title compound was prepared from tert-butyl 4-[3-benzyloxy-2-(4-methanesulfonylphenoxymethyl)pyridin-5-yl]-3,6-dihydro-2H-pyridine-1-carboxylate (Example 68) (60 mg, 0.109 mmol) following a procedure analogous to that in Example 3(3) as a white crystal (17 mg, yield 34%).
FAB-MS (m/z): 463 (M+1)
$^1$H NMR (CDCl$_3$, 400 MHz): δ=1.48 (9H, s), 1.4-1.7 (2H, m), 1.7-1.9 (2H, m), 2.6-2.9 (3H, m), 3.02 (3H, s), 4.2-4.3

(2H, m), 5.42 (2H, s), 6.58 (1H, brs), 7.06 (1H, d, J=1 Hz), 7.18 (2H, d, J=9 Hz), 7.88 (2H, d, J=9 Hz), 8.07 (1H, d, J=1 Hz).

Example 70 tert-Butyl 4-[3-chloro-2-(4-methanesulfonylphenoxymethyl)pyridin-5-yl]-3,6-dihydro-2H-pyridine-1-carboxylate

(1) (5-Bromo-3-chloropyridin-2-yl)methanol

The title compound was prepared from 3-chloro-2,5-dibromopyridine (100 mg, 0.369 mmol) following a procedure analogous to that in Example 68(2) as a pale yellow crystal (48 mg, yield 59%).

$^1$H NMR (CDCl$_3$, 400 MHz): δ=3.93 (1H, brs), 4.75 (2H, s), 7.86 (1H, d, J=2 Hz), 8.56 (1H, brs).

(2) 5-Bromo-3-chloro-2-(4-methanesulfonylphenoxymethyl)-pyridine

The title compound was prepared from (5-bromo-3-chloropyridin-2-yl)methanol (48 mg, 0.216 mmol) following a procedure analogous to that in Example 9 as a yellow crystal (64 mg, yield 79%).

$^1$H NMR (CDCl$_3$, 400 MHz): δ=3.03 (3H, s), 5.33 (2H, s), 7.14 (2H, d, J=9 Hz), 7.87 (2H, d, J=9 Hz), 7.94 (1H, d, J=2 Hz), 8.59 (1H, d, J=2 Hz).

(3) tert-Butyl 4-[3-chloro-2-(4-methanesulfonylphenoxy-methyl)pyridin-5-yl]-3,6-dihydro-2H-pyridine-1-carboxylate The title compound was prepared from 5-bromo-3-chloro-2-(4-methanesulfonylphenoxymethyl)pyridine (64 mg, 0.170 mmol) following a procedure analogous to that in Example 3 (2) as a white amorphous (71 mg, yield 87%).

$^1$H NMR (CDCl$_3$, 400 MHz): δ=1.49 (9H, s), 2.4-2.6 (2H, m), 3.03 (3H, s), 3.6-3.7 (2H, m), 3.9-4.1 (2H, m), 5.36 (2H, s), 6.18 (1H, brs), 7.16 (2H, d, J=9 Hz), 7.70 (1H, d, J=2 Hz), 7.87 (2H, d, J=9 Hz), 8.55 (1H, d, J=2 Hz).

Example 71 tert-Butyl 4-[3-chloro-2-(4-methanesulfonylphenoxymethyl)pyridin-5-yl]piperidine-1-carboxylate To a solution of tert-butyl 4-[3-chloro-2-(4-methanesulfonylphenoxymethyl)pyridin-5-yl]-3,6-dihydro-2H-pyridine-1-carboxylate (Example 70) (50 mg, 0.104 mmol) in ethyl acetate (1 mL) was added platinum oxide (5 mg). The mixture was hydrogenated at room temperature for 4 hours and filtered through Celite pad. The filtrate was concentrated under reduced pressure. The residue was purified by silica gel column chromatography (hexane/ethyl acetate=1/1) to give the title compound as a white amorphous (13 mg, yield 26%).

FAB-MS (m/z): 481 (M+1)

$^1$H NMR (CDCl$_3$, 400 MHz): δ=1.48 (9H, s), 1.5-1.7 (2H, m), 1.8-1.9 (2H, m), 2.7-2.9 (3H, m), 3.03 (3H, s), 4.2-4.4 (2H, m), 5.35 (2H, s), 7.16 (2H, d, J=9 Hz), 7.58 (1H, s), 7.87 (2H, d, J=9 Hz), 8.40 (1H, s).

Example 72 tert-Butyl 4-[2-(4-methanesulfonylphenoxymethyl)-3-trifluoromethylpyridin-5-yl]-3,6-dihydro-2H-pyridine-1-carboxylate

(1) (5-Bromo-3-trifluoromethylpyridin-2-yl)methanol

The title compound was prepared from 2,5-dibromo-3-trifluoromethylpyridine (120 mg, 0.394 mmol) following a procedure analogous to that in Example 68(2) as a yellow crystal (39 mg, yield 39%).

$^1$H NMR (CDCl$_3$, 400 MHz): δ=4.16 (1H, t, J=5 Hz), 4.86 (2H, d, J=5 Hz), 8.10 (1H, d, J=2 Hz), 8.82 (1H, d, J=2 Hz).

(2) 5-Bromo-2-(methanesulfonylphenoxymethyl)-3-trifluoromethylpyridine

The title compound was prepared from (5-bromo-3-trifluoromethylpyridin-2-yl)methanol (39 mg, 0.152 mmol) following a procedure analogous to that in Example 9 as a yellow crystal (58 mg, yield 93%).

$^1$H NMR (CDCl$_3$, 400 MHz): δ=3.03 (3H, s), 5.37 (2H, s), 7.11 (2H, d, J=9 Hz), 7.87 (2H, d, J=9 Hz), 8.18 (1H, d, J=2 Hz), 8.86 (1H, d, J=2 Hz).

(3) tert-Butyl 4-[2-(4-methanesulfonylphenoxymethyl)-3-trifluoromethylpyridin-5-yl]-3,6-dihydro-2H-pyridine-1-carboxylate The title compound was prepared from 5-bromo-2-(methanesulfonylphenoxymethyl)-3-trifluoromethylpyridine (58 mg, 0.141 mmol) following a procedure analogous to that in Example 3(2) as a pale yellow oil (7 mg, yield 10%).

$^1$H NMR (CDCl$_3$, 400 MHz): δ=1.50 (9H, s), 2.5-2.6 (2H, m), 3.03 (3H, s), 3.6-3.7 (2H, m), 4.1-4.2 (2H, m), 5.40 (2H, s), 6.24 (1H, brs), 7.12 (2H, d, J=9 Hz), 7.87 (2H, d, J=9 Hz), 7.97 (1H, d, J=2 Hz), 8.80 (1H, d, J=2 Hz).

Example 73 tert-Butyl 4-[2-(4-methanesulfonylphenoxymethyl)-3-trifluoromethylpyridin-5-yl]piperidine-1-carboxylate The title compound was prepared from tert-butyl 4-[2-(4-methanesulfonylphenoxymethyl)-3-trifluoromethylpyridin-5-yl]-3,6-dihydro-2H-pyridine-1-carboxylate (Example 72) (7 mg, 0.0137 mmol) following a procedure analogous to that in Example 71 as a white amorphous (7 mg, yield 99%).

FAB-MS (m/z): 515 (M+1)

$^1$H NMR (CDCl$_3$, 400 MHz): δ=1.49 (9H, s), 1.6-1.7 (2H, m), 1.8-1.9 (2H, m), 2.7-2.8 (3H, m), 3.03 (3H, s), 4.2-4.4 (2H, m), 5.38 (2H, s), 7.12 (2H, d, J=9 Hz), 7.84 (1H, d, J=2 Hz), 7.87 (2H, d, J=9 Hz), 8.67 (1H, d, J=2 Hz).

Example 74 tert-Butyl 4-[3-fluoro-2-(4-methanesulfonylphenoxymethyl)pyridin-5-yl]-3,6-dihydro-2H-pyridine-1-carboxylate

(1) (5-Bromo-3-fluoropyridin-2-yl)methanol

The title compound was prepared from 3-fluoro-2,5-dibromopyridine (200 mg, 0.785 mmol) following a procedure analogous to that in Example 68(2) as a pale yellow crystal (109 mg, yield 67%).

¹H NMR (CDCl₃, 400 MHz): δ=3.54 (1H, t, J=5 Hz), 4.79 (2H, dd, J=1 Hz, 5 Hz), 7.60 (1H, dd, J=1 Hz, 8 Hz), 8.49 (1H, s).

(2) 5-Bromo-3-fluoro-2-(4-methanesulfonylphenoxymethyl)-pyridine

The title compound was prepared from (5-bromo-3-fluoropyridin-2-yl)methanol (109 mg, 0.529 mmol) following a procedure analogous to that in Example 9 as a white crystal (137 mg, yield 72%).
¹H NMR (CDCl₃, 400 MHz): δ=3.03 (3H, s), 5.29 (2H, d, J=2 Hz), 7.15 (2H, d, J=9 Hz), 7.68 (1H, dd, J=2 Hz, 9 Hz), 7.87 (2H, d, J=9 Hz), 8.54 (1H, d, J=2 Hz).

(3) tert-Butyl 4-[3-fluoro-2-(4-methanesulfonylphenoxy-methyl)pyridin-5-yl]-3,6-dihydro-2H-pyridine-1-carboxylate The title compound was prepared from 5-bromo-3-fluoro-2-(4-methanesulfonylphenoxymethyl)pyridine (70 mg, 0.194 mmol) following a procedure analogous to that in Example 3(2) as a pale yellow amorphous (93 mg, yield>99%).
¹H NMR (CDCl₃, 400 MHz): δ=1.49 (9H, s), 2.4-2.6 (2H, m), 3.02 (3H, s), 3.6-3.7 (2H, m), 4.1-4.2 (2H, m), 5.32 (2H, d, J=2 Hz), 6.19 (1H, bra), 7.17 (2H, d, J=9 Hz), 7.41 (1H, dd, J=2 Hz, 11 Hz), 7.87 (2H, d, J=9 Hz), 8.50 (1H, brs).

Example 75 tert-Butyl 4-[3-fluoro-2-(4-methanesulfonylphenoxy-methyl)pyridin-5-yl]piperidine-1-carboxylate The title compound was prepared from tert-butyl 4-[3-fluoro-2-(4-methanesulfonylphenoxymethyl)pyridin-5-yl]-3,6-dihydro-2H-pyridine-1-carboxylate (Example 74) (50 mg, 0.108 mmol) following a procedure analogous to that in Example 7 as a white crystal (13 mg, yield 26%).
FAB-MS (m/z): 465 (M+1)
¹H NMR (CDCl₃, 400 MHz): δ=1.48 (9H, s), 1.5-1.7 (2H, m), 1.8-1.9 (2H, m), 2.7-2.9 (3H, m), 3.02 (3H, s), 4.2-4.3 (2H, m), 5.30 (2H, d, J=2 Hz), 7.17 (2H, d, J=9 Hz), 7.30 (1H, dd, J=2 Hz, 9 Hz), 7.87 (2H, d, J=9 Hz), 8.34 (1H, brs).

Example 76 tert-Butyl 4-[4-chloro-2-(4-methanesulfonylphenoxymethyl)pyridin-5-yl]-3,6-dihydro-2H-pyridine-1-carboxylate

(1) 5-Bromo-4-chloro-2-(4-methanesulfonylphenoxymethyl)-pyridine

The title compound was prepared from (5-bromo-4-chloropyridin-2-yl)methanol (100 mg, 0.450 mmol) following a procedure analogous to that in Example 9 as a white crystal (127 mg, yield 75%).
¹H NMR (CDCl₃, 400 MHz): δ=3.04 (3H, s), 5.21 (2H, s), 7.11 (2H, d, J=9 Hz), 7.62 (1H, s), 7.90 (2H, d, J=9 Hz), 8.73 (1H, s).

(2) tert-Butyl 4-[4-chloro-2-(4-methanesulfonylphenoxy-methyl)pyridin-5-yl]-3,6-dihydro-2H-pyridine-1-carboxylate The title compound was prepared from 5-bromo-4-chloro-2-(4-methanesulfonylphenoxymethyl)pyridine (127 mg, 0.337 mmol) following a procedure analogous to that in Example 3(2) as a white crystal (128 mg, yield 79%).
FAB-MS (m/z): 479 (M+1)
m.p.: 148-150° C.
¹H NMR (CDCl₃, 400 MHz): δ=1.51 (9H, s), 2.4-2.5 (2H, m), 3.04 (3H, s), 3.6-3.7 (2H, m), 4.0-4.2 (2H, m), 5.24 (2H, s), 5.79 (1H, brs), 7.13 (2H, d, J=9 Hz), 7.51 (1H, s), 7.89 (2H, d, J=9 Hz), 8.39 (1H, s).

Example 77 tert-Butyl 4-[2-[(4-methanesulfonylphenylamino)methyl]pyridin-5-yl]piperidine-1-carboxylate

(1) tert-Butyl 4-[(2-azidomethyl)pyridin-5-yl]piperidine-1-carboxylate

To an ice-cooled solution of tert-butyl 4-[(2-hydroxymethyl)pyridin-5-yl]piperidine-1-carboxylate (Example 1 (2)) (116 mg, 0.397 mmol) in dry tetrahydrofuran (4.0 mL) was added sequentially diphenylphosphoryl azide (94 μL, 0.437 mmol) and 1,8-diazabicyclo[5,4,0]undec-7-ene (59 μL, 0.397 mmol) under N₂. The mixture was stirred at 0° C. for 1 hour and then stirred at room temperature for an additional 24 hours. To the mixture was added saturated aqueous citric acid solution and extracted with ethyl acetate. The organic layer was washed sequentially with water and brine, dried over anhydrous sodium sulfate and concentrated under reduced pressure. The residue was purified by silica gel column chromatography to give the title compound (55 mg, yield 44%).
¹H NMR (CDCl₃, 400 MHz): δ=1.49 (9H, s), 1.5-1.7 (2H, m), 1.8-1.9 (2H, m), 2.6-2.8 (1H, m), 2.7-2.9 (2H, m), 4.2-4.4 (2H, m), 4.46 (2H, s), 7.29 (1H, d, J=8 Hz), 7.55 (1H, dd, J=2 Hz, 8 Hz), 8.47 (1H, d, J=2 Hz).

(2) tert-Butyl 4-[2-[(4-methanesulfonylphenylamino)-methyl]pyridin-5-yl]piperidine-1-carboxylate To a solution of tert-butyl 4-[(2-azidomethyl)pyridin-5-yl]piperidine-1-carboxylate (55 mg, 0.173 mmol) in methanol (5.0 mL) was added 10% palladium-carbon (6.0 mg). The mixture was hydrogenated at room temperature for 24 hours and filtered through Celite pad. The filtrate was concentrated under reduced pressure to give tert-butyl 4-[(2-aminomethyl)pyridin-5-yl]-piperidine-1-carboxylate.
solution of tert-butyl 4-[(2-aminomethyl)pyridin-5-yl]piperidine-1-carboxylate, 1-bromo-4-methanesulfonyl-benzene (40 mg, 0.170 mmol), potassium hydroxide (19 mg, 0.339 mmol), tris(dibenzylideneacetone)dipalladium(0) (3 mg, 3.28 μmol) and 5-(di-tert-butylphosphino)-1',3',5'-triphenyl-1'H-[1,4']bipyrazole (5 mg, 9.87 μmol) in 2-methyl-2-butanol (8.0 mL)-water (4.0 mL) was stirred at 100° C. overnight, allowed to cool to room temperature, diluted with water and extracted with ethyl acetate. The organic layer was washed with brine, dried over anhydrous sodium sulfate and concentrated under reduced pressure. The residue was purified by silica gel column chromatography (chloroform/ethyl acetate=1/3) to give the title compound as a pale yellow oil (3.4 mg, yield 4%).
FAB-MS (m/z): 446 (M+1)
¹H NMR (CDCl₃, 400 MHz): δ=1.48 (9H, s), 1.5-1.9 (4H, m), 2.6-2.8 (1H, m), 2.7-2.9 (2H, m), 3.00 (3H, s), 4.2-4.4 (2H, m), 4.49 (2H, s), 5.61 (1H, brs), 6.71 (2H, d, J=9 Hz), 7.27 (1H, d, J=8 Hz), 7.54 (1H, dd, J=2 Hz, 8 Hz), 7.71 (2H, d, J=9 Hz), 8.46 (1H, d, J=2 Hz).

Example 78 tert-Butyl (E)-4-[2-[2-(4-methanesulfonylphenyl)vinyl]pyridin-5-yl]piperidine-1-carboxylate A solution of tert-butyl 4-[(2-hydroxymethyl)pyridin-5-yl]piperidine-1-carboxylate (Example 1(2)) (200 mg, 0.684 mmol), tetrabromomethane (227 mg, 0.684 mmol) and triphenylphosphine (216 mg, 0.824 mmol) in dry dichloromethane (5.0 mL) was stirred at 0° C. for 1 hour under $N_2$. The mixture was diluted with water and extracted with ethyl acetate. The organic layer was washed sequentially with water and brine, dried over anhydrous sodium sulfate and concentrated under reduced pressure.

To the residue was added triethyl phosphite (273 μL, 2.12 mmol). The resulting mixture was stirred at 150° C. for 1 hour and concentrated in vacuo. An ice-cooled solution of the residue in dry tetrahydrofuran (3.0 mL) was added sodium hydride (60% dispersion in mineral oil, 33 mg, 0.825 mmol) under $N_2$. The mixture was stirred at room temperature for 1 hour followed by the addition of a solution of 4-methanesulfonylbenzaldehyde (84 mg, 0.456 mmol) in dry tetrahydrofuran (2.0 mL). The resulting mixture was stirred at room temperature for 2 hours, diluted with water and extracted with ethyl acetate. The organic layer was washed with brine, dried over anhydrous sodium sulfate and concentrated under reduced pressure. The residue was purified by silica gel column chromatography to give the title compound as a pale brown crystal (27 mg, yield 9%).

FAB-MS (m/z): 443 (M+1)
$^1$H NMR (CDCl$_3$, 400 MHz): δ=1.49 (9H, s), 1.5-1.7 (2H, m), 1.8-1.9 (2H, m), 2.6-2.8 (1H, m), 2.7-2.9 (2H, m), 3.07 (3H, s), 4.1-4.4 (2H, m), 7.28 (1H, d, J=15 Hz), 7.37 (1H, d, J=8 Hz), 7.54 (1H, dd, J=2 Hz, 8 Hz), 7.65 (1H, d, J=15 Hz), 7.73 (2H, d, J=8 Hz), 7.93 (2H, d, J=8 Hz), 8.51 (1H, d, J=2 Hz).

Example 79 tert-Butyl 4-[2-[2-(4-methanesulfonylphenyl)ethyl]pyridin-5-yl]piperidine-1-carboxylate The title compound was prepared from tert-butyl (E)-4-[2-[2-(4-methanesulfonylphenyl)vinyl]pyridin-5-yl]piperidine-1-carboxylate (Example 78) (14 mg, 31.6 μmol) following a procedure analogous to that in Example 3 (3) as a white crystal (11 mg, yield 78%).

FAB-MS (m/z): 445 (M+1)
$^1$H NMR (CDCl$_3$, 400 MHz): δ=1.49 (9H, s), 1.5-1.7 (2H, m), 1.7-1.9 (2H, m), 2.6-2.7 (1H, m), 2.7-2.9 (2H, m), 3.04 (3H, s), 3.0-3.1 (2H, m), 3.1-3.2 (2H, m), 4.1-4.4 (2H, m), 7.02 (1H, d, J=8 Hz), 7.38 (2H, d, J=8 Hz), 7.41 (1H, dd, J=2 Hz, 8 Hz), 7.83 (2H, d, J=8 Hz), 8.42 (1H, brs).

Example 80 tert-Butyl 4-[2-(2-chloro-4-methanesulfonylphenoxymethyl)-3-methylpyridin-5-yl]piperidine-1-carboxylate (1) 5-Bromo-2-(tert-butyldimethylsilanyloxymethyl)-3-methylpyridine To a solution of 5-bromo-2-hydroxymethyl-3-methylpyridine (1 g, 5 mmol) in N,N-dimethylformamide (50 mL) was added triethylamine (1.56 mL, 15 mmol) and tert-butylchlorodimethylsilane (1.13 g, 7.5 mmol). The mixture was stirred at room temperature for 4 hours, diluted with water (50 mL) and extracted with ethyl acetate. The organic layer was washed with brine, dried over anhydrous sodium sulfate and concentrated under reduced pressure. The residue was purified by silica gel column chromatography (hexane/ethyl acetate=4/1) to give the title compound as a colorless oil (1.51 g, yield 100%).

$^1$H NMR (CDCl$_3$, 400 MHz): δ=0.07 (6H, s), 0.89 (9H, s), 2.40 (3H, s), 4.77 (2H, s), 7.61 (1H, brs), 8.41 (1H, d, J=2 Hz).

(2) tert-Butyl 4-[2-(tert-butyldimethylsilanyloxymethyl)-3-methylpyridin-5-yl]-3,6-dihydro-2H-pyridine-1-carboxylate The title compound was prepared from 5-bromo-2-(tert-butyldimethylsilanyloxymethyl)-3-methylpyridine (907 mg, 3 mmol) following a procedure analogous to that in Example 3 (2) as a yellow oil (1.12 g, yield 97%).

$^1$H NMR (CDCl$_3$, 400 MHz): δ=0.07 (6H, s), 0.89 (9H, s), 1.49 (9H, s), 2.41 (3H, s), 2.4-2.6 (2H, m), 3.6-3.7 (2H, m), 4.0-4.1 (2H, m), 4.81 (2H, s), (3) tert-Butyl 4-[(2-hydroxymethyl)-3-methylpyridin-5-yl]piperidine-1-carboxylate To a solution of tert-butyl 4-[2-(tert-butyldimethylsilanyloxymethyl)-3-methylpyridin-5-yl]-3,6-dihydro-2H-pyridine-1-carboxylate (1.18 g, 2.91 mmol) in dry tetrahydrofuran (29 mL) was added tetrabutylammonium fluoride (1.0M in tetrahydrofuran, 4.37 mL, 4.37 mmol). The mixture was stirred at room temperature for 5 hours and diluted with ethyl acetate. The organic layer was washed with brine, dried over anhydrous sodium sulfate and concentrated under reduced pressure.

To a solution of the residue in methanol (29 mL) was added 10% palladium-carbon (617 mg). The mixture was hydrogenated at room temperature for 1 hour and filtered through Celite pad. The filtrate was concentrated under reduced pressure. The residue was purified by silica gel column chromatography (hexane/ethyl acetate=1/2) to give the title compound as a white crystal (605 mg, yield 68%).

$^1$H NMR (CDCl$_3$, 400 MHz): δ=1.49 (9H, s), 1.5-1.7 (2H, m), 1.7-1.9 (2H, m), 2.20 (3H, s), 2.6-2.9 (3H, m), 4.2-4.4 (2H, m), 4.6-4.8 (1H, m), 4.66 (2H, s), 7.26 (1H, s), 8.26 (1H, s).

(4) tert-Butyl 4-[2-(2-chloro-4-methanesulfonylphenoxymethyl)-3-methylpyridin-5-yl]piperidine-1-carboxylate The title compound was prepared from tert-butyl 4-[2-(4-methanesulfonyloxymethyl)-3-methylpyridin-5-yl]piperidine-1-carboxylate (30 mg, 0.098 mmol) and 2-chloro-4-methanesulfonylphenol (26 mg, 0.127 mmol) following a procedure analogous to that in Example 9 as a white crystal (17 mg, yield 34%).

FAB-MS (m/z): 495 (M+1)
m.p.: 143-145° C.
$^1$H NMR (CDCl$_3$, 400 MHz): δ=1.48 (9H, s), 1.5-1.7 (2H, m), 1.7-1.9 (2H, m), 2.46 (3H, s), 2.6-2.9 (3H, m), 3.03 (3H, s), 4.2-4.4 (2H, m), 5.38 (2H, s), 7.3-7.4 (2H, m), 7.77 (1H, dd, J=2 Hz, 9 Hz), 7.92 (1H, d, J=2 Hz), 8.29 (1H, d, J=2 Hz).
IR (KBr, cm$^{-1}$): 3022, 2981, 2929, 2852, 1685, 1585, 1491, 1429, 1392, 1367, 1311, 1279, 1236, 1149, 1122, 1101, 1059, 1030, 999, 962, 901, 864, 825, 762, 725, 584, 525, 492.

Example 81 tert-Butyl 4-[2-(2-bromo-4-methanesulfonylphenoxymethyl)-3-methylpyridin-5-yl]piperidine-1-carboxylate The title compound was prepared from tert-butyl 4-[2-(4-methanesulfonyloxymethyl)-3-methylpyridin-5-yl]piperidine-1-carboxylate (Example 80(3)) (30 mg, 0.098 mmol) and 2-bromo-4-methanesulfonylphenol (32 mg, 0.127 mmol) following a procedure analogous to that in Example 9 as a colorless oil (15 mg, yield 27%).

FAB-MS (m/z): 539 (M+1), 541 (M+3)

$^1$H NMR (CDCl$_3$, 400 MHz): δ=1.48 (9H, s), 1.5-1.7 (2H, m), 1.7-1.9 (2H, m), 2.47 (3H, s), 2.6-2.9 (3H, m), 3.03 (3H, s), 4.2-4.4 (2H, m), 5.38 (2H, s), 7.3-7.4 (2H, m), 7.80 (1H, dd, J=2 Hz, 9 Hz), 7.92 (1H, d, J=2 Hz), 8.29 (1H, d, J=2 Hz).

Example 82 tert-Butyl 4-[2-(4-methanesulfonyl-2-methylphenoxymethyl)-3-methylpyridin-5-yl]piperidine-1-carboxylate The title compound was prepared from tert-butyl 4-[(2-hydroxymethyl)-3-methylpyridin-5-yl]piperidine-1-carboxylate (Example 80 (3)) (69 mg, 0.225 mmol) and 4-methanesulfonyl-2-methylphenol (48 mg, 0.260 mmol) following a procedure analogous to that in Example 1(3) and (4) as a pale yellow amorphous (37 mg, yield 30%).

FAB-MS (m/z): 474 (M+1)

$^1$H NMR (CDCl$_3$, 400 MHz): δ=1.48 (9H, s), 1.5-1.7 (2H, m), 1.7-1.9 (2H, m), 2.26 (3H, s), 2.42 (3H, s), 2.6-2.9 (3H, m), 3.01 (3H, s), 4.1-4.4 (2H, m), 5.29 (2H, s), 7.19 (1H, d, J=9 Hz), 7.35 (1H, d, J=2 Hz), 7.68 (1H, d, J=2 Hz), 7.73 (1H, dd, J=2 Hz, 9 Hz), 8.30 (1H, d, J=2 Hz).

Example 83 tert-Butyl 4-[2-[2-fluoro-4-(tetrazol-1-yl)phenoxymethyl]-3-methylpyridin-5-yl]piperidine-1-carboxylate The title compound was prepared from tert-butyl 4-[(2-hydroxymethyl)-3-methylpyridin-5-yl]piperidine-1-carboxylate (Example 80(3)) (80 mg, 0.26 mmol) and 1-(3-fluoro-4-hydroxyphenyl)tetrazole (50 mg, 0.27 mmol) following a procedure analogous to that in Example 9 as a pink crystal (25 mg, yield 20%).

FAB-MS (m/z): 469 (M+1)

$^1$H NMR (CDCl$_3$, 400 MHz): δ=1.48 (9H, s), 1.5-1.7 (2H, m), 1.7-1.9 (2H, m), 2.47 (3H, s), 2.6-2.8 (1H, m), 2.7-2.9 (2H, m), 4.2-4.4 (2H, m), 5.35 (2H, s), 7.3-7.5 (3H, m), 7.48 (1H, dd, J=2 Hz, 8 Hz), 8.30 (1H, d, J=2 Hz), 8.88 (1H, s).

Example 84 tert-Butyl 4-[2-(4-methanesulfonylphenylthiomethyl)-pyridin-5-yl]piperidine-1-carboxylate A suspension of tert-butyl 4-[2-(methanesulfonyloxymethyl)pyridin-5-yl]piperidine-1-carboxylate (Example 1(3)) (61 mg, 0.165 mmol), methanesulfonylbenzenethiol (31 mg, 0.165 mmol) and cesium carbonate (81 mg, 0.247 mmol) in acetone (1.6 mL) was stirred at room temperature for 20 hours. To the mixture was added saturated aqueous ammonium chloride solution and extracted with ethyl acetate. The organic layer was washed with brine, dried over anhydrous sodium sulfate and concentrated under reduced pressure. The residue was purified by silica gel column chromatography (hexane/ethyl acetate=1/2) and recrystallization (hexane-ethyl acetate) to give the title compound as a white crystal (52 mg, yield 68%).

FAB-MS (m/z): 463 (M+1)

$^1$H NMR (CDCl$_3$, 400 MHz): δ=1.48 (9H, s), 1.5-1.7 (2H, m), 1.7-1.9 (2H, m), 2.6-2.9 (3H, m), 3.02 (3H, s), 4.2-4.3 (2H, m), 4.34 (2H, s), 7.36 (1H, d, J=8 Hz), 7.4-7.5 (3H, m), 7.78 (2H, d, J=8 Hz), 8.42 (1H, d, J=2 Hz).

IR (KBr, cm$^{-1}$): 3003, 2976, 2922, 2850, 1687, 1577, 1479, 1423, 1394, 1365, 1304, 1275, 1234, 1171, 1151, 1082, 1022, 970, 887, 862, 820, 779, 735, 573, 532.

Example 85 tert-Butyl 4-[2-(4-methanesulfonyl-3-methylphenoxymethyl)pyridin-5-yl]piperidine-1-carboxylate The title compound was prepared from tert-butyl 4-[(2-hydroxymethyl)pyridin-5-yl]piperidine-1-carboxylate (Example 1(2)) (64 mg, 0.219 mmol) and 4-methanesulfonyl-3-methylphenol (41 mg, 0.219 mmol) following a procedure analogous to that in Example 1(3) and (4) as a pale yellow amorphous (35 mg, yield 35%).

FAB-MS (m/z): 461 (M+1)

$^1$H NMR (CDCl$_3$, 400 MHz): δ=1.49 (9H, s), 1.5-1.7 (2H, m), 1.8-1.9 (2H, m), 2.66 (3H, s), 2.6-2.9 (3H, m), 3.04 (3H, s), 4.2-4.4 (2H, m), 5.22 (2H, s), 6.6-7.0 (2H, m), 7.41 (1H, d, J=8 Hz), 7.55 (1H, dd, J=2 Hz, 8 Hz), 7.96 (1H, d, J=8 Hz), 8.48 (1H, d, J=2 Hz).

Example 86

(Pharmacological Experiment 1)
(1) Construction of the Stable Cell Line expressing Human G-Protein Coupled Receptor 119 (hGPR119)

hGPR119 gene (NM 178471) was purchased from American Type Culture Collection (ATCC No. 10807349). The forward primer that was added a HindIII site (tcctggatccatggaatcatctttctcatt (sequence number 1)), and the reverse primer that was added an ApaI site (tcctgggcccttagccatcaaactctgagc (sequence number 2)) were designed, the target gene was amplified by polymerase chain reaction (PCR) using a KOD-Plus-Ver. 2 (TOYOBO #KOD-211). PCR was repeated 3 steps (98° C. for 10 sec, 55° C. for 30 sec, 68° C. for 1 min 15 sec) by 35 cycles. Amplified PCR product was inserted in pcDNA5/FRT/TO (Invitrogen #V6520-20), and the stable cell line that expresses target gene when induced with tetracycline was created using the Flp-In T-Rex system (Invitrogen).

(2) Measuring Method of Intracellular Cyclic Adenosine Monophosphate (cAMP)

hGPR119 stable cells made by above-mentioned (1) were plated on 96 well plates in Dulbecco's Modified Eagle Medium containing 10% heat-inactivated FBS. After 24 hours, the hGPR119 expression was induced by adding medium containing tetracycline (Invitrogen #Q10019) and incubating for another 24 hours. Following incubation, cells were stimulated by 0.5 mM 3-ISOBUTYL-1-METHYLXANTHINE (Sigma #I7018) phosphate buffered saline containing test compound for 30 minutes at 37° C. Agonist activity of test compound to the GPR119 receptor was estimated by measuring the intracellular cAMP concentration using a Fluostar optima plate reader (BMG LABTECH) according to the manufacturer's protocol of the HitHunter™ cAMP XS Assay (GE Healthcare #90007503).

(3) Experimental Result

Examination results are shown in Table 16

TABLE 16

| Test compound | EC$_{50}$ (nM) |
|---|---|
| Example 1 | 26.8 |
| Example 2 | 606 |

As is clear from Table 16, the compounds of Example 1 and 2 according to the invention show an excellent GPR119 agonist effect.

Example 87

(Pharmacological Experiment 2)

The examination was performed by the method similar to Example 86 (Pharmacological experiment 1)-(1), -(2). Those results are shown in Table 17

TABLE 17

| Test compound | EC$_{50}$ (nM) |
|---|---|
| Example 8 | 137 |
| Example 12 | 54.7 |
| Example 16 | 129 |
| Example 17 | 34.0 |
| Example 18 | 85.4 |
| Example 21 | 59.3 |
| Example 22 | 24.0 |
| Example 25 | 21.2 |
| Example 37 | 80.6 |
| Example 41 | 114 |
| Example 48 | 137 |
| Example 51 | 257 |
| Example 63 | 28.4 |
| Example 71 | 29.3 |
| Example 73 | 48.0 |
| Example 75 | 22.4 |
| Example 79 | 142 |
| Example 80 | 65.9 |
| Example 81 | 39.2 |
| Example 82 | 58.8 |
| Example 83 | 21.9 |
| Example 84 | 128 |

Example 88

(Pharmacological Experiment 3)

Oral glucose tolerance test in normal mice (Experimental Procedure)

In this experiment, we examined the inhibitory effect of test compound on glycemic excursions after glucose administration in normal mice. The test methods are shown as follows.

Male 9-week-old ICR mice, habituated to the experimental environment for two weeks, were fasted for 18 hours and used to this experiment. Mice were orally administered the test compound or vehicle (polyethylene glycol 400: ethanol: Tween80-8:1:1), and after 30 minutes, they were orally given glucose at the dose of 3 g/kg.

Blood was collected at just before the test compound or vehicle administration (−30 min), immediately before glucose challenge (0 min), 20 min, 40 min, 60 min and 120 min after glucose ingestion and then blood glucose levels were determined.

Inhibition rate (%) of the test compound versus vehicle in areas under the glycemic excursion curve between 0 and 120 min after glucose challenge was determined.

(Experimental Result)

Results are shown at table 18.

TABLE 18

| Test compound (10 mg/kg) | Inhibition rate (%) |
|---|---|
| Example 1 | 41.8 |

As described above, this invented compound showed strong inhibitory effect of glycemic excursions on oral glucose tolerance test in normal mice.

The invention claimed is:

1. A compound having the following formula (I) or a pharmaceutically acceptable salt thereof:

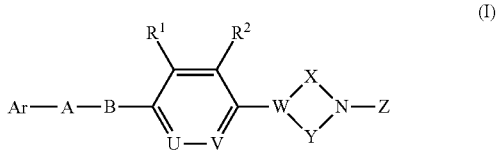

(I)

wherein Ar is pyridyl, which optionally has a substituent or substituents selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, phenylsulfonyl, and a five-membered or six-membered heteroaryl group;

A is $(CH_2)_m$, O, S, $NR^3$, or a bond, wherein m is an integer of 1 to 3, and $R^3$ is hydrogen or a $C_{1-8}$ alkyl group;

B is $(CH_2)_n$, CH=CH, O, S, or $NR^4$, wherein n is an integer of 1 to 3, and $R^4$ is hydrogen or a $C_{1-8}$ alkyl group, provided that B is neither O, S, nor $NR^4$ when A is O, S, or $NR^3$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl, a $C_{1-8}$ alkoxy group, a $C_{1-8}$ alkyl group having one to three halogen atoms, or a $C_{1-8}$ alkoxy group having one to three halogen atoms;

X is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is $C(O)OR^7$, $C(O)R^8$, $C(O)NR^{10}R^{11}$, $CH_2C(O)N(R^{12})(R^{13})$, or a five-membered or six-membered heteroaryl group comprising carbon and nitrogen atoms, said carbon atom combining to the nitrogen atom of the neighboring cyclic amine, and said heteroaryl group optionally having a substituent or substituents selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms, wherein each of $R^7$, $R^8$, $R^{10}$, $R^{11}$, $R^{12}$, and $R^{13}$ independently is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^1$ and $R^2$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

2. A compound having the following formula (I) or a pharmaceutically acceptable salt thereof:

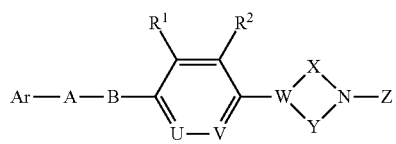

(I)

wherein Ar is phenyl, phenyl having a substituent or substituents, pyridyl, or pyridyl having a substituent or substituents, said substituent being $C_{1-8}$ alkylsulfonyl;

A is $(CH_2)_m$, O, S, $NR^3$, or a bond, wherein m is an integer of 1 to 3, and $R^3$ is hydrogen or a $C_{1-8}$ alkyl group;

B is $(CH_2)_n$, CH=CH, O, S, or $NR^4$, wherein n is an integer of 1 to 3, and $R^4$ is hydrogen or a $C_{1-8}$ alkyl group, provided that B is neither O, S, nor $NR^4$ when A is O, S, or $NR^3$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl, a $C_{1-8}$ alkoxy group, a $C_{1-8}$ alkyl group having one to three halogen atoms, or a $C_{1-8}$ alkoxy group having one to three halogen atoms;

X is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is $C(O)OR^7$, $C(O)R^8$, $C(O)NR^{10}R^{11}$, $CH_2C(O)N(R^{12})(R^{13})$, or a five-membered or six-membered heteroaryl group comprising carbon and nitrogen atoms, said carbon atom combining to the nitrogen atom of the neighboring cyclic amine, and said heteroaryl group optionally having a substituent or substituents selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms, wherein each of $R^7$, $R^8$, $R^{10}$, $R^{11}$, $R^{12}$, and $R^{13}$ independently is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^1$ and $R^2$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

3. A compound having the following formula (I) or a pharmaceutically acceptable salt thereof:

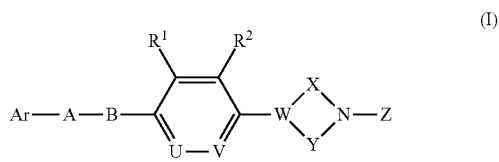

(I)

wherein Ar is an aryl or five-membered or six-membered heteroaryl group, which optionally has a substituent or substituents selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, a $C_{2-12}$ dialkylaminosulfonyl group, phenyl sulfonyl, and a five-membered or six-membered heteroaryl group;

A is S

B is $CH_2$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl, a $C_{1-8}$ alkoxy group, a $C_{1-8}$ alkyl group having one to three halogen atoms, or a $C_{1-8}$ alkoxy group having one to three halogen atoms;

X is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is $C(O)OR^7$, $C(O)R^8$, $C(O)NR^{10}R^{11}$, $CH_2C(O)N(R^{12})(R^{13})$, or a five-membered or six-membered heteroaryl group comprising carbon and nitrogen atoms, said carbon atom combining to the nitrogen atom of the neighboring cyclic amine, and said heteroaryl group optionally having a substituent or substituents selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms, wherein each of $R^7$, $R^8$, $R^{10}$, $R^{11}$, $R^{12}$, and $R^{13}$ independently is a $C_{1-8}$ alkyl group, a $C_{2-8}$ alkenyl group, a $C_{3-8}$ cycloalkyl group, phenyl, or a $C_{1-8}$ alkyl group having phenyl; and each of $R^1$ and $R^2$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

4. A compound having the following formula (I) or a pharmaceutically acceptable salt thereof:

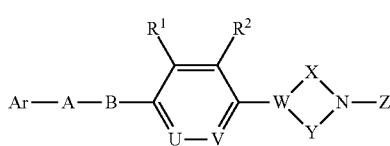

(I)

wherein Ar is an aryl or five-membered or six-membered heteroaryl group, which optionally has a substituent or substituents selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, a $C_{2-12}$ dialkylaminosulfonyl group, phenylsulfonyl, and a five-membered or six-membered heteroaryl group;

A is $(CH_2)_m$, O, S, $NR^3$, or a bond, wherein m is an integer of 1 to 3, and $R^3$ is hydrogen or a $C_{1-8}$ alkyl group;

B is $(CH_2)_n$, CH=CH, O, S, or $NR^4$, wherein n is an integer of 1 to 3, and $R^4$ is hydrogen or a $C_{1-8}$ alkyl group, provided that B is neither O, S, nor $NR^4$ when A is O, S, or $NR^3$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl, a $C_{1-8}$ alkoxy group, a $C_{1-8}$ alkyl group having one to three halogen atoms, or a $C_{1-8}$ alkoxy group having one to three halogen atoms;

X is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is 3-$C_{1-8}$ alkyl-1,2,4-oxadiazol-5-yl or 5-$C_{1-8}$ alkyl-1,2,4-oxadiazol-3-yl; and each of $R^1$ and $R^2$ independently is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms.

5. A compound having the following formula (I) or a pharmaceutically acceptable salt thereof:

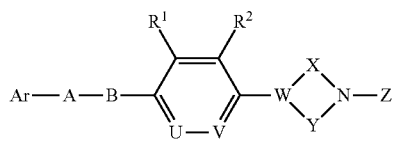

(I)

wherein Ar is an aryl or five-membered or six-membered heteroaryl group, which optionally has a substituent or substituents selected from the group consisting of a halogen atom, nitro, cyano, hydroxyl, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, phenoxy, an alkoxycarbonyl group having a $C_{1-8}$ alkoxy group, carboxyl, carbamoyl, an acyl group having a $C_{1-8}$ alkyl group, an alkylaminocarbonyl group having a $C_{1-8}$ alkyl group, a dialkylaminocarbonyl group having $C_{2-12}$ alkyl groups, an alkoxycarbonylmethylcarbonyl group having a $C_{1-8}$ alkoxy group, an alkylsulfonylmethyl group having a $C_{1-8}$ alkyl group, amino, a $C_{1-8}$ alkylamino group, a $C_{2-12}$ dialkylamino group, a $C_{1-8}$ alkylsulfonylamino group, an acylamino group having a $C_{1-8}$ alkyl group, a $C_{1-8}$ alkylsulfinyl group, a $C_{1-8}$ alkylsulfonyl group, sulfamoyl, a $C_{1-8}$ alkylaminosulfonyl group, a $C_{2-12}$ dialkylaminosulfonyl group, phenylsulfonyl, and a five-membered or six-membered heteroaryl group;

A is $(CH_2)_m$, O, S, $NR^3$, or a bond, wherein m is an integer of 1 to 3, and $R^3$ is hydrogen or a $C_{1-8}$ alkyl group;

B is $(CH_2)_n$, CH=CH, O, S, or $NR^4$, wherein n is an integer of 1 to 3, and $R^4$ is hydrogen or a $C_{1-8}$ alkyl group, provided that B is neither O, S, nor $NR^4$ when A is O, S, or $NR^3$;

one of U and V is N, and the other is N or $CR^5$, wherein $R^5$ is hydrogen, a halogen atom, hydroxyl, a $C_{1-8}$ alkyl group, a $C_{1-8}$ alkoxy group, a $C_{1-8}$ alkyl group having one to three halogen atoms, or a $C_{1-8}$ alkoxy group having one to three halogen atoms;

W is C or $CR^6$, wherein $R^6$ is hydrogen, a halogen atom, hydroxyl, a $C_{1-8}$ alkyl, a $C_{1-8}$ alkoxy group, a $C_{1-8}$ alkyl group having one to three halogen atoms, or a $C_{1-8}$ alkoxy group having one to three halogen atoms;

X is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

when W is C, X combines to W with a double bond;

Y is a $C_{1-3}$ alkylene group, which optionally has a substituent or substituents selected from the group consisting of a halogen atom, hydroxyl, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms;

Z is $C(O)OR^7$, $C(O)R^8$, $C(O)NR^{10}R^{11}$, $CH_2C(O)N(R^{12})(R^{13})$, or a five-membered or six-membered heteroaryl group comprising carbon and nitrogen atoms, said carbon atom combining to the nitrogen atom of the neighboring cyclic amine, and said heteroaryl group optionally having a substituent or substituents selected from the group consisting of a halogen atom, a $C_{1-8}$ alkyl group, a $C_{1-8}$ alkoxy group, a $C_{1-8}$ alkyl group having one to three halogen atoms, and a $C_{1-8}$ alkoxy group having one to three halogen atoms, wherein each of $R^7$, $R^8$, $R^{10}$, $R^{11}$, $R^{12}$, and $R^{13}$ independently is a $C_{1-8}$ alkyl group, a $C_{2-8}$ alkenyl group, a $C_{3-8}$ cycloalkyl group, phenyl, or a $C_{1-8}$ alkyl group having phenyl; and $R^1$ is a halogen atom, and $R^2$ is hydrogen.

* * * * *